(12) United States Patent
Vaishnaw et al.

(10) Patent No.: US 9,127,277 B2
(45) Date of Patent: *Sep. 8, 2015

(54) METHODS AND COMPOSITIONS FOR PREVENTION OR TREATMENT OF RSV INFECTION

(71) Applicant: Alnylam Pharmaceuticals, Inc., Cambridge, MA (US)

(72) Inventors: Akshay Vaishnaw, Arlington, MA (US); Saraswathy V. Nochur, Newton, MA (US); Sayda Elbashir, Cambridge, MA (US); Muthiah Manoharan, Weston, MA (US); Rachel Meyers, Newton, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/778,614

(22) Filed: Feb. 27, 2013

(65) Prior Publication Data
US 2013/0165499 A1     Jun. 27, 2013

Related U.S. Application Data

(63) Continuation of application No. 13/359,421, filed on Jan. 26, 2012, now Pat. No. 8,410,073, which is a continuation of application No. 12/335,467, filed on Dec. 15, 2008, now abandoned.

(60) Provisional application No. 61/013,428, filed on Dec. 13, 2007, provisional application No. 61/014,887, filed on Dec. 19, 2007, provisional application No. 61/021,309, filed on Jan. 15, 2008, provisional application No. 61/034,084, filed on Mar. 5, 2008, provisional application No. 61/049,076, filed on Apr. 30, 2008.

(51) Int. Cl.
| | | |
|---|---|---|
| *A61K 31/70* | (2006.01) | |
| *C07H 21/02* | (2006.01) | |
| *C07H 21/04* | (2006.01) | |
| *C12N 15/113* | (2010.01) | |
| *A61K 31/713* | (2006.01) | |
| *A61K 31/708* | (2006.01) | |
| *A61M 11/00* | (2006.01) | |
| *C12Q 1/68* | (2006.01) | |

(52) U.S. Cl.
CPC .......... *C12N 15/1131* (2013.01); *A61K 31/708* (2013.01); *A61K 31/713* (2013.01); *A61M 11/00* (2013.01); *C12N 2310/14* (2013.01)

(58) Field of Classification Search
None
See application file for complete search history.

(56) References Cited

U.S. PATENT DOCUMENTS

| | | |
|---|---|---|
| 7,427,605 B2 | 9/2008 | Davis et al. |
| 7,718,629 B2 | 5/2010 | Bumcrot et al. |
| 2003/0143732 A1 | 7/2003 | Fosnaugh et al. |
| 2003/0170891 A1 | 9/2003 | McSwiggen |
| 2004/0259247 A1 | 12/2004 | Tuschl et al. |
| 2006/0263435 A1 | 11/2006 | Davis et al. |
| 2006/0287267 A1 | 12/2006 | Vaish et al. |
| 2007/0004664 A1 | 1/2007 | McSwiggen et al. |
| 2007/0031844 A1 | 2/2007 | Khvorova et al. |
| 2007/0281899 A1 | 12/2007 | Bumcrot et al. |
| 2009/0149403 A1 | 6/2009 | MacLachlan |
| 2011/0015250 A1 | 1/2011 | Bumcrot et al. |
| 2012/0244207 A1 | 9/2012 | Fitzgerald et al. |

FOREIGN PATENT DOCUMENTS

| | | |
|---|---|---|
| WO | WO 2004/080406 | 9/2004 |
| WO | WO 2004/090108 | 10/2004 |
| WO | WO 2010/147992 | 12/2010 |

OTHER PUBLICATIONS

Agrawal, S., et al., "Antisense oligonucleotides: towards clinical trials." Trends in Biotechnology. Oct. 1996, vol. 14, pp. 376-387.
Australian Government—IP Australia, Patent Examination Report No. 1, Australian Patent Application No. 2008334948, Mar. 6, 2013, 3 Pages.
Bass, B., "The short answer," Nature, May 24, 2001, pp. 428-429, vol. 411.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in *Caenorhabditis elegans*," Nature, Feb. 19, 1998, pp. 806-811, vol. 391.
Hornung, V., et al., "Sequence-specific potent induction of IFN-α by short interfering RNA in plasmacytoid dendritic cells throughTLR7," Nature Medicine, Mar. 2005, pp. 263-270, vol. 11, No. 3.
Reynolds, et al. (2004) "Rational siRNA design for RNA interference," Nature Biotechnology, vol. 22, No. 3, pp. 326-330.

(Continued)

*Primary Examiner* — Sean McGarry
(74) *Attorney, Agent, or Firm* — Fenwick & West LLP

(57) ABSTRACT

Methods and compositions are provided for the prevention or treatment of RSV infection in a human. The methods include administering one or more doses of a composition comprising an siRNA. The dose can be formulated for topical or parenteral administration. Topical administration includes administration as a nasal spray, or by inhalation of respirable particles or droplets.

27 Claims, 46 Drawing Sheets

(56) References Cited

OTHER PUBLICATIONS

Figure 2:
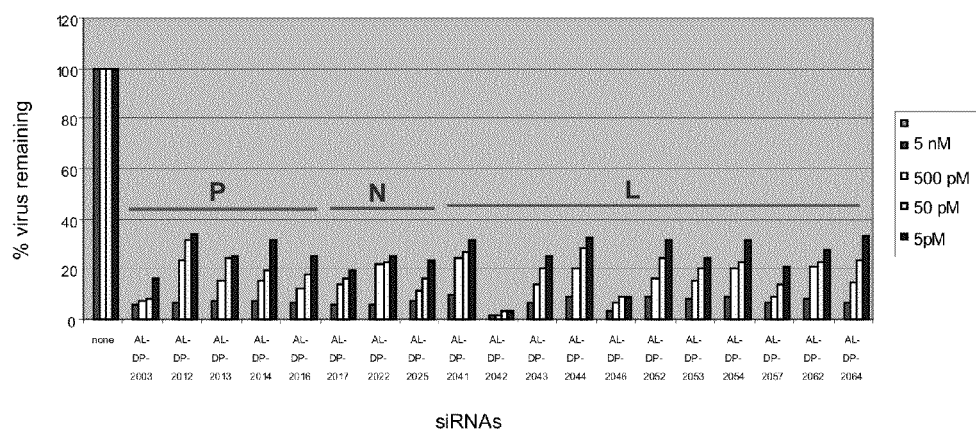

Robbins, M., et al., "Stable expression of shRNAs in human CD34+ progenitor cells can avoid induction of interferon responses to siRNAs in vitro," Nature Biotechnology, May 2006, pp. 566-571, vol. 24, No. 5.

Rose, S., et al., "Functional polarity is introduced by Dicer processing of short substrate RNAs," Nucleic Acids Research, 2005, pp. 4140-4156, vol. 33, No. 13.

Tuschl, T., "Functional genomics: RNA sets the standard," Nature, Jan. 16, 2003, vol. 421, No. 6920, pp. 220-221.

Tuschl T., "RNA Interference and Small Interfering RNAs" Chembiochem, 2001, pp. 239-245, vol. 2.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., "Mammalian RNA Interference," RNAi, A Guide to Gene Silencing, Chapter 13, G.J. Hannon (ed,), 2003, pp. 265-295.

Tuschl, T., et al., "Targeted mRNA Degradation by Double-Stranded RNA In Vitro," Genes & Development, 1999, pp. 3191-3197, vol. 13.

Tuschl, T., "Expanding small RNA interference," Nature Biotechnology, May 2002, pp. 446-448, vol. 20.

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

Weil, et al (2002) "Targeting the Kinesin Eg5 to Monitor siRNA Transfection in Mammalian Cells," *Biotechniques* 33(6):1244-1248.

Zimmerman, et al. (2006) "RNAi-mediated gene silencing in non-human primates," *Nature*, vol. 441, May 4: 111-114.

Office Action for U.S. Appl. No. 13/434,820, Dec. 4, 2013, 6 Pages.

Sample Symptom Score Card

| Level | 0 | 1 | 2 | 3 | Other symptoms |
|---|---|---|---|---|---|
| Symptoms | I have NO symptoms | Just noticeable | It's clearly bothersome from time to time, but it doesn't stop me from participating in activities | It's quite bothersome most of the time, and it doesn't stop me from participating in activities | |
| Runny nose | | | | | |
| Stuffy nose | | | | | |
| Sore throat | | | | | |
| Malaise (tiredness) | | | | | |
| Cough | | | | | |
| Shortness of breath | | | | | |
| Headache | | | | | |
| Muscle and/or joint aches | | | | | |

FIG. 28

Baseline Characteristics of Subjects*

| | | Placebo N=42 | All ALN-RSV01 N=43 |
|---|---|---|---|
| Mean Age (years) | | 27.7 | 28.0 |
| Mean Weight (kg) | | 76.9 | 79.3 |
| Race (%) | Caucasian | 64.3 | 67.4 |
| | Black | 11.9 | 7.0 |
| | Other | 21.4 | 25.6 |
| Mean RSV inoculum (log PFU) (SD) | | 4.70 (0.261) | 4.70 (0.256) |
| Mean Day -2 RSV microneut (MU) (SD) | | 7.25 (1.00) | 6.89 (1.03)** |

*Efficacy evaluable population. Two patients in the placebo group and one in the ALN-RSV01 group were withdrawn prior to RSV inoculation due to gastroenteritis caused by food poisoning.
**Difference not statistically significant by Wilcoxan rank sum test.

FIG. 29

Primary Efficacy Outcome: Infection Rate (Cohorts 1-6)

| Detection Method | | Placebo (N=42) | All ALN-RSV01 (N=43) | Magnitude of Effect relative to placebo | Mantel-Haenszel P value |
|---|---|---|---|---|---|
| Quantitative Culture | Infected | 30 (71.4%) | 19 (44.2%) | 38.1% | 0.009 |
| | Uninfected | 12 (28.6%) | 24 (55.8%) | 95.1% | |
| RT-qPCR | Infected | 36 (85.7%) | 29 (67.4%) | 21.4% | 0.051 |
| | Uninfected | 6 (14.3%) | 14 (32.6%) | 128.0% | |
| Spin Enhanced Culture | Infected | 31 (73.8%) | 22 (51.1%) | 30.8% | 0.031 |
| | Uninfected | 11 (26.2%) | 21 (48.8%) | 86.3% | |

FIG. 30

Evaluating Independent Effects on Infection*

A.

| Variable | P Value | Odds Ratio | 95% CI |
|---|---|---|---|
| ALN-RSV01 vs. Placebo | 0.006 | 0.240 | 0.086 - 0.665 |
| RSV inoculum | 0.010 | 16.459 | 1.975 – 137.2 |
| Day -2 RSV microneut titer | 0.139 | 0.694 | 0.427 - 1.126 |
| TNFα AUC (d2-4)<br>(post inoculation, during incubation period) | 0.528 | 1.034 | 0.932-1.147 |

B.

| Variable | P Value | Odds Ratio | 95% CI |
|---|---|---|---|
| ALN-RSV01 vs. Placebo | 0.005 | 0.225 | 0.080 - 0.633 |
| RSV inoculum | 0.009 | 14.281 | 1.935 - 105.416 |
| Day -2 RSV microneut titer | 0.139 | 0.693 | 0.426 - 1.126 |
| G-CSF (d2-8)<br>(post inoculation, through end of infection definition) | 0.342 | 1.000 | 1.000 - 1.000 |

*Measured by quantitative culture

FIG. 31

Treatment-Emergent Adverse Events (≥ 5% Incidence)

| Adverse Effects | Placebo N=44 (%) | ALN-RSV01 75mg N=4 (%) | ALN-RSV01 150mg N=40 (%) | All ALN-RSV01 N=44 (%) |
|---|---|---|---|---|
| Vomiting* | 2 (4.5) | 0 (0.0) | 2 (5.0) | 2 (4.5) |
| Vessel puncture site bruise | 1 (2.3) | 0 (0.0) | 2 (5.0) | 2 (4.5) |
| Upper respiratory tract infection** | 4 (9.1) | 0 (0.0) | 3 (7.5) | 3 (6.8) |
| Back pain | 0 (0.0) | 0 (0.0) | 2 (5.0) | 2 (4.5) |
| Headache | 6 (13.6) | 0 (0.0) | 5 (12.5) | 5 (11.4) |
| Cough | 0 (0.0) | 0 (0.0) | 2 (5.0) | 2 (4.5) |
| Pharyngo-laryngeal pain | 1 (2.3) | 1 (25.0) | 2 (5.0) | 3 (6.8) |

*Occurred in two subjects in placebo group and 1 subject in the 150 mg ALN-RSV01 group (all Cohort 6) who had a GI upset (food related gastroenteritis) after a single dose of study drug, and were discontinued from the study

** All episodes occurred >> Day 12 (post-subject discharge from quarantine)

FIG. 32

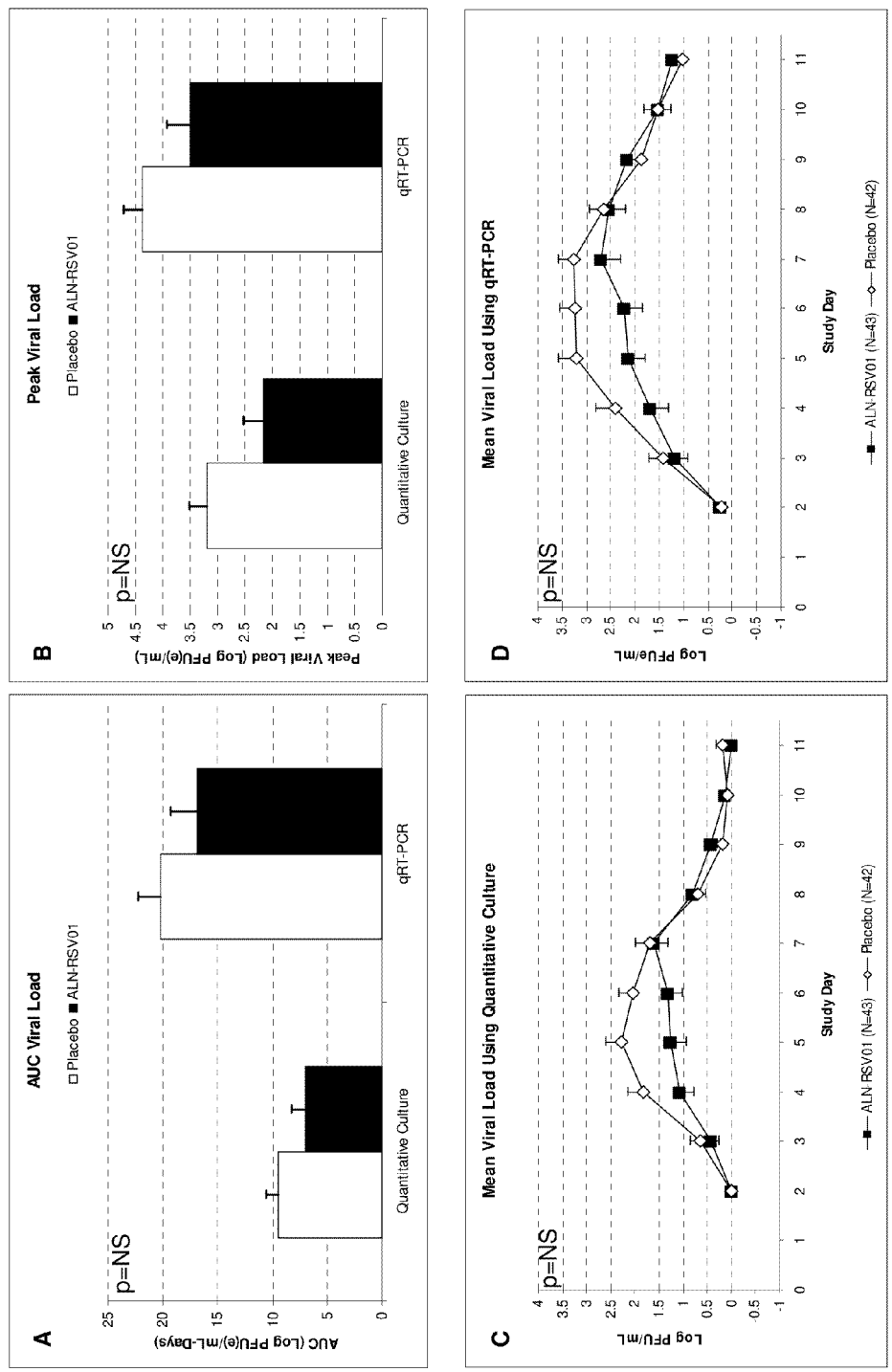
FIG. 35A-D

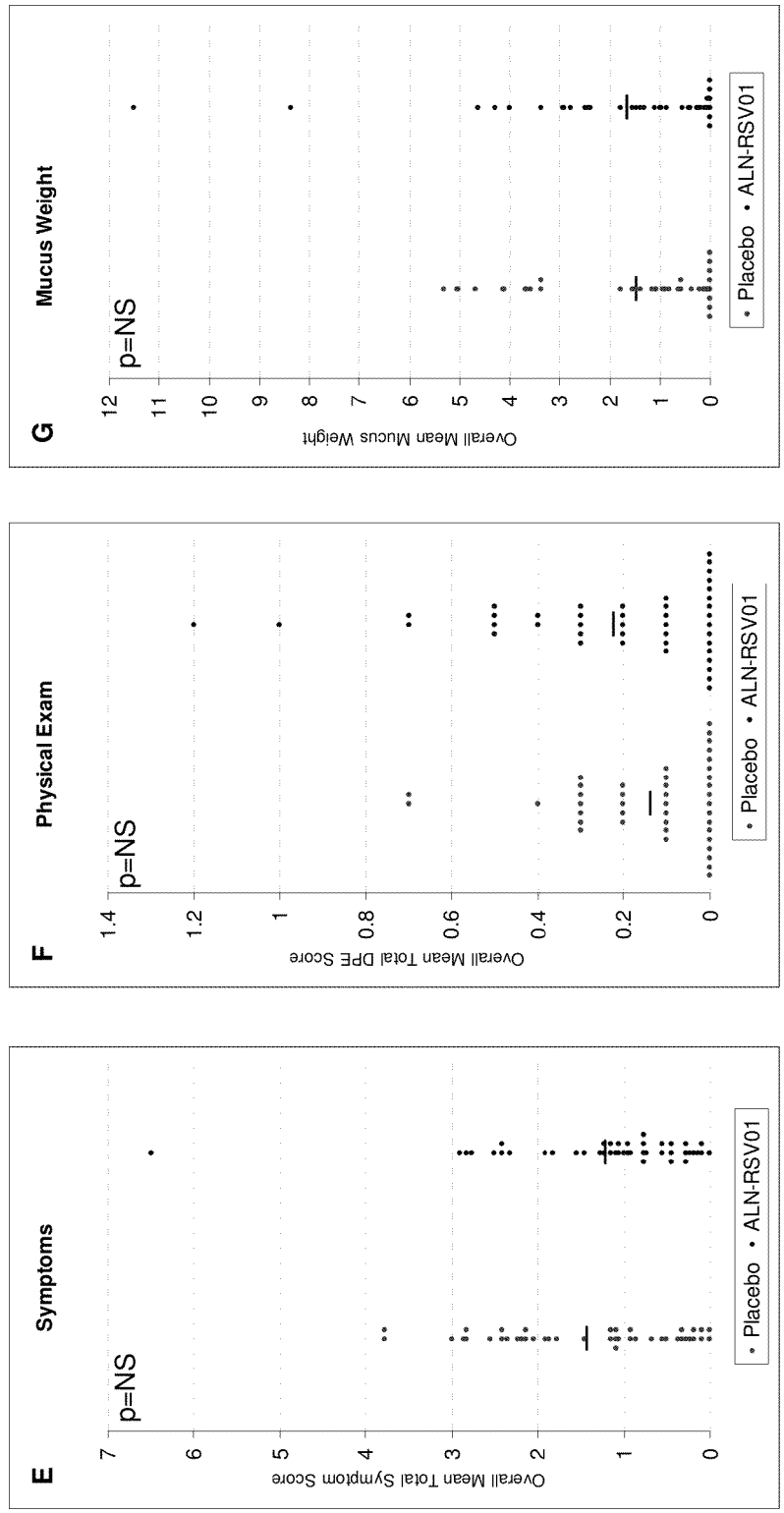
FIG. 35E-G

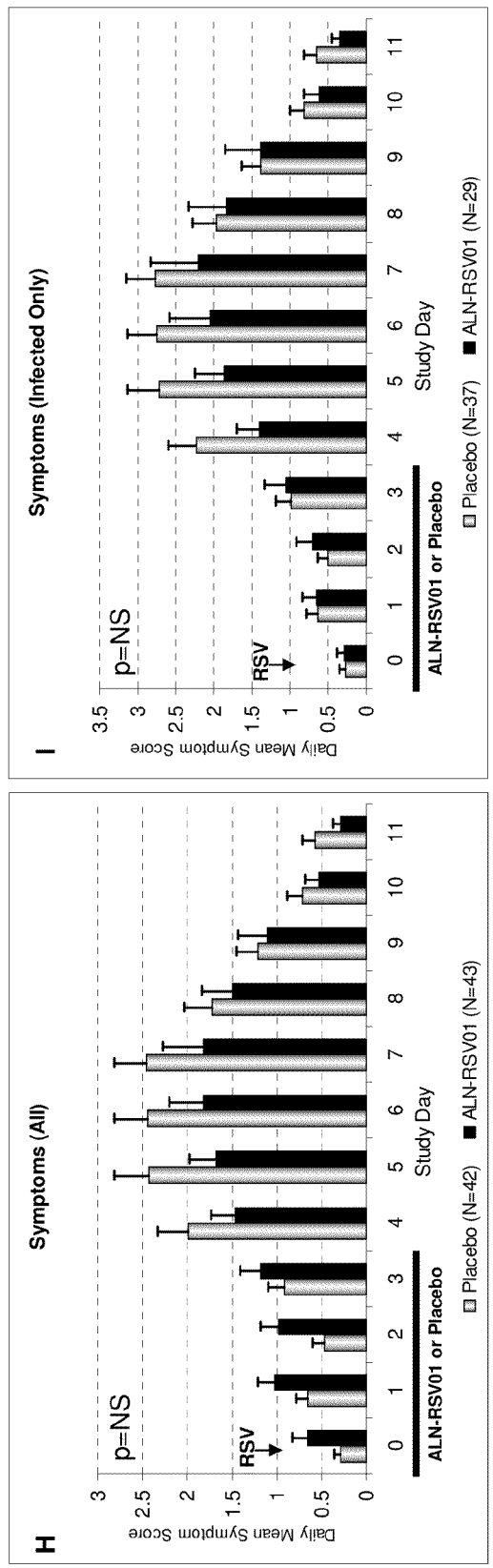
FIG. 35H-I

SEQUENCE LISTING

```
<160> NUMBER OF SEQ ID NOS: 314

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
ggcucuuagc aaagucaagt t                                             21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
cuugacuuug cuaagagcct t                                             21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
ggaucccauu auuaauggat t                                             21
```

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
gaucccauua uuaauggaat t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
aguuauuuaa aagguguuat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
guuauuuaaa agguguuaut t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
auuuaaaagg uguuaucuct t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
uuaaaaggug uuaucucuut t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
aaguccacua cuagagcaut t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
aguccacuac uagagcauat t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
guccacuacu agagcauaut t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
uccacuacua gagcauaugt t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
gaagagcuau agaaauaagt t          21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
gagcuauaga aauaagugat t          21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
cuauagaaau aagugaugut t          21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
ucaaaacaac acucuugaat t          21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
uagagggauu uauuauguct t          21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18

-continued auaaaagggu uuguaaauat t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
cucaguguag guagaaugut t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
ucaguguagg uagaauguut t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
caguguaggu agaauguuut t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
aguguaggua gaauguuugt t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 23
guguagguag aauguuugct t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 24
acaagauaug gugaucuagt t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 25
agcaaauuca aucaagcaut t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 26
gcaaauucaa ucaagcauut t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
gaugaacaaa guggauuaut t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
uaauaucucu caaagggaat t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 29
auaucucuca aagggaaaut t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 30
uaucucucaa agggaaauut t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 31
caugcucaag cagauuauut t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
ugcucaagca gauuauuugt t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic -continued oligonucleotide

<400> SEQUENCE: 33
uagcauuaaa uagccuuaat t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 34
agcauuaaau agccuuaaat t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 35
gcauuaaaua gccuuaaaut t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 36
cauuaaauag ccuuaaauut t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37
uauuaugcag uuuaauauut t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

<223> OTHER INFORMATION: Description of Artificial Sequence: Synthetic
      oligonucleotide

<400> SEQUENCE: 38
uuaugcaguu uaauauuuat t                                               21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 39
aaaagugcac aacauuauat t                                               21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 40
aaagugcaca acauuauact t                                               21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 41
auauagaacc uacauaucct t                                               21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 42
uauagaaccu acauauccut t                                               21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide

```
<220> FEATURE:
<223> OTHER INFORMATION: Description of Artificial Sequence: Synthetic
      oligonucleotide

<400> SEQUENCE: 43
uaagaguugu uuaugaaagt t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 44
acagucagua guagaccaut t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 45
cagucaguag uagaccaugt t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 46
agucaguagu agaccaugut t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 47
gucaguagua gaccaugugt t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
```

```
                Synthetic oligonucleotide
<220> FEATURE:
<223> OTHER INFORMATION: Description of Artificial Sequence: Synthetic
      oligonucleotide

<400> SEQUENCE: 48
ucaguaguag accaugugat t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
caugugaauu cccugcauct t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 50
augugaauuc ccugcaucat t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
ugugaauucc cugcaucaat t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
gugaauuccc ugcaucaaut t                                              21

<210> SEQ ID NO 53
<211> LENGTH: 21
<212> TYPE: DNA
<213> ORGANISM: Artificial Sequence
<220> FEATURE:
```

<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 53
aauucccugc aucaauacct t                                                21

<210> SEQ ID NO 54
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 54
gcaucaauac cagcuuauat t                                                21

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 55
caucaauacc agcuuauagt t                                                21

<210> SEQ ID NO 56
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 56
auaccagcuu auagaacaat t                                                21

<210> SEQ ID NO 57
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 57
uaccagcuua uagaacaact t                                                21

<210> SEQ ID NO 58
<211> LENGTH: 21
<212> TYPE: DNA
<213> ORGANISM: Artificial Sequence

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 58
accagcuuau agaacaacat t                                                    21

<210> SEQ ID NO 59
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 59
ccagcuuaua gaacaacaat t                                                    21

<210> SEQ ID NO 60
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 60
cagcuuauag aacaacaaat t                                                    21

<210> SEQ ID NO 61
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 61
auagaacaac aaauuaucat t                                                    21

<210> SEQ ID NO 62
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 62
uauuaacaga aaaguauggt t                                                    21

<210> SEQ ID NO 63
<211> LENGTH: 21
<212> TYPE: DNA
```

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 63
ugagauacau uugaugaaat t                                            21

<210> SEQ ID NO 64
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 64
gagauacauu ugaugaaact t                                            21

<210> SEQ ID NO 65
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 65
gauacauuug augaaaccut t                                            21

<210> SEQ ID NO 66
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 66
auacauuuga ugaaaccuct t                                            21

<210> SEQ ID NO 67
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 67
uacauuugau gaaaccucct t                                            21

<210> SEQ ID NO 68
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 68
aagugauaca aaaacagcat t                                             21

<210> SEQ ID NO 69
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 69
agugauacaa aaacagcaut t                                             21

<210> SEQ ID NO 70
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 70
ugauacaaaa acagcauaut t                                             21

<210> SEQ ID NO 71
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 71
uuuaaguacu aauuuagcut t                                             21

<210> SEQ ID NO 72
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 72
uuaaguacua auuuagcugt t                                             21

<210> SEQ ID NO 73
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 73
uaaguacuaa uuuagcuggt t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 74
aaguacuaau uuagcuggat t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 75
aguacuaauu uagcuggact t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 76
guacuaauuu agcuggacat t                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 77
acuaauuuag cuggacauut t                                              21
```

```
<210> SEQ ID NO 78
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 78
aauuuagcug gacauuggat t                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 79
auuuagcugg acauuggaut t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 80
uuagcuggac auuggauuct t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 81
uuuugaaaaa gauugggat t                                               21

<210> SEQ ID NO 82
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 82
uuugaaaaag auuggggagt t                                              21
```

<210> SEQ ID NO 83
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 83
ugaaaaagau ugggagagt t                                          21

<210> SEQ ID NO 84
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 84
gaaaaagauu ggggagaggt t                                         21

<210> SEQ ID NO 85
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 85
uaugaacacu ucagaucuut t                                         21

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 86
augaacacuu cagaucuuct t                                         21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 87
ugcccuuggg uuguuaacat t                                         21

<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Molecule:
    Synthetic oligonucleotide
<220> FEATURE:
<223> OTHER INFORMATION: Description of Artificial Sequence: Synthetic
    oligonucleotide

<400> SEQUENCE: 88
gcccuugggu uguuaacaut t                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Combined DNA/RNA Molecule:
    Synthetic oligonucleotide
<220> FEATURE:
<223> OTHER INFORMATION: Description of Artificial Sequence: Synthetic
    oligonucleotide

<400> SEQUENCE: 89
uauagcauuc auaggugaat t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
    Synthetic oligonucleotide
<220> FEATURE:
<223> OTHER INFORMATION: Description of Artificial Sequence: Synthetic
    oligonucleotide

<400> SEQUENCE: 90
auagcauuca uaggugaagt t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Combined DNA/RNA Molecule:
    Synthetic oligonucleotide
<220> FEATURE:
<223> OTHER INFORMATION: Description of Artificial Sequence: Synthetic
    oligonucleotide

<400> SEQUENCE: 91
uagcauucau aggugaaggt t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Combined DNA/RNA Molecule:
    Synthetic oligonucleotide
<220> FEATURE:
<223> OTHER INFORMATION: Description of Artificial Sequence: Synthetic
    oligonucleotide

<400> SEQUENCE: 92
auucauaggu gaaggagcat t                                                  21

<210> SEQ ID NO 93
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 93
uugcaaugau cauaguuuat t                                                  21

<210> SEQ ID NO 94
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 94
ugcaaugauc auaguuuact t                                                  21

<210> SEQ ID NO 95
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 95
gcaaugauca uaguuuacct t                                                  21

<210> SEQ ID NO 96
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 96
caaugaucau aguuuaccut t                                                  21

<210> SEQ ID NO 97
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 97

```
aaugaucaua guuuaccuat t                                            21

<210> SEQ ID NO 98
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 98
augaucauag uuuaccuaut t                                            21

<210> SEQ ID NO 99
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 99
gaucauaguu uaccuauugt t                                            21

<210> SEQ ID NO 100
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 100
aucauaguuu accuauugat t                                            21

<210> SEQ ID NO 101
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 101
ucauaguuua ccuauugagt t                                            21

<210> SEQ ID NO 102
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 102
cauaguuuac cuauugagut t                                            21

<210> SEQ ID NO 103
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 103
auaguuuacc uauugaguut t                                            21

<210> SEQ ID NO 104
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 104
cauuggucuu auuuacauat t                                            21

<210> SEQ ID NO 105
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 105
uuggucuuau uuacauauat t                                            21

<210> SEQ ID NO 106
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 106
uggucuuauu uacauauaat t                                            21

<210> SEQ ID NO 107
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

<400> SEQUENCE: 107
ggucuuauuu acauauaaat t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 108
auaucaugcu caagaugaut t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 109
uaucaugcuc aagaugauat t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 110
ugauauugau uucaaauuat t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 111
uacuuagucc uuacaauagt t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic -continued oligonucleotide

<400> SEQUENCE: 112
uuaguccuua caauagguct t                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 113
uaguccuuac aauaggucct t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 114
auauucuaua gcuggacgut t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 115
uauucuauag cuggacguat t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 116
auucuauagc uggacguaat t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

```
<223> OTHER INFORMATION: Description of Artificial Sequence: Synthetic
      oligonucleotide

<400> SEQUENCE: 117
uccauuaaua augggaucct t                                            21

<210> SEQ ID NO 118
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 118
uuccauuaau aaugggauct t                                            21

<210> SEQ ID NO 119
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 119
uaacaccuuu uaaauaacut t                                            21

<210> SEQ ID NO 120
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 120
auaacaccuu uuaaauaact t                                            21

<210> SEQ ID NO 121
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 121
gagauaacac cuuuuaaaut t                                            21

<210> SEQ ID NO 122
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 122
aagagauaac accuuuuaat t                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 123
augcucuagu aguggacuut t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 124
uaugcucuag uaguggacut t                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 125
auaugcucua guaguggact t                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 126
cauaugcucu aguaguggat t                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Combined DNA/RNA Molecule:
```

Synthetic oligonucleotide
<220> FEATURE:
<223> OTHER INFORMATION: Description of Artificial Sequence: Synthetic
      oligonucleotide

<400> SEQUENCE: 127
cuuauuucua uagcucuuct t                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 128
ucacuuauuu cuauagcuct t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 129
acaucacuua uuucuauagt t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 130
uucaagagug uuguuuugat t                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 131
gacauaauaa aucccucuat t                                              21

<210> SEQ ID NO 132
<211> LENGTH: 21
<212> TYPE: DNA
<213> ORGANISM: Artificial Sequence
<220> FEATURE:

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 132
uauuuacaaa cccuuuuaut t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 133
acauucuacc uacacugagt t                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 134
aacauucuac cuacacugat t                                              21

<210> SEQ ID NO 135
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 135
aaacauucua ccuacacugt t                                              21

<210> SEQ ID NO 136
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 136
caaacauucu accuacacut t                                              21

<210> SEQ ID NO 137
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 137
gcaaacauuc uaccuacact t                                              21

<210> SEQ ID NO 138
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 138
cuagaucacc auaucuugut t                                              21

<210> SEQ ID NO 139
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 139
augcuugauu gaauuugcut t                                              21

<210> SEQ ID NO 140
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 140
aaugcuugau ugaauuugct t                                              21

<210> SEQ ID NO 141
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 141
auaauccacu uuguucauct t                                              21

<210> SEQ ID NO 142
<211> LENGTH: 21
<212> TYPE: DNA
```

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 142
uucccuuuga gagauauuat t                                               21

<210> SEQ ID NO 143
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 143
auuucccuuu gagagauaut t                                               21

<210> SEQ ID NO 144
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 144
aauuucccuu ugagagauat t                                               21

<210> SEQ ID NO 145
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 145
aauaaucugc uugagcaugt t                                               21

<210> SEQ ID NO 146
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 146
caaauaaucu gcuugagcat t                                               21

<210> SEQ ID NO 147
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 147
uuaaggcuau uuaaugcuat t                                          21

<210> SEQ ID NO 148
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 148
uuuaaggcua uuuaaugcut t                                          21

<210> SEQ ID NO 149
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 149
auuuaaggcu auuuaaugct t                                          21

<210> SEQ ID NO 150
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 150
aauuuaaggc uauuuaaugt t                                          21

<210> SEQ ID NO 151
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 151
aauauuaaac ugcauaaaut t                                          21

<210> SEQ ID NO 152
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 152
uaaauauuaa acugcauaat t                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 153
uauaauguug ugcacuuuut t                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 154
guauaauguu gugcacuuut t                                              21

<210> SEQ ID NO 155
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 155
ggauauguag guucuauaut t                                              21

<210> SEQ ID NO 156
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 156
aggauaugua gguucuauat t                                              21
```

```
<210> SEQ ID NO 157
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 157
cuuucauaaa caacucuuat t                                             21

<210> SEQ ID NO 158
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 158
auggucuacu acugacugut t                                             21

<210> SEQ ID NO 159
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 159
cauggucuac uacugacugt t                                             21

<210> SEQ ID NO 160
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 160
acauggucua cuacugacut t                                             21

<210> SEQ ID NO 161
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 161
cacauggucu acuacugact t                                             21
```

<210> SEQ ID NO 162
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 162
ucacaugguc uacuacugat t                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 163
gaugcaggga auucacaugt t                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 164
ugaugcaggg aauucacaut t                                              21

<210> SEQ ID NO 165
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 165
uugaugcagg gaauucacat t                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 166
auugaugcag ggaauucact t                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 167
gguauugaug cagggaauut t                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 168
uauaagcugg uauugaugct t                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 169
cuauaagcug guauugaugt t                                              21

<210> SEQ ID NO 170
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 170
uuguucuaua agcugguaut t                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 171
guuguucuau aagcugguat t                                                  21

<210> SEQ ID NO 172
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 172
uguuguucua uaagcuggut t                                                  21

<210> SEQ ID NO 173
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 173
uuguuguucu auaagcuggt t                                                  21

<210> SEQ ID NO 174
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 174
uuuguuguuc uauaagcugt t                                                  21

<210> SEQ ID NO 175
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 175
ugauaauuug uuguucuaut t                                                  21

<210> SEQ ID NO 176
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 176
ccauacuuuu cguuaaauat t                                              21

<210> SEQ ID NO 177
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 177
uuucaucaaa uguaucucat t                                              21

<210> SEQ ID NO 178
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 178
guuucaucaa auguaucuct t                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 179
agguuucauc aaauguauct t                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 180
gagguuucau caaauguaut t                                              21

<210> SEQ ID NO 181
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 181
ggagguuuca ucaaauguat t                                              21

<210> SEQ ID NO 182
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 182
ugcuguuuuu guaucacuut t                                              21

<210> SEQ ID NO 183
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 183
augcuguuuu uguaucacut t                                              21

<210> SEQ ID NO 184
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 184
auaugcuguu uuuguaucat t                                              21

<210> SEQ ID NO 185
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 185
agcuaaauua guacuuaaat t                                              21

<210> SEQ ID NO 186
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 186
cagcuaaauu aguacuuaat t                                                  21

<210> SEQ ID NO 187
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 187
ccagcuaaau uaguacuuat t                                                  21

<210> SEQ ID NO 188
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 188
uccagcuaaa uuaguacuut t                                                  21

<210> SEQ ID NO 189
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 189
guccagcuaa auuaguacut t                                                  21

<210> SEQ ID NO 190
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 190
uguccagcua aauuaguact t                                                  21

<210> SEQ ID NO 191
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
``` oligonucleotide

<400> SEQUENCE: 191
aauguccagc uaaauuagut t                                              21

<210> SEQ ID NO 192
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 192
uccaaugucc agcuaaauut t                                              21

<210> SEQ ID NO 193
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 193
auccaauguc cagcuaaaut t                                              21

<210> SEQ ID NO 194
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 194
gaauccaaug uccagcuaat t                                              21

<210> SEQ ID NO 195
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 195
uccccaaucu uuuucaaaat t                                              21

<210> SEQ ID NO 196
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

<223> OTHER INFORMATION: Description of Artificial Sequence: Synthetic
      oligonucleotide

<400> SEQUENCE: 196
cuccccaauc uuuuucaaat t                                              21

<210> SEQ ID NO 197
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 197 cucucccaa ucuuuuucat t                                               21

<210> SEQ ID NO 198
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 198 ccucuccca aucuuuuuct t                                               21

<210> SEQ ID NO 199
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 199
aagaucugaa guguucauat t                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 200
gaagaucuga aguguucaut t                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide <220> FEATURE:
<223> OTHER INFORMATION: Description of Artificial Sequence: Synthetic
      oligonucleotide

<400> SEQUENCE: 201
uguuaacaac ccaagggcat t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 202
auguuaacaa cccaagggct t                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 203
uucaccuaug aaugcuauat t                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 204
cuucaccuau gaaugcuaut t                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 205
ccuucaccua ugaaugcuat t                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Combined DNA/RNA Molecule:

Synthetic oligonucleotide
<220> FEATURE:
<223> OTHER INFORMATION: Description of Artificial Sequence: Synthetic
      oligonucleotide

<400> SEQUENCE: 206
ugcuccuuca ccuaugaaut t                                                21

<210> SEQ ID NO 207
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 207
uaaacuauga ucauugcaat t                                                21

<210> SEQ ID NO 208
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 208
guaaacuaug aucauugcat t                                                21

<210> SEQ ID NO 209
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 209
gguaaacuau gaucauugct t                                                21

<210> SEQ ID NO 210
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 210
agguaaacua ugaucauugt t                                                21

<210> SEQ ID NO 211
<211> LENGTH: 21
<212> TYPE: DNA
<213> ORGANISM: Artificial Sequence
<220> FEATURE:

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 211
uagguaaacu augaucauut t                                             21

<210> SEQ ID NO 212
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 212
auagguaaac uaugaucaut t                                             21

<210> SEQ ID NO 213
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 213
caauagguaa acuaugauct t                                             21

<210> SEQ ID NO 214
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 214
ucaauaggua aacuaugaut t                                             21

<210> SEQ ID NO 215
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 215
cucaauaggu aaacuaugat t                                             21

<210> SEQ ID NO 216
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 216
acucaauagg uaaacuaugt t                                              21

<210> SEQ ID NO 217
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 217
aacucaauag guaaacuaut t                                              21

<210> SEQ ID NO 218
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence:
      Synthetic oligonucleotide

<400> SEQUENCE: 218
uauguaaaua agaccaaugt t                                              21

<210> SEQ ID NO 219
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence:
      Synthetic oligonucleotide

<400> SEQUENCE: 219
uauauguaaa uaagaccaat t                                              21

<210> SEQ ID NO 220
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 220
uuauauguaa auaagaccat t                                              21

<210> SEQ ID NO 221
<211> LENGTH: 21
<212> TYPE: DNA
```

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 221
uuuauaugua aauaagacct t                                              21

<210> SEQ ID NO 222
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 222
aucaucuuga gcaugauaut t                                              21

<210> SEQ ID NO 223
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 223
uaucaucuug agcaugauat t                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 224
uaauuugaaa ucaauaucat t                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 225
cuauuguaag gacuaaguat t                                              21

<210> SEQ ID NO 226
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 226
gaccuauugu aaggacuaat t                                             21

<210> SEQ ID NO 227
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 227
ggaccuauug uaaggacuat t                                             21

<210> SEQ ID NO 228
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 228
acguccagcu auagaauaut t                                             21

<210> SEQ ID NO 229
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 229
uacguccagc uauagaauat t                                             21

<210> SEQ ID NO 230
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 230
uuacguccag cuauagaaut t                                             21

<210> SEQ ID NO 231
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 231
aaauuccuag aaucaauaat t                                              21

<210> SEQ ID NO 232
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 232
aauuccuaga aucaauaaat t                                              21

<210> SEQ ID NO 233
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 233
uuccuagaau caauaaaggt t                                              21

<210> SEQ ID NO 234
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 234
uccuagaauc aauaaagggt t                                              21

<210> SEQ ID NO 235
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 235
cuagaaucaa uaagggcat t                                               21
```

```
<210> SEQ ID NO 236
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 236
acauuugaua acaaugaagt t                                             21

<210> SEQ ID NO 237
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 237
cauuugauaa caaugaagat t                                             21

<210> SEQ ID NO 238
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 238
auuugauaac aaugaagaat t                                             21

<210> SEQ ID NO 239
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 239
uuugauaaca augaagaagt t                                             21

<210> SEQ ID NO 240
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 240
aagugaaaua cuaggaaugt t                                             21
```

```
<210> SEQ ID NO 241
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 241
agugaaauac uaggaaugct t                                              21

<210> SEQ ID NO 242
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 242
gugaaauacu aggaaugcut t                                              21

<210> SEQ ID NO 243
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 243
ugaaauacua ggaaugcuut t                                              21

<210> SEQ ID NO 244
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 244
gaaauacuag gaaugcuuct t                                              21

<210> SEQ ID NO 245
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 245
aaauacuagg aaugcuucat t                                              21
```

<210> SEQ ID NO 246
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 246
gaagcauuaa ugaccaaugt t                                              21

<210> SEQ ID NO 247
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 247
aagcauuaau gaccaaugat t                                              21

<210> SEQ ID NO 248
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 248
cgauaauaua acagcaagat st                                             22

<210> SEQ ID NO 249
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 249
cgauuauauu acaggaugat st                                             22

<210> SEQ ID NO 250
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 250
uuauugauuc uaggaauuut t                    21

<210> SEQ ID NO 251
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 251
uuuauugauu cuaggaauut t                    21

<210> SEQ ID NO 252
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 252
ccuuuauuga uucuaggaat t                    21

<210> SEQ ID NO 253
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 253
cccuuuauug auucuaggat t                    21

<210> SEQ ID NO 254
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 254
ugcccuuuau ugauucuagt t                    21

<210> SEQ ID NO 255
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 255
cuucauuguu aucaaaugut t    21

<210> SEQ ID NO 256
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 256
ucuucauugu uaucaaaugt t    21

<210> SEQ ID NO 257
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 257
uucuucauug uuaucaaaut t    21

<210> SEQ ID NO 258
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 258
cuucuucauu guuaucaaat t    21

<210> SEQ ID NO 259
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 259 cauccuagu auuucacuut t    21

<210> SEQ ID NO 260
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 260
gcauuccuag uauuucacut t                                              21

<210> SEQ ID NO 261
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 261
agcauuccua guauuucact t                                              21

<210> SEQ ID NO 262
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 262
aagcauuccu aguauuucat t                                              21

<210> SEQ ID NO 263
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 263
gaagcauucc uaguauuuct t                                              21

<210> SEQ ID NO 264
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 264
ugaagcauuc cuaguauuut t                                              21

<210> SEQ ID NO 265
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 265
cauuggucau uaaugcuuct t                                              21

<210> SEQ ID NO 266
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 266
ucauugguca uuaaugcuut t                                              21

<210> SEQ ID NO 267
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 267
ucuugcuguu auauuaucgt st                                             22

<210> SEQ ID NO 268
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 268
ucauccugua auauaaucgt st                                             22

<210> SEQ ID NO 269
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 269
cucuuagcaa agucaaguut t                                              21

<210> SEQ ID NO 270
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
``` oligonucleotide

<400> SEQUENCE: 270
cugucaucca gcaaauacat t                                              21

<210> SEQ ID NO 271
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 271
ugucauccag caaauacact t                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 272
uaauagguau guuauaugct t                                              21

<210> SEQ ID NO 273
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 273
auugagauag aaucuagaat t                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 274
auucuaccau auauugaact t                                              21

<210> SEQ ID NO 275
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

<223> OTHER INFORMATION: Description of Artificial Sequence: Synthetic
      oligonucleotide

<400> SEQUENCE: 275
uucuaccaua uauugaacat t                                            21

<210> SEQ ID NO 276
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 276
ucuaccauau auugaacaat t                                            21

<210> SEQ ID NO 277
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 277
aacuugacuu ugcuaagagt t                                            21

<210> SEQ ID NO 278
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 278
uguauuugcu ggaugacagt t                                            21

<210> SEQ ID NO 279
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 279
guguauuugc uggaugacat t                                            21

<210> SEQ ID NO 280
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide

```
<220> FEATURE:
<223> OTHER INFORMATION: Description of Artificial Sequence: Synthetic
      oligonucleotide

<400> SEQUENCE: 280
gcauauaaca uaccuauuat t                                              21

<210> SEQ ID NO 281
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 281
uucuagauuc uaucucaaut t                                              21

<210> SEQ ID NO 282
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 282
guucaauaua ugguagaaut t                                              21

<210> SEQ ID NO 283
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 283
uguucaauau auggagaat t                                               21

<210> SEQ ID NO 284
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 284
uuguucaaua uauggaugat t                                              21

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
              primer

<400> SEQUENCE: 285
agaaaacttg atgaaagaca                                              20

<210> SEQ ID NO 286
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
accataggca ttcataaa                                                18

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
gucaucacac ugaauaccaa u                                            21

<210> SEQ ID NO 288
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
auugguauuc agugugauga cac                                          23

<210> SEQ ID NO 289
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
cuacacaaau cagcgauuuc caugu                                        25

<210> SEQ ID NO 290
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
acauggaaau cgcugauuug uguag                                        25

<210> SEQ ID NO 291
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 291
ggcucuaagc uaacugaagt t                                              21

<210> SEQ ID NO 292
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 292
cuucaguuag cuuagagcct t                                              21

<210> SEQ ID NO 293
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
cgacuggagc acgaggacac ugacauggac ugaaggagua gaaa                     44

<210> SEQ ID NO 294
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
ctcaaagctc tacatcatta tc                                             22

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
cgactggagc acgaggacac tga                                            23

<210> SEQ ID NO 296
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
ccactccatt tgcttttaca tgatatcc                                       28

<210> SEQ ID NO 297
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
ggacactgac atggactgaa ggagta                                          26

<210> SEQ ID NO 298
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
gcttttacat gatatcccgc atctctgag                                       29

<210> SEQ ID NO 299
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
ccgcgggttc tggcaatgat aatctcaac                                       29

<210> SEQ ID NO 300
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
gccgcgtgta taattcataa accttggtag                                      30

<210> SEQ ID NO 301
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
ggggccccgc ggccgcgcat taatagcaag agttaggaag                           40

<210> SEQ ID NO 302
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
ggcucuuagc aaagucaag                                                  19

<210> SEQ ID NO 303
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 303
ggcucuuagc aaaguuaag                                                  19

<210> SEQ ID NO 304
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ggcucuuagc aaggucaag                                                  19

<210> SEQ ID NO 305
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
cuugacuuug cuaagagcc                                                  19

<210> SEQ ID NO 306
<211> LENGTH: 62
<212> TYPE: DNA
<213> ORGANISM: Homo sapiens

<400> SEQUENCE: 306
ttgatctttg ttgagtgtat cattcaactt gactttgcta agagccattg ttgtatttgc     60
cc                                                                    62

<210> SEQ ID NO 307
<211> LENGTH: 62
<212> TYPE: DNA
<213> ORGANISM: Homo sapiens

<400> SEQUENCE: 307
ctgatcctta tttaatgtat catttaactt gactttgcta agagccatcg ttgtatttgc     60
cc                                                                    62

<210> SEQ ID NO 308
<211> LENGTH: 62
<212> TYPE: DNA
<213> ORGANISM: Homo sapiens
<220> FEATURE:
<221> NAME/KEY: modified_base
<222> LOCATION: (51)..(51)
<223> OTHER INFORMATION: a, c, g, t, unknown or other

<400> SEQUENCE: 308
ttgatctttg ttgagtgtat cattcaactt gactttgcta agagccatcg ntgtatttgc     60
cc                                                                    62

<210> SEQ ID NO 309
<211> LENGTH: 62
<212> TYPE: DNA
```

<213> ORGANISM: Homo sapiens

<400> SEQUENCE: 309
ttgatctttg ttgagtgtat cgttcaactt gactttgcta agagccattg ttgtatttgc    60
cc                                                                  62

<210> SEQ ID NO 310
<211> LENGTH: 62
<212> TYPE: DNA
<213> ORGANISM: Homo sapiens
<220> FEATURE:
<221> NAME/KEY: modified_base
<222> LOCATION: (1)..(1)
<223> OTHER INFORMATION: a, c, g, t, unknown or other
<220> FEATURE:
<221> NAME/KEY: modified_base
<222> LOCATION: (7)..(7)
<223> OTHER INFORMATION: a, c, g, t, unknown or other
<220> FEATURE:
<221> NAME/KEY: modified_base
<222> LOCATION: (22)..(22)
<223> OTHER INFORMATION: a, c, g, t, unknown or other
<220> FEATURE:
<221> NAME/KEY: modified_base
<222> LOCATION: (49)..(49)
<223> OTHER INFORMATION: a, c, g, t, unknown or other

<400> SEQUENCE: 310
ntgatcnttg ttgagtgtat cnttcaactt gactttgcta agagccatng ttgtatttgc    60
cc                                                                  62

<210> SEQ ID NO 311
<211> LENGTH: 62
<212> TYPE: DNA
<213> ORGANISM: Homo sapiens

<400> SEQUENCE: 311
ttgatctttg ttgagtgtat cgttcaactt gactttgcta agagccattg ttgtatttgc    60
cc                                                                  62

<210> SEQ ID NO 312
<211> LENGTH: 62
<212> TYPE: DNA
<213> ORGANISM: Artificial Sequence
<220> FEATURE:
<223> OTHER INFORMATION: Description of Artificial Sequence: Consensus
      oligonucleotide

<400> SEQUENCE: 312
ttgatctttg ttgagtgtat cgttcaactt gactttgcta agagccattg ttgtatttgc    60
cc                                                                  62

<210> SEQ ID NO 313
<211> LENGTH: 30
<212> TYPE: RNA
<213> ORGANISM: Homo sapiens

<400> SEQUENCE: 313
caacuugacu uugcuaagag ccauuguugu                                    30

<210> SEQ ID NO 314
<211> LENGTH: 30
<212> TYPE: RNA
<213> ORGANISM: Homo sapiens

```
<400> SEQUENCE: 314
caacuugacc uugcuaagag ccauuguugu                                                30
```

METHODS AND COMPOSITIONS FOR PREVENTION OR TREATMENT OF RSV INFECTION

STATEMENT OF RELATED APPLICATIONS

This application is a continuation of U.S. patent application Ser. No. 13/359,421 (allowed), filed Jan. 26, 2012, which is a continuation of U.S. patent application Ser. No. 12/335,467 (abandoned), filed Dec. 15, 2008, which claims the benefit of U.S. Provisional Application No. 61/013,428, filed Dec. 13, 2007; U.S. Provisional Application No. 61/014,887, filed Dec. 19, 2007; U.S. Provisional Application No. 61/021,309, filed Jan. 15, 2008; U.S. Provisional Application No. 61/034,084, filed Mar. 5, 2008; and U.S. Provisional Application No. 61/049,076, filed Apr. 30, 2008, the disclosure of each of which is hereby incorporated by reference in its entirety.

REFERENCE TO SEQUENCE LISTING

This application includes a Sequence Listing submitted electronically as a text file named 23324_Sequence_listing.txt, created on Feb. 28, 2013, with a size of 99,351 bytes. The sequence listing is incorporated by reference.

BACKGROUND

By virtue of its natural function the respiratory tract is exposed to a slew of airborne pathogens that cause a variety of respiratory ailments. Viral infection of the respiratory tract is the most common cause of infantile hospitalization in the developed world with an estimated 91,000 annual admissions in the US at a cost of $300 M. Human respiratory syncytial virus (RSV) and parainfluenza virus (PIV) are two major agents of respiratory illness; together, they infect the upper and lower respiratory tracts, leading to croup, pneumonia and bronchiolitis (Openshaw, P. J. M. Respir. Res. 3 (Suppl 1), S15-S20 (2002), Easton, A. J., et al., Clin. Microbiol. Rev. 17, 390-412 (2004)).

RSV alone infects up to 65% of all babies within the first year of life, and essentially all within the first 2 years. It is a significant cause of morbidity and mortality in the elderly as well. Immunity after RSV infection is neither complete nor lasting, and therefore, repeated infections occur in all age groups. Infants experiencing RSV bronchiolitis are more likely to develop wheezing and asthma later in life. Research for effective treatment and vaccine against RSV has been ongoing for nearly four decades with few successes (Openshaw, P. J. M. Respir. Res. 3 (Suppl 1), S15-S20 (2002), Maggon, K. et al, Rev. Med. Virol. 14, 149-168 (2004)).

Currently, no vaccine is clinically approved for RSV. Strains of RSV also exist for nonhuman animals such as the cattle, goat, pig and sheep, causing loss to agriculture and the dairy and meat industry (Easton, A. J., et al., Clin. Microbiol. Rev. 17, 390-412 (2004)).

Both RSV and PIV contain nonsegmented negative-strand RNA genomes and belong to the Paramyxoviridae family. A number of features of these viruses have contributed to the difficulties of prevention and therapy. The viral genomes mutate at a high rate due to the lack of a replicational proof-reading mechanism of the RNA genomes, presenting a significant challenge in designing a reliable vaccine or antiviral (Sullender, W. M. Clin. Microbiol. Rev. 13, 1-15 (2000)). Promising inhibitors of the RSV fusion protein (F) were abandoned partly because the virus developed resistant mutations that were mapped to the F gene (Razinkov, V., et. al., Antivir. Res. 55, 189-200 (2002), Morton, C. J. et al. Virology 311, 275-288 (2003)). Both viruses associate with cellular proteins, adding to the difficulty of obtaining cell-free viral material for vaccination (Burke, E., et al., Virology 252, 137-148 (1998), Burke, E., et al., J. Virol. 74, 669-675 (2000), Gupta, S., et al., J. Virol. 72, 2655-2662 (1998)). Finally, the immunology of both, and especially that of RSV, is exquisitely complex (Peebles, R. S., Jr., et al., Viral. Immunol. 16, 25-34 (2003), Haynes, L. M., et al., J. Virol. 77, 9831-9844 (2003)). Use of denatured RSV proteins as vaccines leads to "immunopotentiation" or vaccine-enhanced disease (Polack, F. P. et al. J. Exp. Med. 196, 859-865 (2002)). The overall problem is underscored by the recent closure of a number of anti-RSV biopharma programs.

The RSV genome comprises a single strand of negative sense RNA that is 15,222 nucleotides in length and yields eleven major proteins. (Falsey, A. R., and E. E. Walsh, 2000, Clinical Microbiological Reviews 13:371-84.) Two of these proteins, the F (fusion) and G (attachment) glycoproteins, are the major surface proteins and the most important for inducing protective immunity. The SH (small hydrophobic) protein, the M (matrix) protein, and the M2 (22 kDa) protein are associated with the viral envelope but do not induce a protective immune response. The N (major nucleocapsid associated protein), P (phosphoprotein), and L (major polymerase protein) proteins are found associated with virion RNA. The two non-structural proteins, NS1 and NS2, presumably participate in host-virus interaction but are not present in infectious virions.

Human RSV strains have been classified into two major groups, A and B. The G glycoprotein has been shown to be the most divergent among RSV proteins. Variability of the RSV G glycoprotein between and within the two RSV groups is believed to be important to the ability of RSV to cause yearly outbreaks of disease. The G glycoprotein comprises 289-299 amino acids (depending on RSV strain), and has an intracellular, transmembrane, and highly glycosylated stalk structure of 90 kDa, as well as heparin-binding domains. The glycoprotein exists in secreted and membrane-bound forms.

Successful methods of treating RSV infection are currently unavailable (Maggon K and S. Batik, 2004, Reviews in Medical Virology 14:149-68). Infection of the lower respiratory tract with RSV is a self-limiting condition in most cases. No definitive guidelines or criteria exist on how to treat or when to admit or discharge infants and children with the disease. Hypoxia, which can occur in association with RSV infection, can be treated with oxygen via a nasal cannula. Mechanical ventilation for children with respiratory failure, shock, or recurrent apnea can lower mortality. Some physicians prescribe steroids. However, several studies have shown that steroid therapy does not affect the clinical course of infants and children admitted to the hospital with bronchiolitis. Thus corticosteroids, alone or in combination with bronchodilators, may be useless in the management of bronchiolitis in otherwise healthy unventilated patients. In infants and children with underlying cardiopulmonary diseases, such as bronchopulmonary dysphasia and asthma, steroids have also been used.

Ribavirin, a guanosine analogue with antiviral activity, has been used to treat infants and children with RSV bronchiolitis since the mid 1980s, but many studies evaluating its use have shown conflicting results. In most centers, the use of ribavirin is now restricted to immunocompromised patients and to those who are severely ill.

The severity of RSV bronchiolitis has been associated with low serum retinol concentrations, but trials in hospitalized children with RSV bronchiolitis have shown that vitamin A supplementation provides no beneficial effect. Therapeutic trials of 1500 mg/kg intravenous RSV immune globulin or 100 mg/kg inhaled immune globulin for RSV lower-respiratory-tract infection have also failed to show substantial beneficial effects.

In developed countries, the treatment of RSV lower-respiratory-tract infection is generally limited to symptomatic therapy. Antiviral therapy is usually limited to life-threatening situations due to its high cost and to the lack of consensus on efficacy. In developing countries, oxygen is the main therapy (when available), and the only way to lower mortality is through prevention.

RNA interference or "RNAi" is a term initially coined by Fire and co-workers to describe the observation that double-stranded RNA (dsRNA) can block gene expression when it is introduced into worms (Fire et al., *Nature* 391:806-811, 1998). Short dsRNA directs gene-specific, post-transcriptional silencing in many organisms, including vertebrates, and has provided a new tool for studying gene function. RNAi has been suggested as a method of developing a new class of therapeutic agents. However, to date, these have remained mostly as suggestions with no demonstrate proof that RNAi can be used therapeutically.

Therefore, there is a need for safe and effective vaccines against RSV, especially for infants and children. There is also a need for therapeutic agents and methods for treating RSV infection at all ages and in immuno-compromised individuals. There is also a need for scientific methods to characterize the protective immune response to RSV so that the pathogenesis of the disease can be studied, and screening for therapeutic agents and vaccines can be facilitated. The present invention overcomes previous shortcomings in the art by providing methods and compositions effective for modulating or preventing RSV infection. Specifically, the present invention advances the art by providing iRNA agents that have been shown to reduce RSV levels in vitro and in vivo, as well as being effective against both major subtypes of RSV, and a showing of therapeutic activity of this class of molecules.

SUMMARY

The present invention is based on the in vitro and in vivo demonstration that RSV can be inhibited through intranasal administration of iRNA agents, as well as by parenteral administration of such agents, and the identification of potent iRNA agents from the P, N and L gene of RSV that can reduce RNA levels with both the A and B subtype of RSV. Based on these findings, the present invention provides specific compositions and methods that are useful in reducing RSV mRNA levels, RSV protein levels and RSV viral titers in a subject, e.g., a mammal, such as a human. It is shown herein that administration of multiple doses of an siRNA agent over a course of days can provide improved results. E.g., in a preferred embodiment a preselected amount of siRNA agent results in better inhibition of gene expression when administered as fractional doses over the course of more than one day.

In one aspect, the invention provides for an siRNA composition that comprises a therapeutically effective amount of ALN-RSV01. ALN-RSV01 is an siRNA agent with the sense strand sequence (5' to 3') GGCUCUUAGCAAAGU-CAAGdTdT (SEQ ID NO: 1) and the antisense strand sequence (5' to 3') CUUGACUUUGCUAAGAGCCdTdT (SEQ ID NO: 2). ALN-RSV01 is the same as AL-DP-2017, and the terms are used herein interchangeably. The structure of AL-DP-2017 (i.e., ALN-RSV01) and details about its manufacture are fully described in co-owned U.S. Provisional Application No. 61/021,309 filed on Jan. 15, 2008, which is herein incorporated by reference in its entirety, for all purposes.

In one embodiment the invention provides for a lyophilized powder. In another embodiment the invention provides for a liquid solution, and in another embodiment a liquid suspension, and in another embodiment a dry powder comprising said amount of ALN-RSV01. In one embodiment, the therapeutically effective amount of ALN-RSV01 is less than or equal to 150 mg of anhydrous oligonucleotide. In another embodiment, the therapeutically effective amount is equal to 150 mg of anhydrous oligonucleotide. In another embodiment, the therapeutically effective amount is equal to 75 mg of anhydrous oligonucleotide. In one embodiment, administration of the therapeutically effective amount to a human subject produces in the subject no significant increase in the subject's white cell count. In another embodiment, administration of the therapeutically effective amount to a human subject produces in the concentration in a subject's inflammatory cytokine(s). In one embodiment those cytokine(s) are one or more of CRP, G-CSF, IL1-RA, or TNF.

In one related embodiment, the liquid solution is formulated to have an osmolality ranging from 200-400 mOsm/kg. In certain embodiments, the liquid solution is a buffered. In certain embodiments, the pH of the liquid solution is between 5 and 8. In other embodiments, the pH of the liquid solution is between 5.6 and 7.6. In related embodiments, the liquid solution comprises a sodium phosphate buffer. In still other embodiments, the concentration of the buffer is between 10 and 100 mM, between 20 and 80 mM, between 30 and 70 mM, between 40 and 60 mM, or equal to or about 50 mM. In yet another embodiment, the pH of the buffered solution is 6.6.

In one embodiment of the invention, the administration of the therapeutically effective amount of ALN-RSV01 to a human subject produces in said subject no significant increase in a white cell count. In another embodiment, the administration of said therapeutically effective amount to a human subject produces in said subject no significant elevation in a CRP concentration, a G-CSF concentration, an IL1-RA concentration or a TNF concentration. In a related embodiment, the siRNA composition further comprises a modification for protection from an exonuclease. In another embodiment, the modification of the siRNA composition is selected from the group consisting of a phosphorothioate and a hydroxy pyrollidine (hp) linker.

In another embodiment, the therapeutic ALN-RSV01 composition is administered topically. In related embodiments, the topical administration is intranasal or intrapulmonary, e.g., administration occurs by inhalation of said composition. In still other related embodiments, the patient administers the composition to himself or herself, or a third party (e.g., a guardian or a healthcare practitioner such as a doctor) can administer the composition to the patient. In certain embodiments, the composition is administered as an aerosolized liquid, e.g., a nasal spray. The nasal spray can be administered a Becton-Dickinson Accuspray™ nasal spray system or an equivalent thereof. In related embodiments, the aerosolized liquid is produced by a nebulizer. In still other related embodiments, 0.1 ml to 0.6 ml (e.g., 0.1, 0.2, 0.3, 0.4, 0.5, or 0.6 ml) of the aerosolized liquid comprising ALN-RSV01 is administered to each nostril. A plurality of doses can be administered daily, where a plurality includes two, three, four, or five doses. In related embodiments, the administering of the plurality of doses reduces RSV protein, mRNA, or titer in a cell of the respiratory tract of said human to at least the same level as an administering of a single dose that equals the dose provided by said plurality of doses. In yet other related embodiments, the administering of said plurality of doses by inhalation delivers a total dose of between 0.1 and 0.6 mg/kg of anhydrous oligonucleotide to said human.

In certain embodiments, the first of said plurality of doses is administered before the human patient is infected with RSV (e.g., prophylactically).

In yet another embodiment, the invention provides a method of identifying a compound that is effective in preventing or treating RSV infection comprising: providing a first human infected with RSV strain Memphis-37 wherein said first human exhibits a reduction in lung function during progression of RSV infection; administering to a said first human a test compound, wherein said administering occurs either before or after RSV infection; assessing progression of the RSV infection in said first human; comparing progression of RSV infection in the first human to progression of RSV infection in at least one second human that has not been administered said test compound; identifying the test compound as a compound that is effective in preventing or treating RSV infection if progression in the first human subject is reduced compared to progression in the second human. In a related embodiment, the method further comprises recording or reporting said identification of the test compound. In yet another related embodiment, the screening method comprises administering the test compound to a third human if progression in the first human subject is reduced compared to progression in the second human.

In one embodiment of the invention, a method is described for preventing or treating a Respiratory Syncytial Virus (RSV) infection in a human lung transplant recipient, including administering to the human lung transplant recipient a composition including a therapeutically effective amount of ALN-RSV01. In one aspect, the composition is administered topically. In a related aspect, the topical administration is intranasal or intrapulmonary. In another related aspect, the topical administration is intranasal. In another related aspect, the topical administration is intrapulmonary. In a related aspect, the intrapulmonary administration is by inhalation of the composition. In another aspect, the composition is administered as an aerosol. In a related aspect, the aerosol is a nasal spray. In another related aspect, the aerosol is produced by a nebulizer. In a related aspect, the nebulizer is a PARI eFlow® 30 L nebulizer.

In another embodiment, the method includes administering a plurality of doses of the composition. In one aspect, one of the plurality of doses is administered daily. In another aspect, the plurality of doses is two or three doses. In another related aspect, the plurality of doses is three doses.

In another embodiment, the human lung transplant recipient is presently infected with RSV. In one aspect, the human lung transplant recipient is presently infected with RSV when the first of the plurality of doses is administered. In a related aspect, the administering reduces RSV protein, RSV mRNA, RSV peak viral load, time to peak RSV viral load, duration of RSV viral shedding, RSV viral AUC, or RSV titer in a cell of the respiratory tract of the human lung transplant recipient.

In another embodiment, the administering of the plurality of doses reduces RSV protein, RSV mRNA, RSV peak viral load, time to peak RSV viral load, duration of RSV viral shedding, RSV viral AUC, or RSV titer in a cell of the respiratory tract of the human lung transplant recipient to at least the same level as an administering of a single dose that equals the dose provided by the plurality of doses. In one aspect, the administering of the plurality of doses is by inhalation and delivers a total dose of between 0.1 and 0.6 mg/kg of anhydrous oligonucleotide to the human lung transplant recipient.

In another embodiment, the method further includes determining the characteristics of RSV infection. In one aspect, the characteristics of RSV infection are determined by quantitative RT-PCR (qRT-PCR) analysis of a nasal swab sample and/or a sputum sample from the human lung transplant recipient. In a related aspect, the qRT-PCR is used to determine RSV mRNA, RSV peak viral load, time to peak RSV viral load, duration of RSV viral shedding, RSV viral AUC, or RSV titer.

In another embodiment, the human lung transplant recipient is receiving bronchodilator therapy. In a related aspect, the human lung transplant recipient is administered the composition within one hour of receiving bronchodilator therapy.

In another embodiment, the human lung transplant recipient is receiving standard of care treatment. In a related aspect, the standard of care treatment includes administration of ribavirin. In another aspect, the human lung transplant recipient is administered the composition one to two hours before administration of ribavirin.

In another embodiment, the administration of the composition to the human lung transplant recipient is started within seven days of onset of signs and/or symptoms of RSV infection. In one aspect, the signs and/or symptoms include a decrease in FEV1, fever, new onset rhinorrhea, sore throat, nasal congestion, cough, wheezing, headache, myalgia, chills, or shortness of breath.

In another embodiment, the aerosolized ALN-RSV01 is administered at a concentration of 0.6 mg/kg to the human lung transplant recipient by inhalation of the aerosolized ALN-RSV01 once daily for three days using a PARI eFlow® 30 L nebulizer.

In another embodiment, a method is described for reducing the risk of a medical condition in a human lung transplant recipient including preventing or treating a Respiratory Syncytial Virus (RSV) infection in a human lung transplant recipient by administering to the human lung transplant recipient a composition including a therapeutically effective amount of ALN-RSV01, wherein the medical condition is selected from the group consisting of acute rejection of transplanted lung, bronchilolitis obliterans syndrome, incidence of intubation, incidence of viral, bacterial, or fungal respiratory infection, and irreversible decline in lung function.

In another aspect, the invention provides a method of preventing or treating RSV infection by administering a composition that comprises a therapeutically effective amount of ALN-RSV01 to a human patient with a recurring cough that has lasted at least two days. In a related embodiment, the method of administrating ALN-RSV01 further comprising a step of diagnosing the human as suffering from a recurring cough lasting at least two days, wherein said diagnosis occurs prior to the administration of said composition and the human has a recurring cough that has lasted at least two days. In a related embodiment, the human is less than 18 years old, less than 2 years old, less than 6 months old, or less than 3 months old. In another related embodiment, the patient has a weakened immune system. In yet another related embodiment, the patient is dehydrated or at risk of becoming dehydrated. In still another embodiment, the patient is administered a dose of Synagis™ within 6 weeks of the administration of said composition.

In another aspect, the administration of a therapeutic dose of ALN-RSV01 takes less than 10 minutes, or more preferably five minutes or less.

In another aspect, the invention provides a method of preventing or treating RSV infection by administering a composition that comprises a therapeutically effective amount of ALN-RSV01 to a human patient, further comprising measuring ALN-RSV01-directed cleavage of RSV N gene mRNA in said human. In a related embodiment, the ALN-RSV01-directed cleavage is detected by PCR. In another related embodiment, the RSV N gene mRNA cleavage products are detected in nasal samples of said human. In yet another related embodiment, the RNAi-mediated cleavage is measured less than 5 days, or less than 3 days, after administering a dose of said composition. In yet another embodiment, the method further comprises a step of measuring the titer of RSV in said human.

The details of one or more embodiments of the invention are set forth in the accompanying drawings and the description below. Other features, objects, and advantages of the invention will be apparent from this description, the drawings, and from the claims.

BRIEF DESCRIPTION OF DRAWINGS AND TABLES

Figure 1:
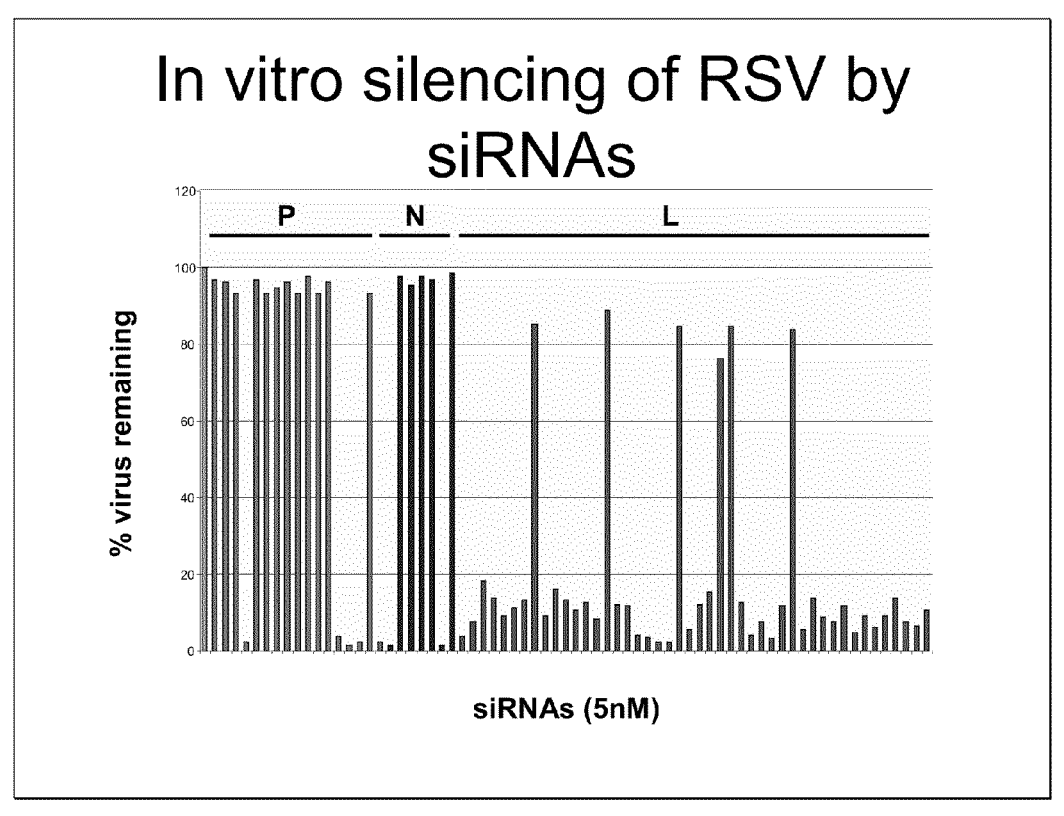

FIG. 1: In vitro inhibition of RSV using iRNA agents. iRNA agents provided in Table 1 (a-c) were tested for anti-RSV activity in a plaque formation assay as described in the Examples. Each column (bar) represents an iRNA agent provided in Table 1 (a-c), e.g., column 1 is the first agent in Table 1a, etc. Active iRNA agents were identified.

FIG. 2: In vitro dose response inhibition of RSV using iRNA agents. Examples of active agents from Table 1 were tested for anti-RSV activity in a plaque formation assay as described in the Examples at four concentrations. A dose dependent-response was found with active iRNA agents tested.

Figure 3:
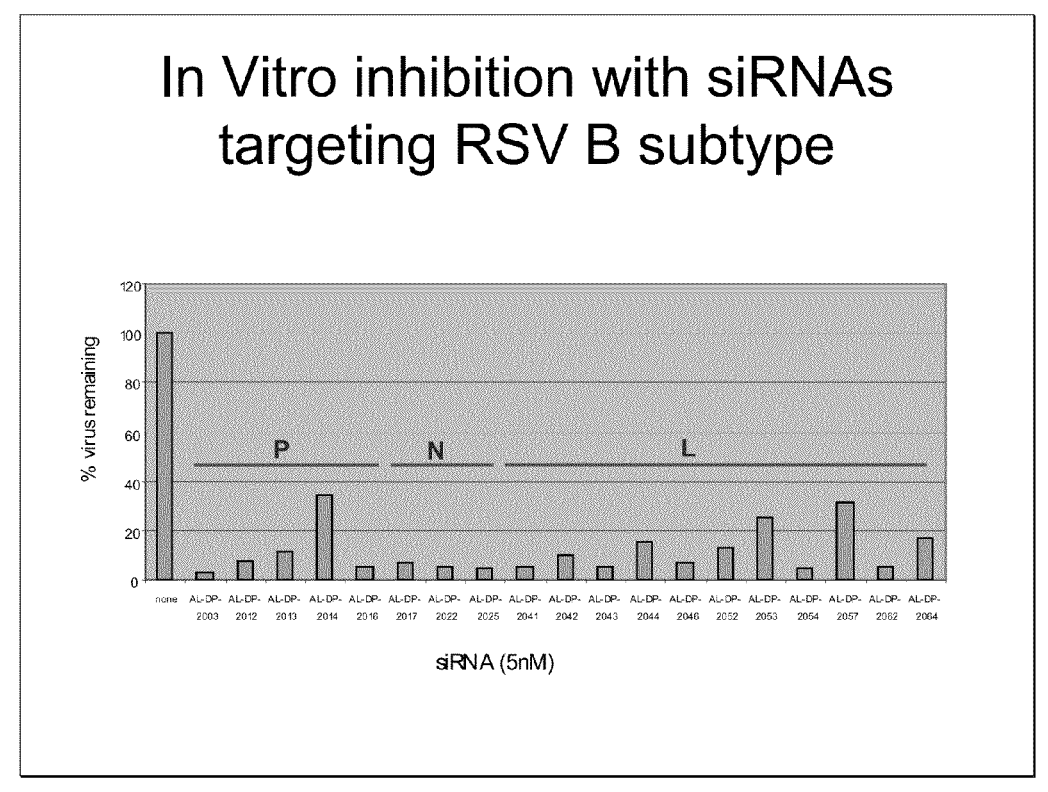

FIG. 3: In vitro inhibition of RSV B subtype using iRNA agents. iRNA agents provided in FIG. 2 were tested for anti-RSV activity against subtype B in a plaque formation assay as described in the Examples. Subtype B was inhibited by the iRNA agents tested.

Figure 4:
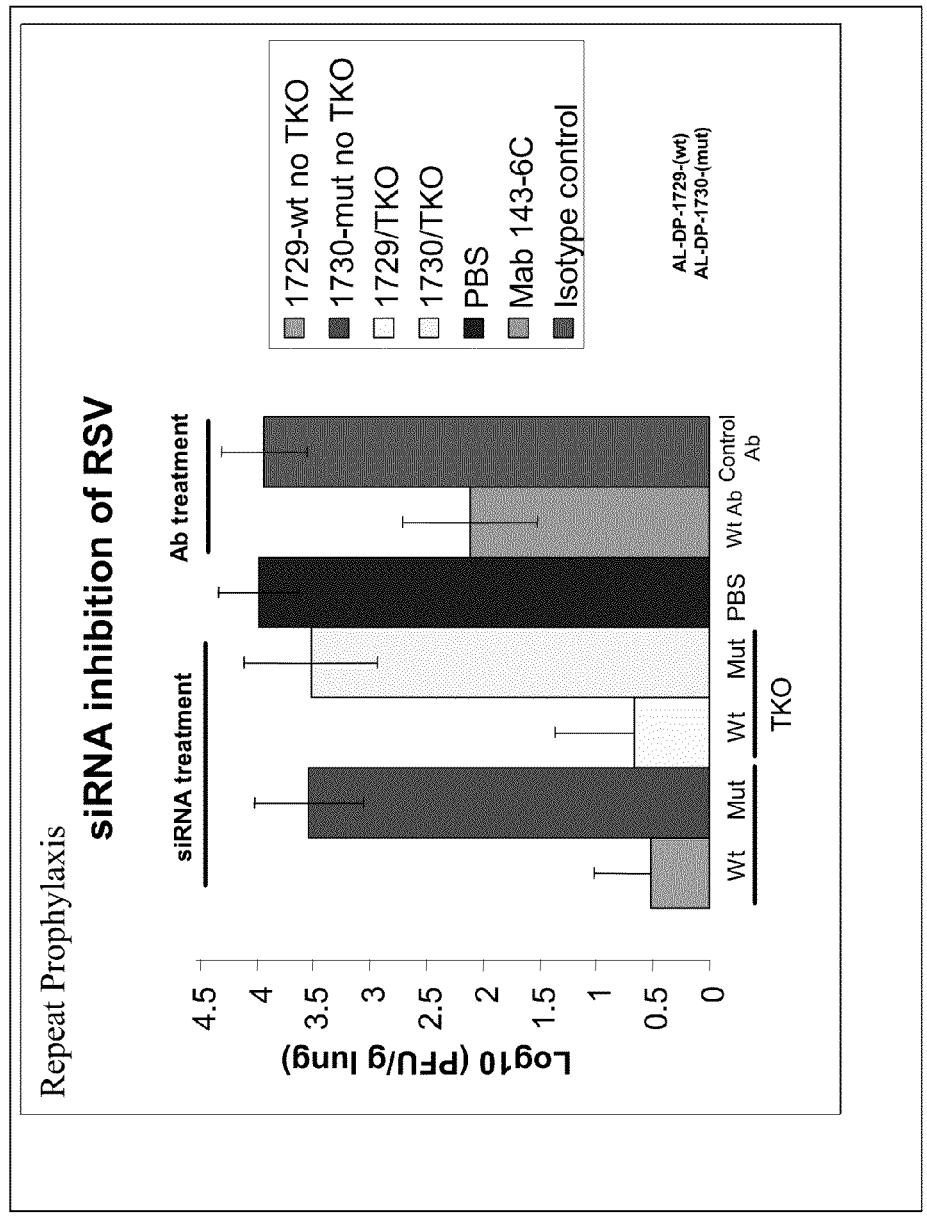

FIG. 4: In vivo inhibition of RSV using iRNA agents. Agents as described in the figure were tested for anti-RSV activity in a mouse model as described in the Examples. The iRNA agents were effective at reducing viral titers in vivo.

Figure 5:
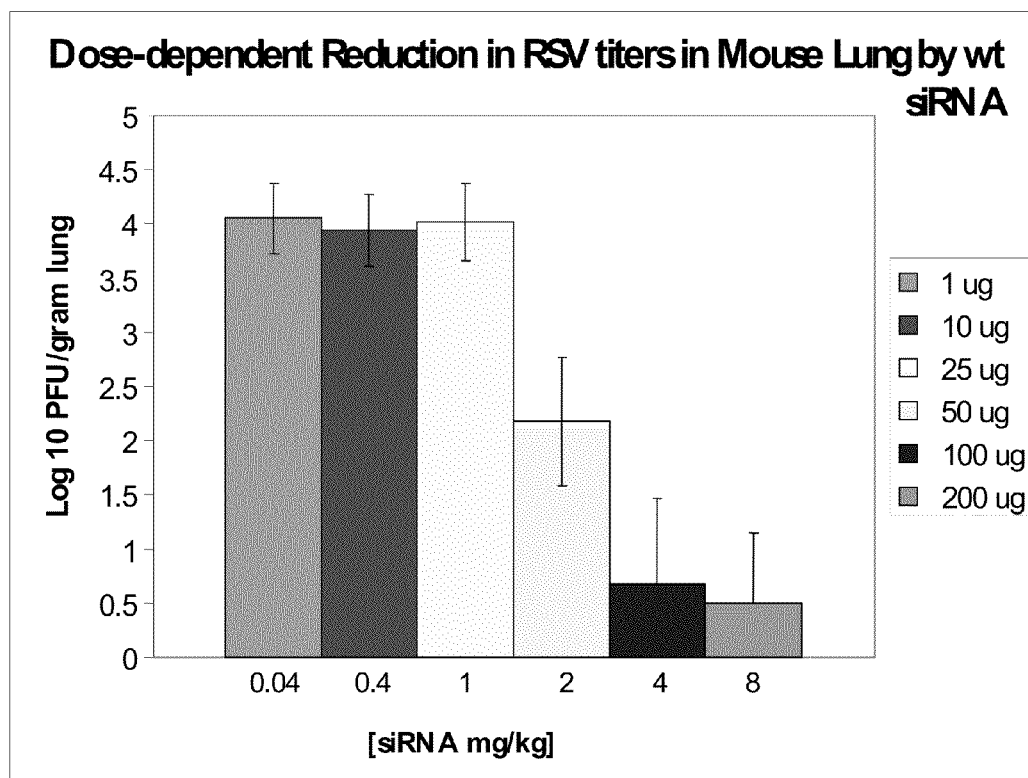

FIG. 5: In vivo inhibition of RSV using AL-DP-1730. AL-DP-1730 was tested for dose-dependent activity using the methods provided in the Examples. The agent showed a dose-dependent response.

Figure 6:
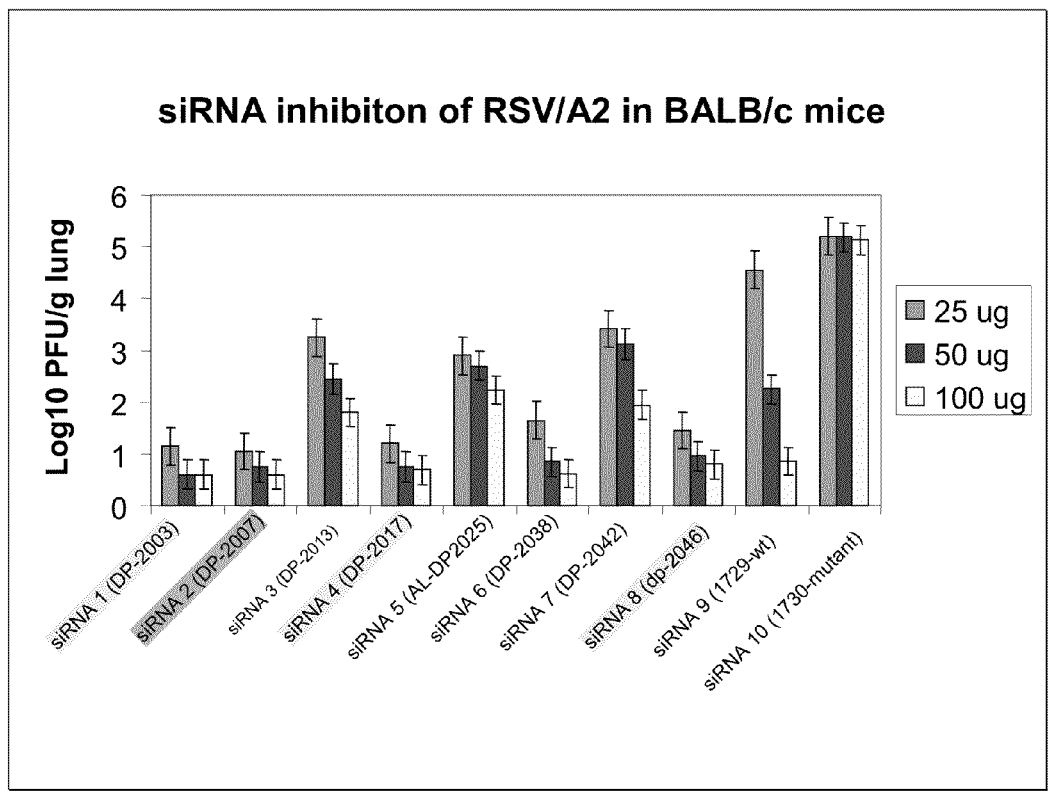

FIG. 6: In vivo inhibition of RSV using iRNA agents. iRNA agents described in the Figure were tested for anti-RSV activity in vivo as described in the Examples.

Figure 7:
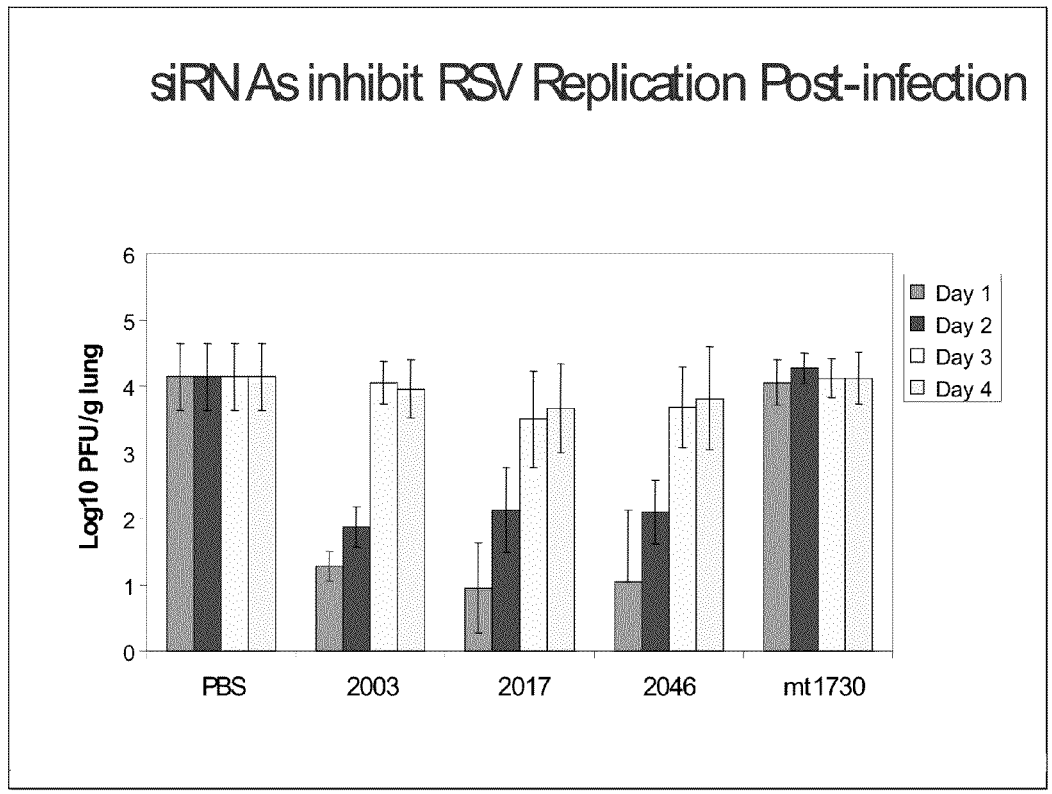

FIG. 7: In vivo inhibition of RSV using iRNA agents. iRNA agents described in the Figure were tested for anti-RSV activity in vivo as described in the Examples.

Figure 8:
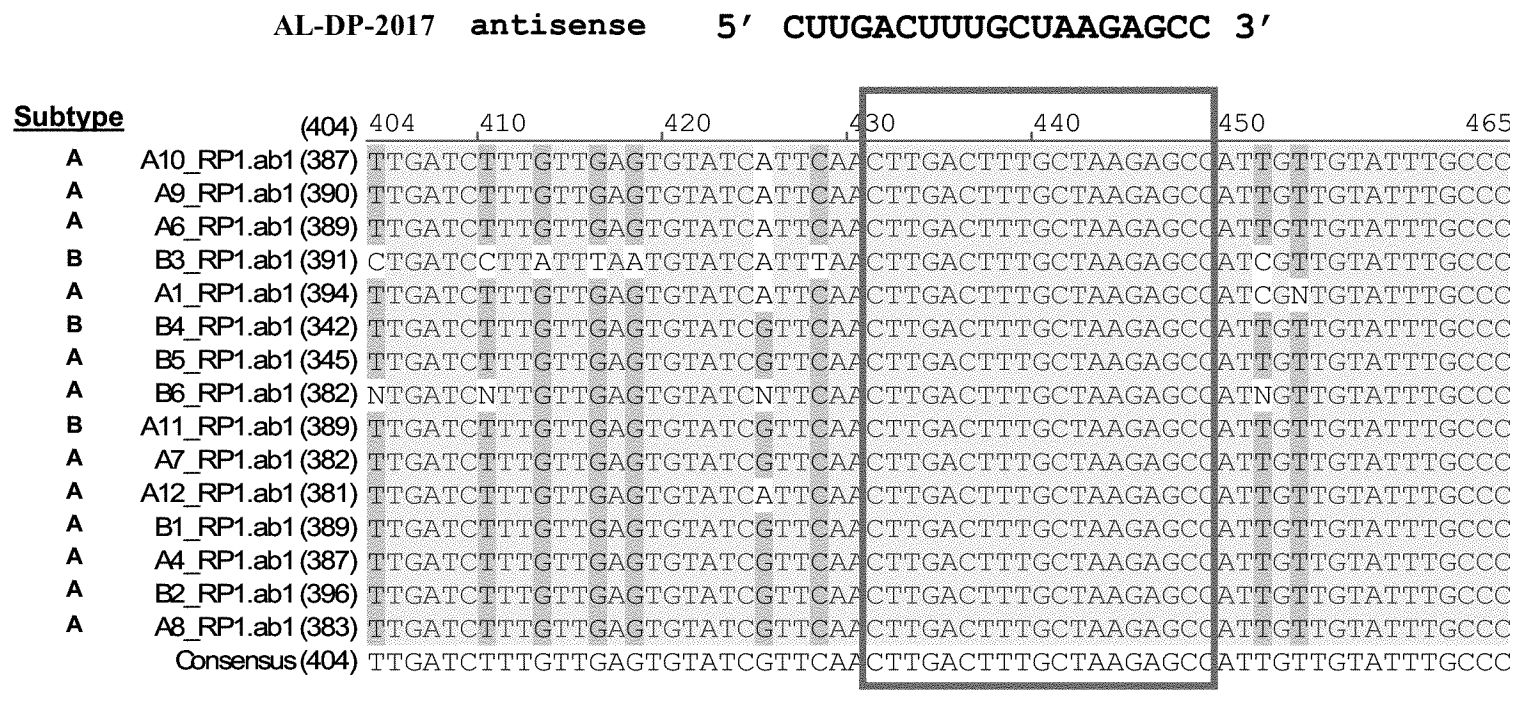

FIG. 8: Sequence analysis of RSV N genes from clinical isolates. FIG. 8 discloses SEQ ID NOS 305-306, 306, 306-309, 309-311, 311, 306, 311, 311, 309, 311 and 312, respectively, in order of appearance.

Figure 9:
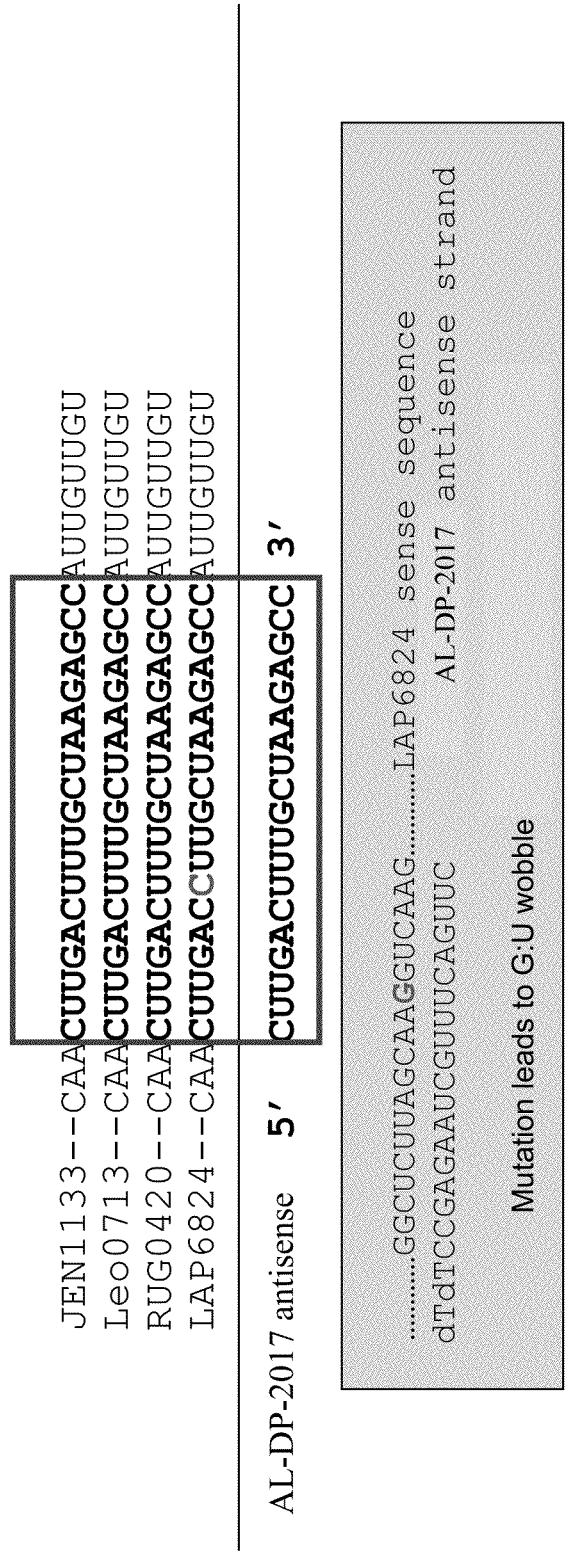

FIG. 9: Sequence analysis of RSV N genes from slower growing clinical RSV isolates showing single base mutation in ALN-RSV01 recognition site for isolate LAP6824. FIG. 9 discloses SEQ ID NOS 313, 313, 313-314, 305, 304 and 2, respectively, in order of appearance.

Figure 10:
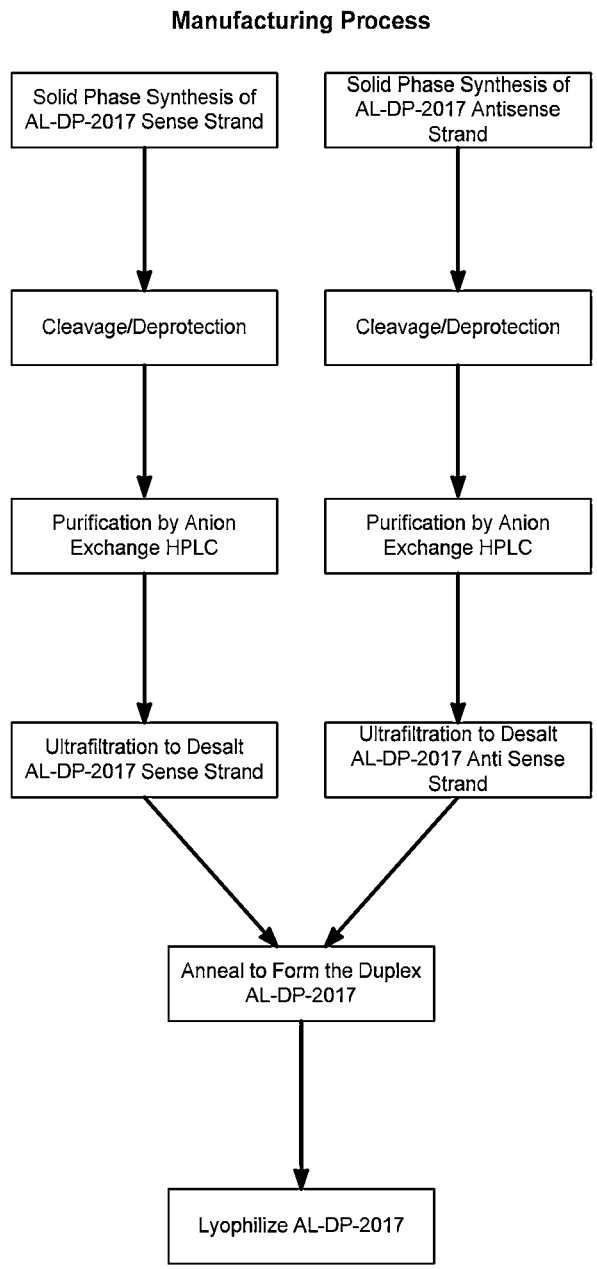

FIG. 10: Flow chart illustrating manufacturing process for ALN-RSV01 drug substance.

Figure 11:
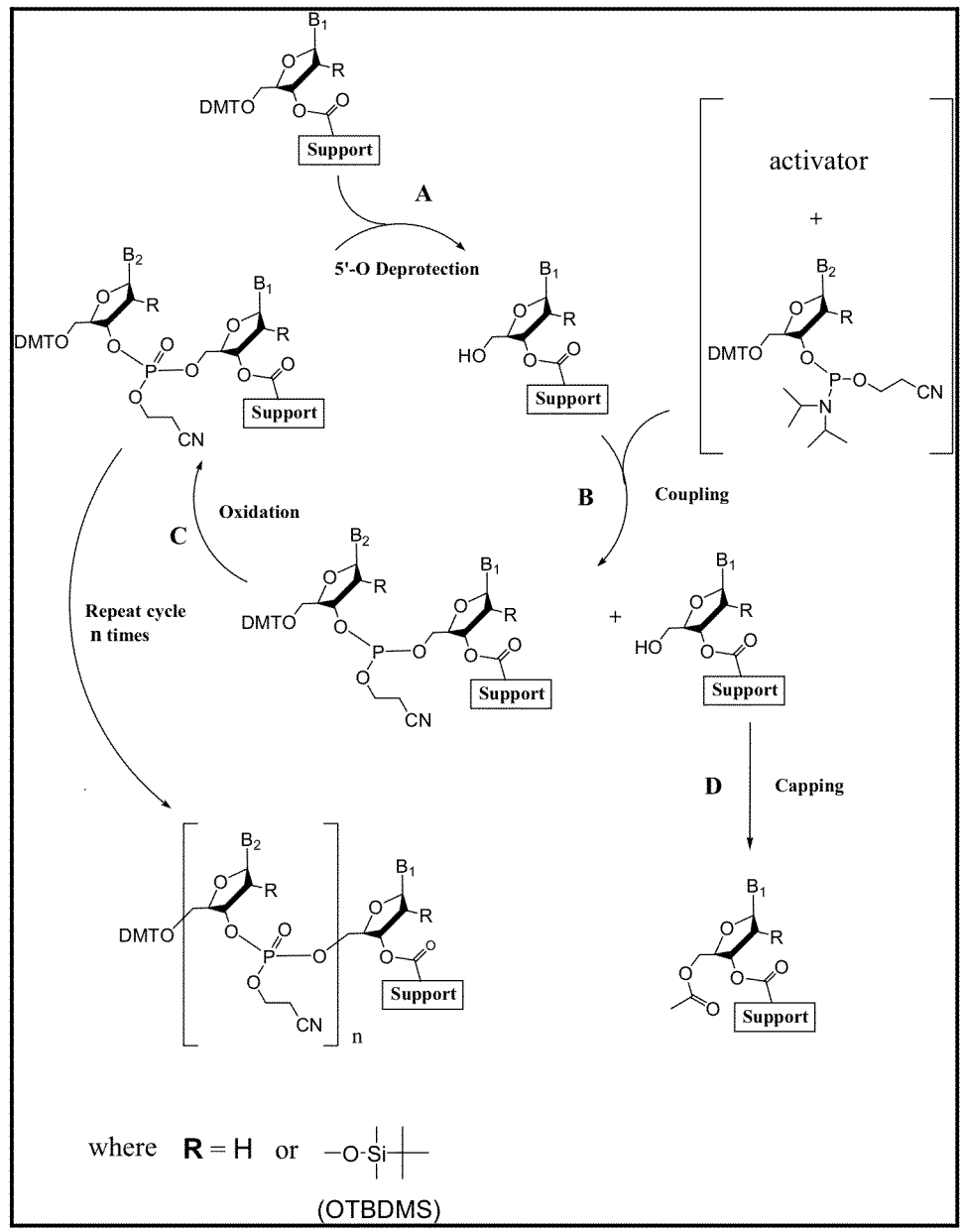

FIG. 11: Illustration of cycle of steps involved in solid-phase synthesis of ALN-RSV01 drug substance.

Figure 12:
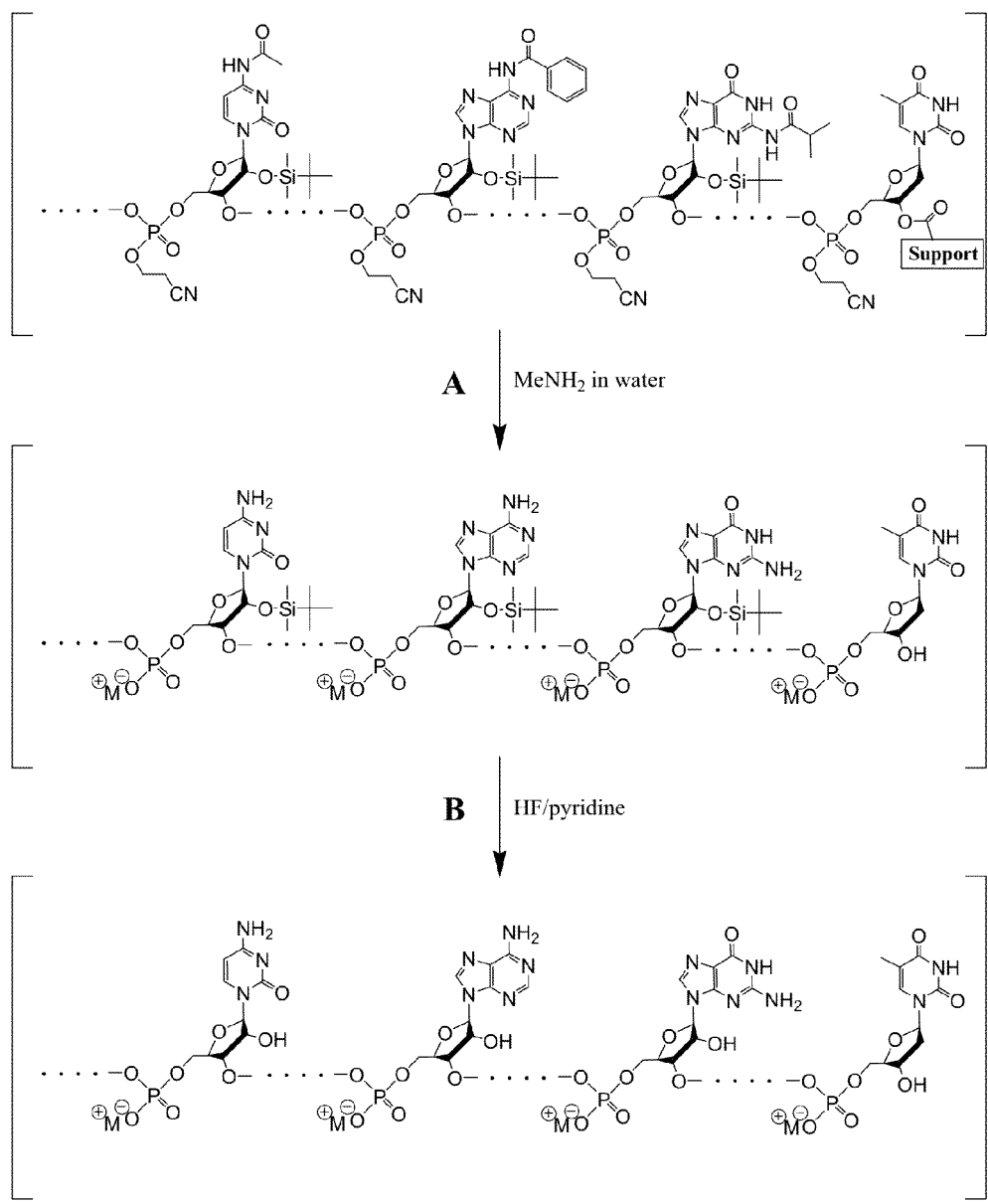

FIG. 12: Illustration of cleavage and deprotection reactions following solid-phase synthesis of ALN-RSV01 drug substance.

Figure 13A:
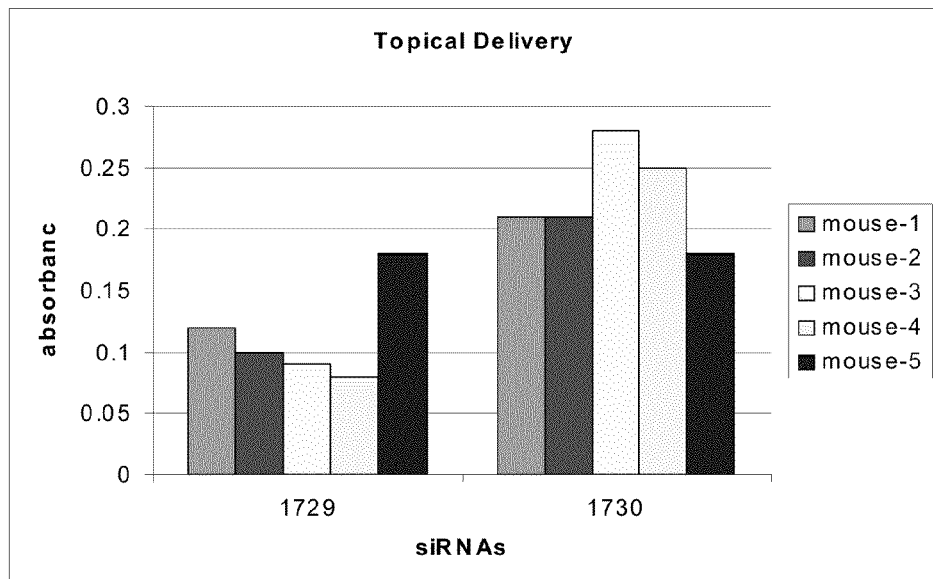
Figure 13B:
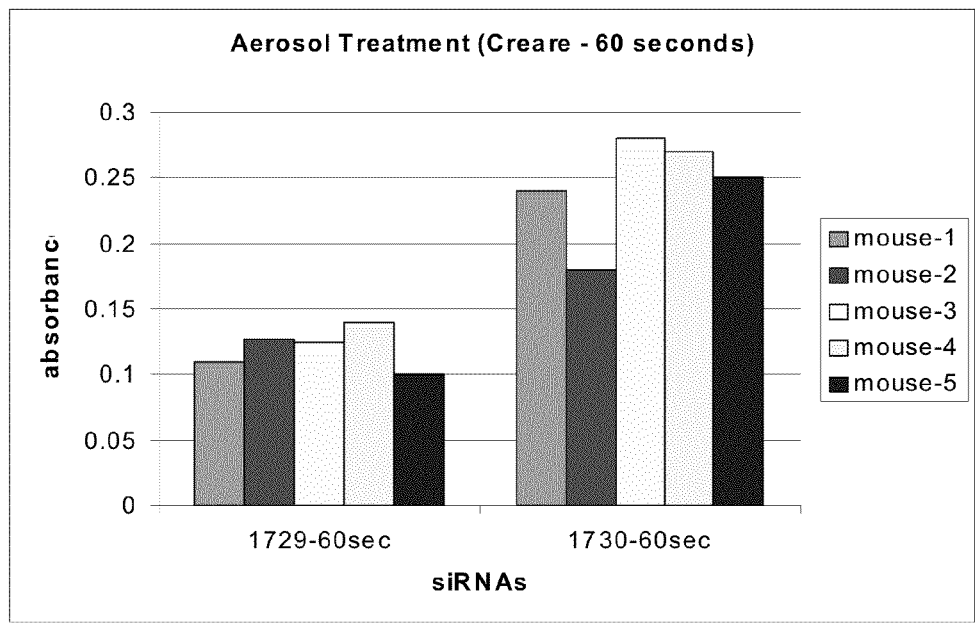

FIG. 13A and FIG. 13B: In vivo inhibition of RSV using iRNA agents delivered via aerosol. iRNA agents described in the Figure were tested for anti-RSV activity in vivo as described in the Example.

Figure 14:
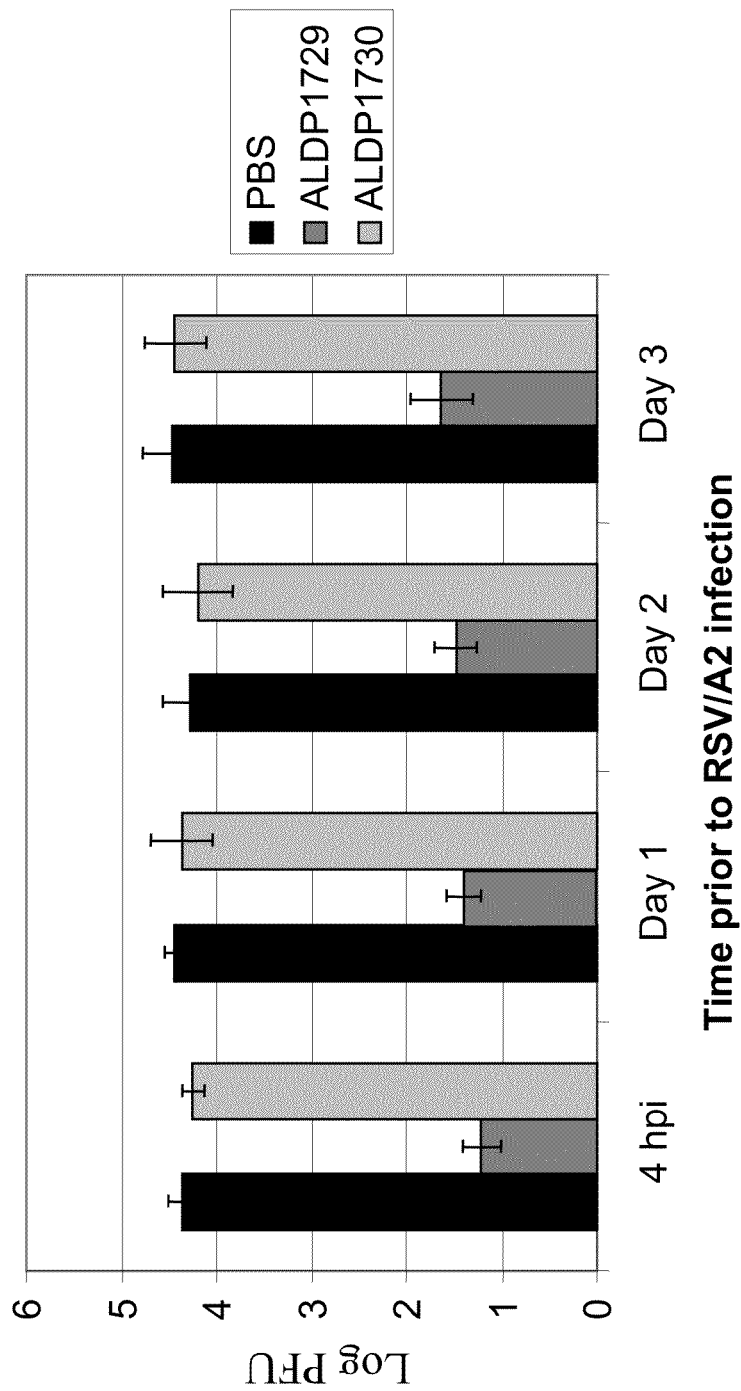

FIG. 14: In vivo protection against RSV infection using iRNA agents. iRNA agents described in the Figure were tested prior to RSV challenge to test for protective activity.

Figure 15:
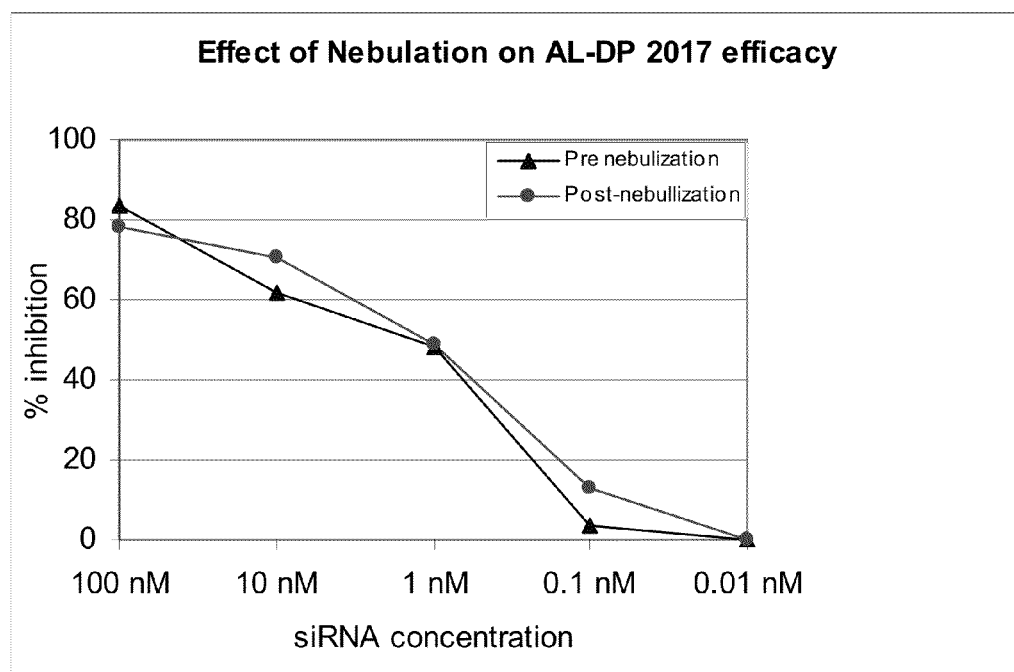

FIG. 15: In vitro activity of nebulized iRNA agent. iRNA agent as described was nebulized and shown to retain activity in an in vitro assay of RSV infection.

Figure 16:
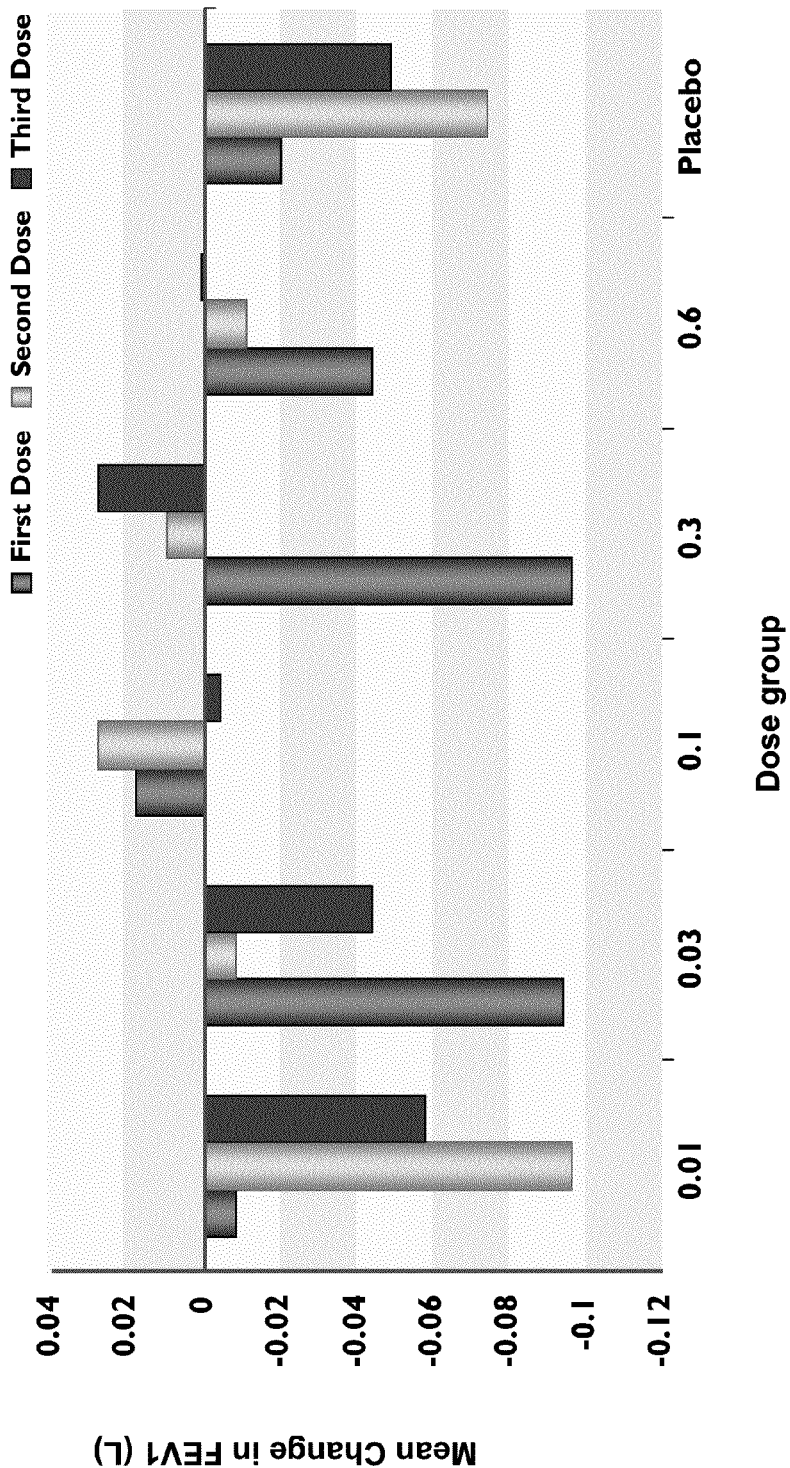

FIG. 16: Lung function (FEV1 (L)) 30 minutes post-dose in human subjects after inhalation of siRNA ALN-RSV01 targeting RSV. Dose in mg/kg (assuming average human weight of 70 kg).

Figure 17:
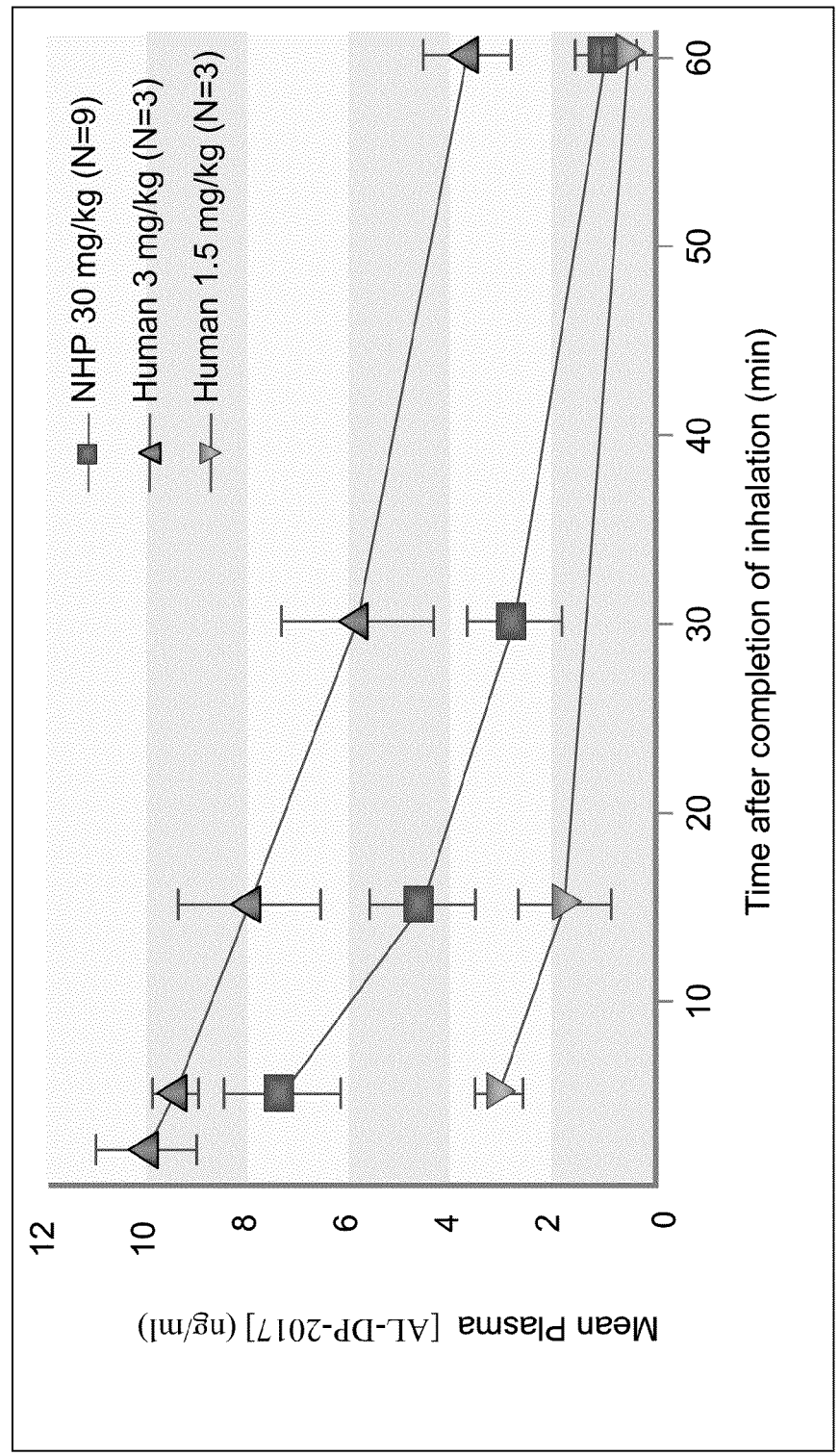

FIG. 17: Mean plasma level of siRNA ALN-RSV01 targeting RSV in man vs. non human primates after inhalation.

Figure 18:
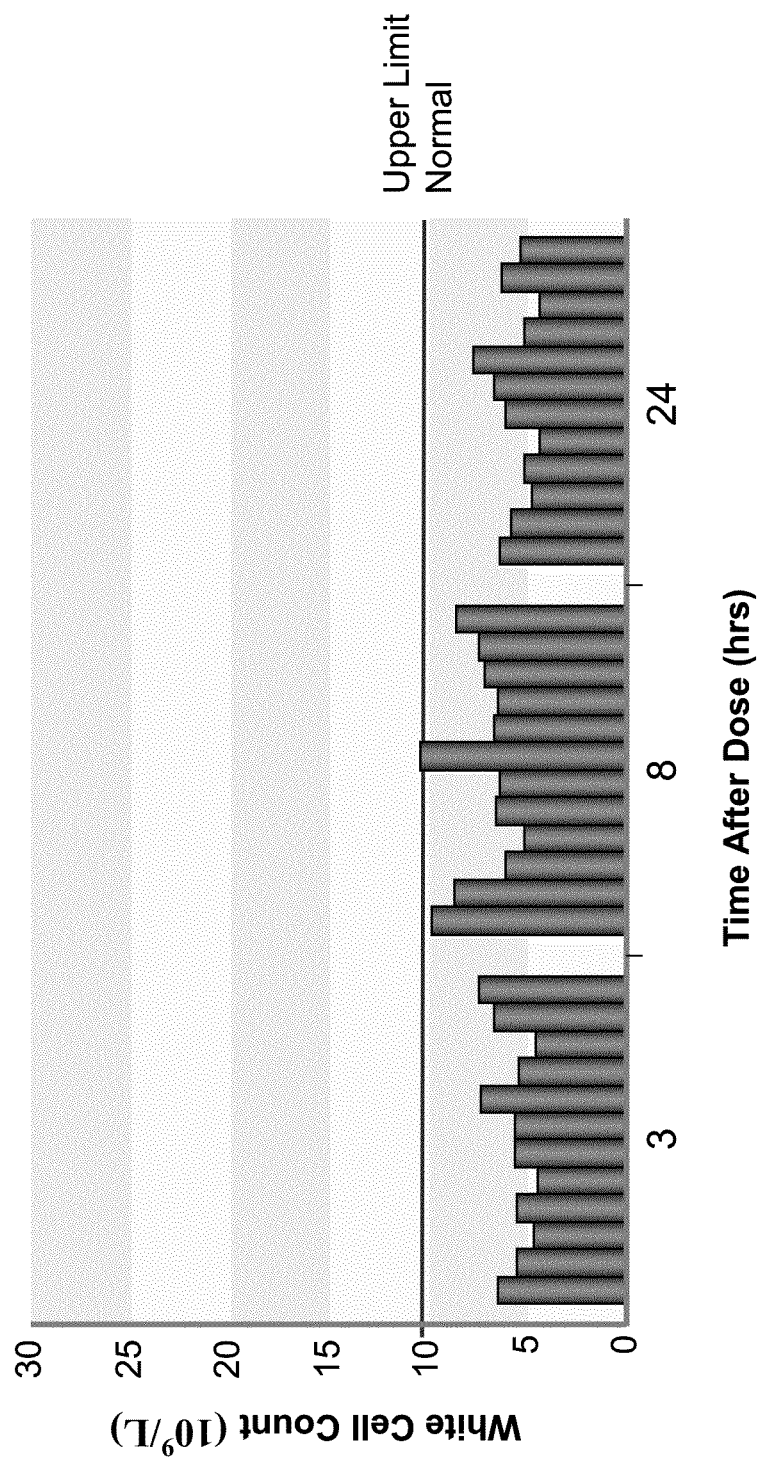

FIG. 18: White cell count in human subjects after inhalation multi-dosing (once daily for three days with total dose of 0.6 mg/kg) of siRNA ALN-RSV01 targeting RSV.

Figure 19:
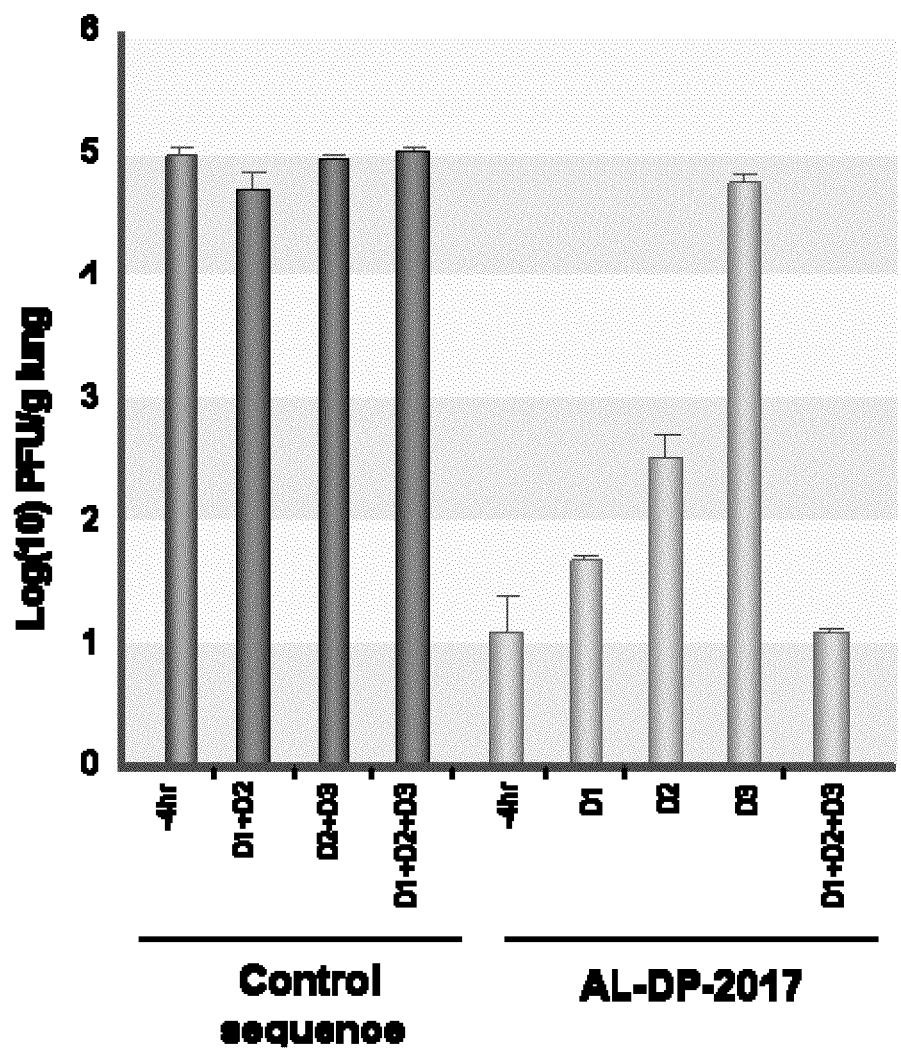

FIG. 19: RSV in the lung following administration of siRNA ALN-RSV01. RSV instillation was intranasal (106 pfu). Fixed total dose of siRNA was 120 μg. Single administration is indicated by −4 hr, D1, D2, D3; split dose over three days is indicated by D1+D2+D3.

Figure 20:
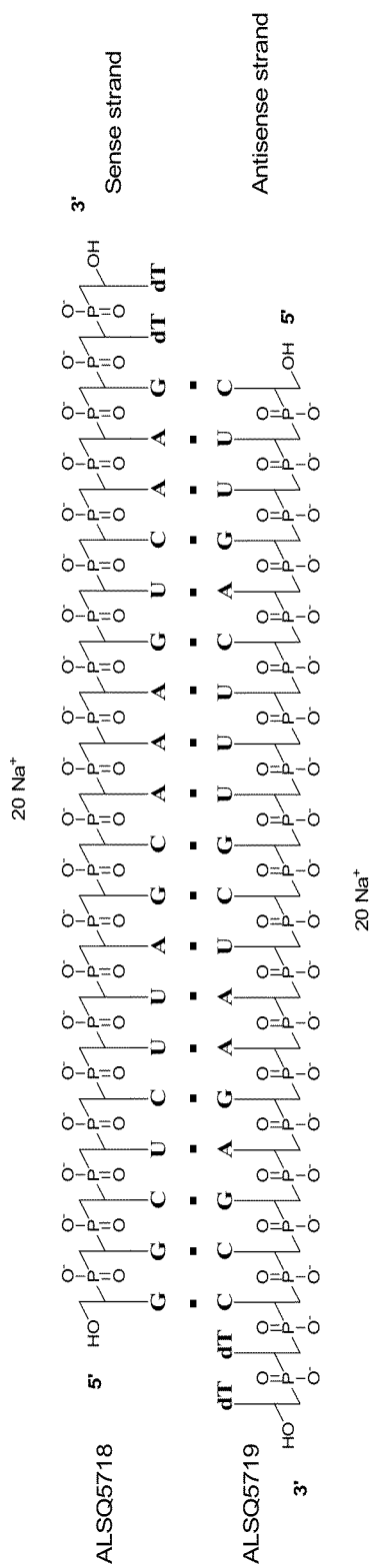

FIG. 20: Structure of ALN-RSV01 duplex. ALN-RSV01 is a synthetic double-stranded RNA (dsRNA) oligonucleotide (SEQ ID NOS 1 and 2) formed by hybridization of two partially complementary single strand RNAs in which the 3' ends are capped with two thymidine units. Hybridization occurs across 19 ribonucleotide base pairs to yield the ALN-RSV01 molecule. All the phosphodiester functional groups are negatively charged at neutral pH with a sodium ion as the counter ion.

Figure 21:
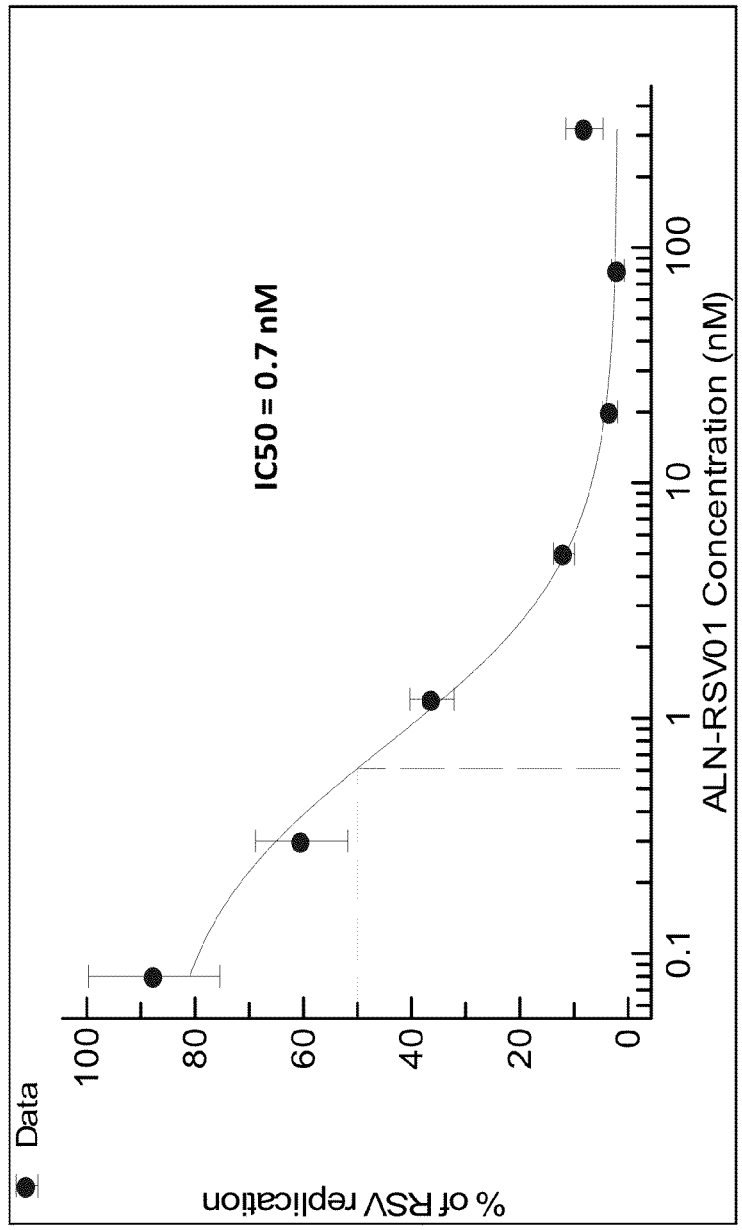

FIG. 21: In vitro IC50 of ALN-RSV01. Vero cells in 24-well plates were transfected with decreasing concentration of ALN-RSV01 followed by infection with 200-300 pfu of RSV/A2. At 5 days post-infection, cells were fixed, immunostained, and counted. Percent activity against PBS was plotted and IC50 measured using XLFit software.

FIG. 22: In vivo activity of ALN-RSV01 following single and multidosing in BALB/c mice. A) ALN-RSV01 in vivo dose response curve. BALB/c mice were intranasally treated with ALN-RSV01 at increasing concentrations (25 μg, 50 μg, or 100 μg), control siRNA AL-DP-1730 or PBS 4 hours prior to infection with 1×106 pfu of RSV/A2. Lungs were harvested and virus quantified by standard immunostaining plaque assay and plotted as log pfu/g lung. B) ALN-RSV01 multidose study. BALB/c mice were intranasally treated with ALN-RSV01 or mismatch siRNA (1730) at either 40 μg, 80 μg, or 120 μg (single dose treatment) or 40 μg (multidose, daily treatment). Lungs were harvested and virus quantified by immunostaining plaque assay on D5. −4, 4 hours prior to infection; D1, day 1 post-infection; D2, day 2 post-infection; D3, day 3 post-infection. C) ALN-RSV01 same day multi-dose study. BALB/c mice were intranasally treated with ALN-RSV01 or mismatch siRNA (1730) at either 40 μg, 60 μg, 80 μg, or 120 μg for single dose groups at days 1 or 2 post-RSV infection, or 40 μg 2× or 3× daily for multidose groups at day 1 or 2 post-RSV infection. Lungs were harvested and virus quantified by immunostaining plaque assay.

Figure 23A:
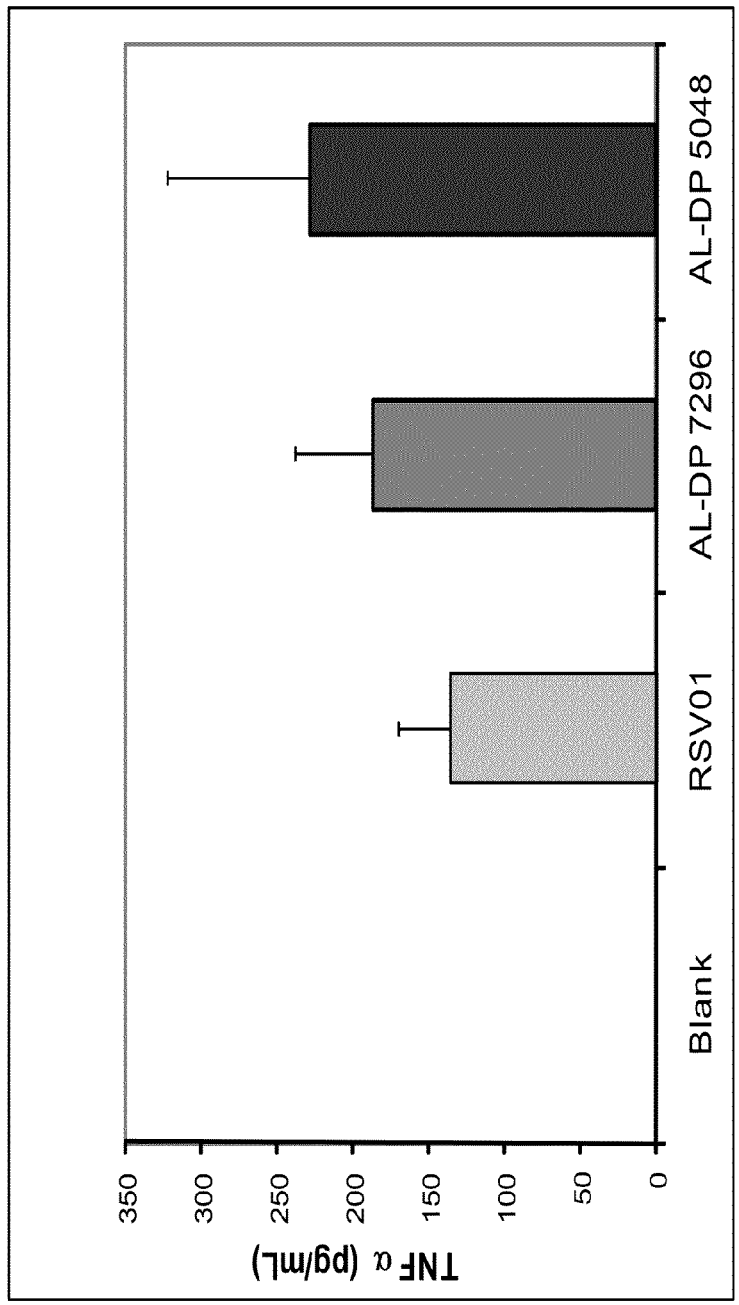
Figure 23B:
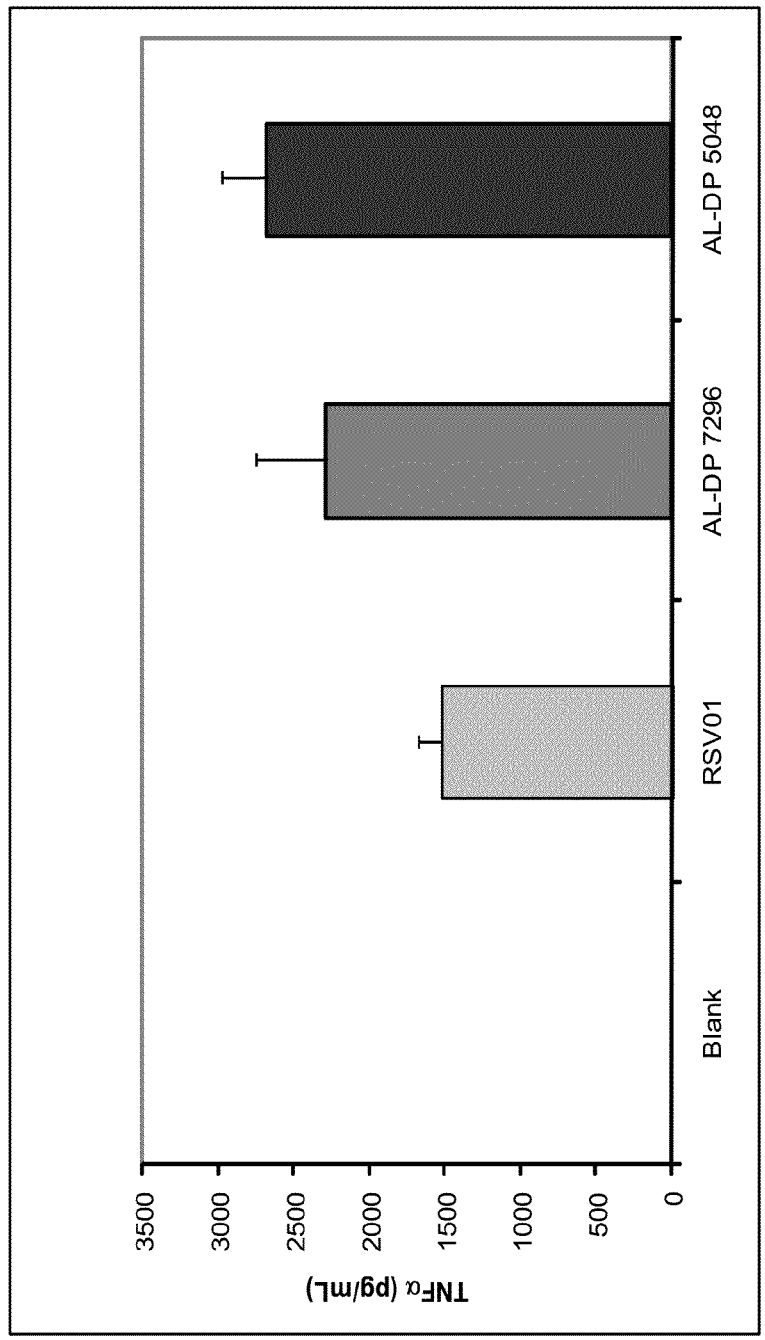

FIG. 23: ALN-RSV01 is a modest stimulatory of IFNα and TNFα in vitro. siRNAs (ALN-RSV01 or mismatch positive controls, 7296 and 5048) were transfected into peripheral blood mononuclear cells and assayed by ELISA for induction of cytokines at 24 hrs post transfection. A) IFNα induction; B) TNFα induction.

Figure 24A:
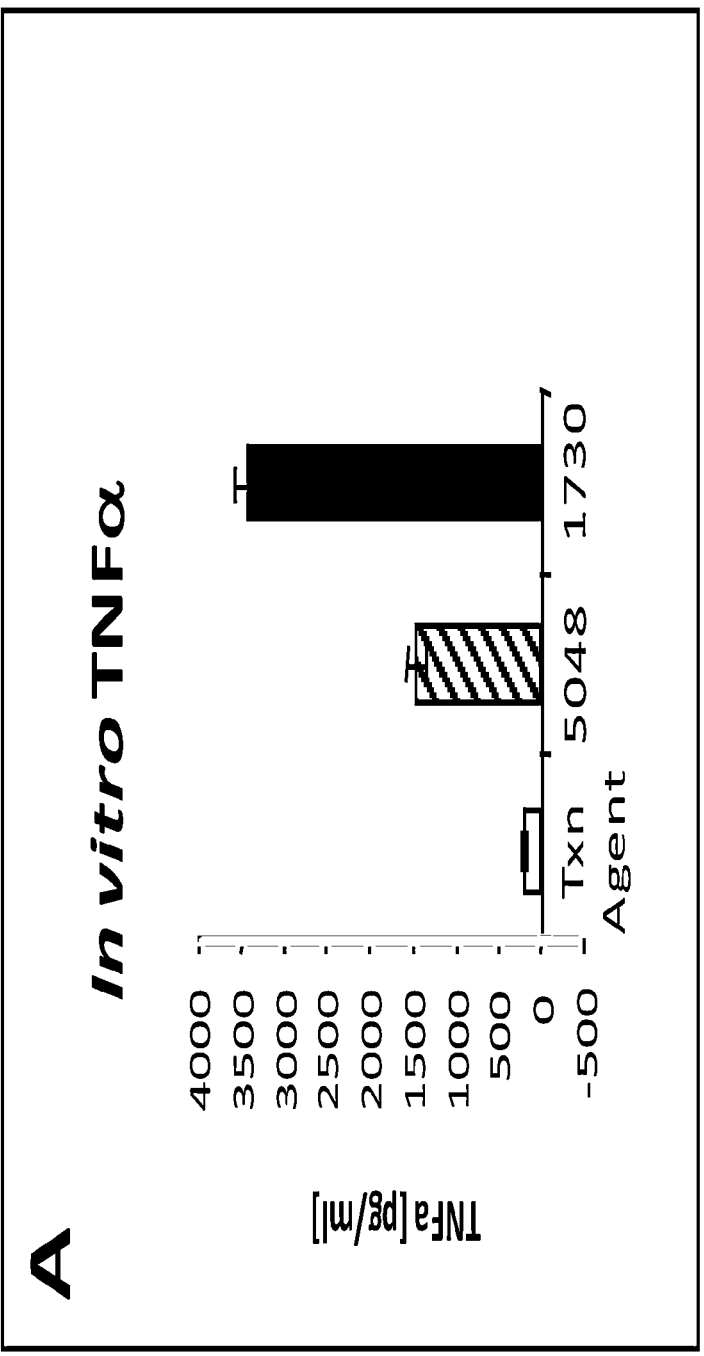
Figure 24B:
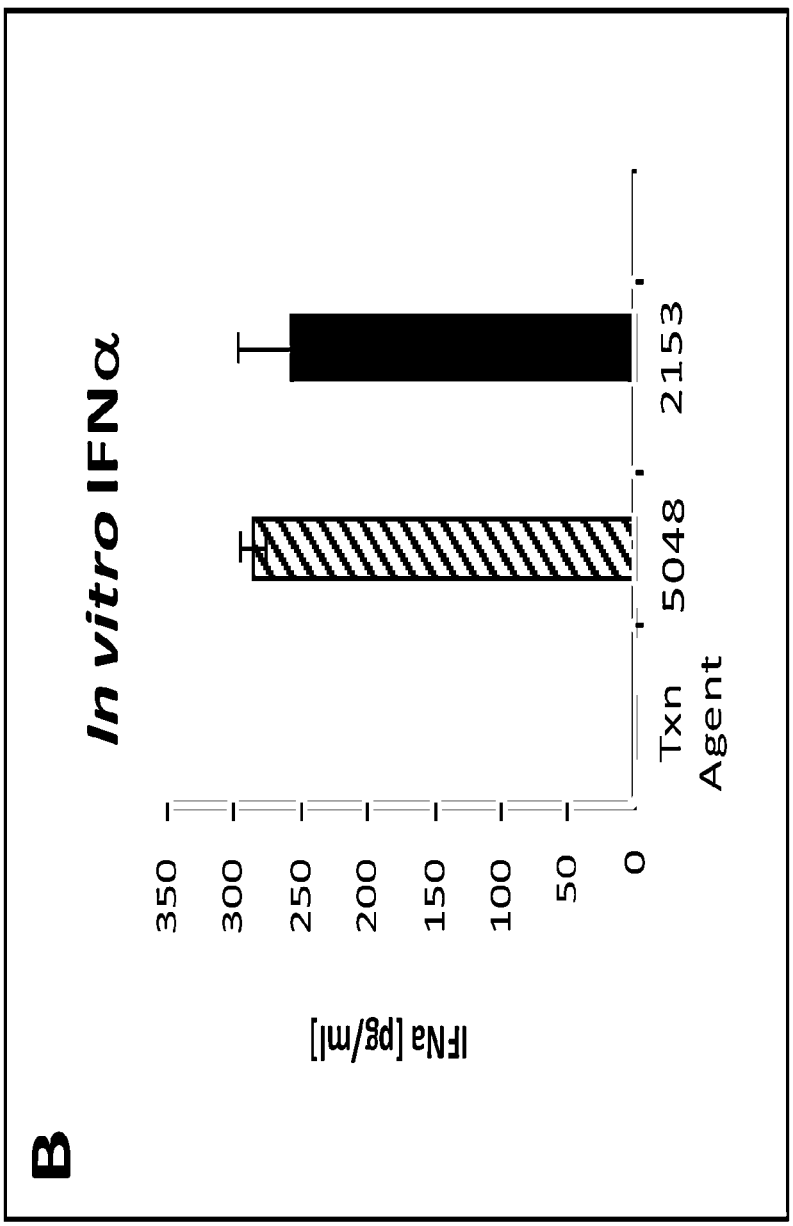

FIG. 24: TNFα and IFNα stimulatory mismatched siRNAs do not modulate RSV in vivo. A) siRNAs transfected into peripheral blood mononuclear cells were assayed for TNFα stimulation at 24 hrs post transfection. B) siRNAs transfected into peripheral blood mononuclear cells were assayed for IFNα stimulation at 24 hrs post transfection. C) Lung viral concentrations from mice intranasally dosed with RSV at day 0 and with RSV-specific siRNAs (ALN-RSV01) or mismatch control immunostimulatory siRNAs (2153 and 1730) at 4 hrs pre inoculation. Lung RSV concentrations were measured by immunostaining plaque assay at day 5 post infection.

Figure 25:
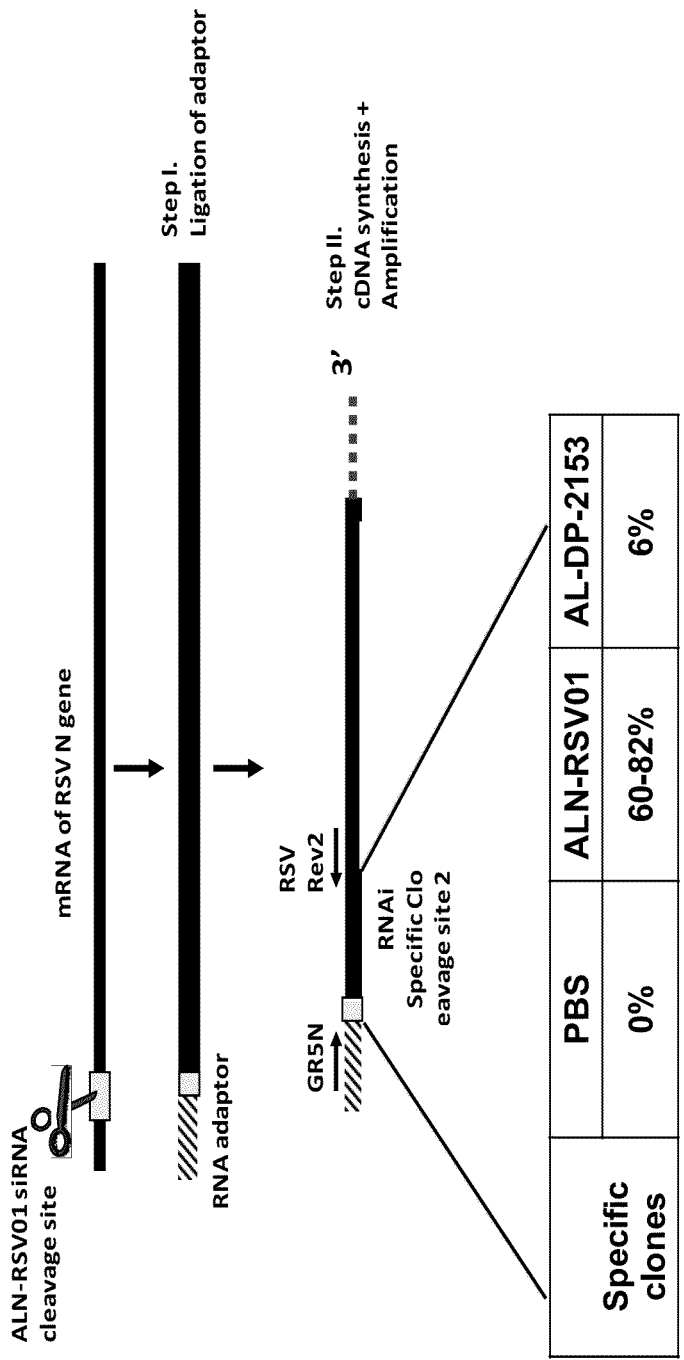

FIG. 25: ALN-RSV01 viral inhibition is mediated by RNAi in vivo. Shown is a schematic representation of the 5'-RACE assay used to demonstrate the generation of site-specific cleavage product. Boxed are the results of sequence analysis of individual clones isolated from PCR amplification of linker adapted RSV N gene cDNAs generated from an in vivo viral inhibition assay in which mice were inoculated with RSV at day 0 and treated with ALN-RSV01, AL-DP-1730 or PBS at day 3, followed by lung homogenization and evaluation by RACE at day 5 post infection.

Figure 26A:
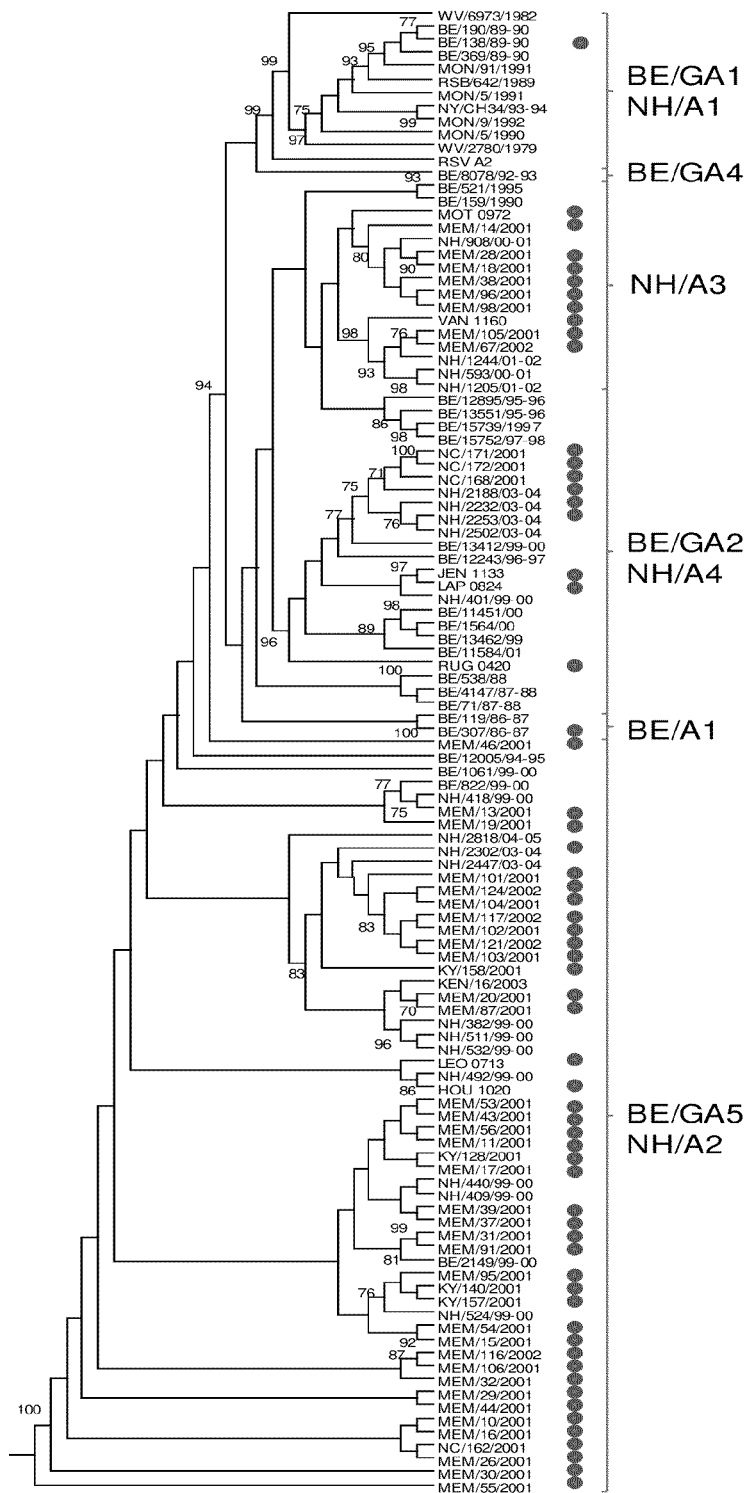
Figure 26B:
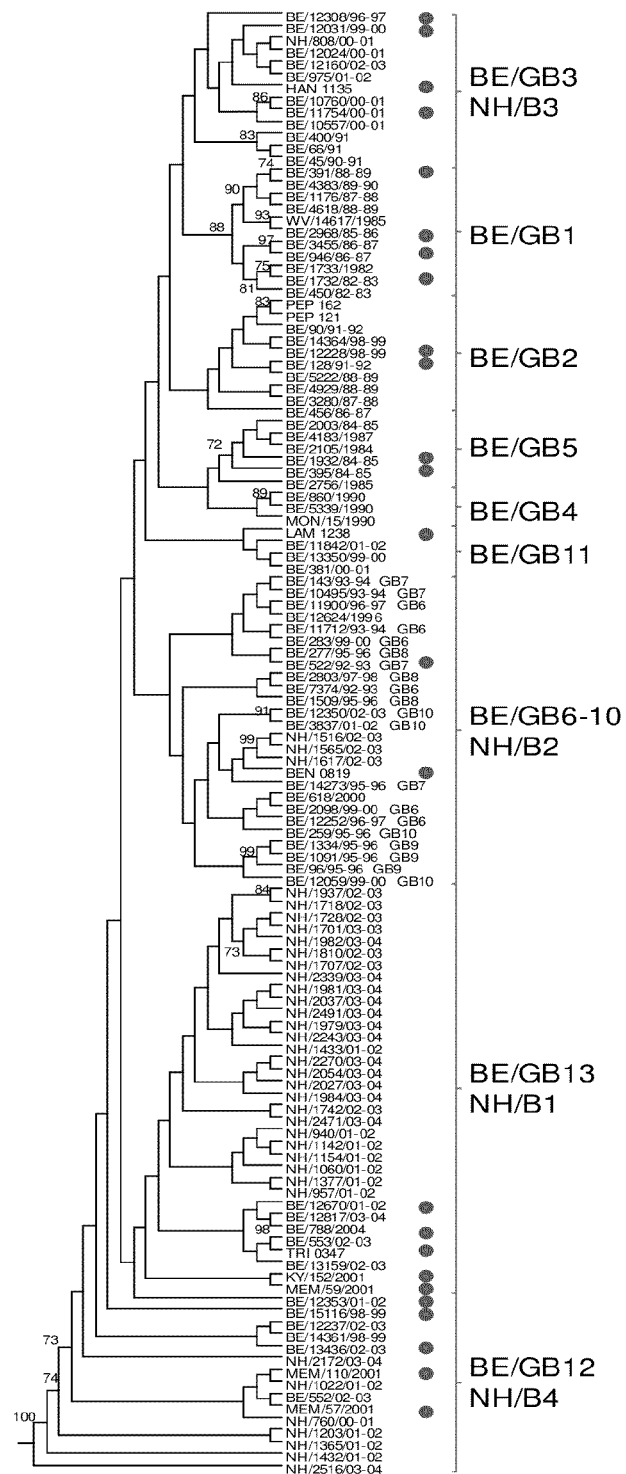

FIG. 26: Genotype analysis of RSV primary isolates. Maximum likelihood phylogenetic trees for (A) RSV A and (B) RSV B based upon analysis of the RSV G gene. Bootstrap values >70% (1,000 replicates) are shown at the corresponding node. Circles indicate isolates analyzed at the ALN-RSV01 target site.

Figure 27:
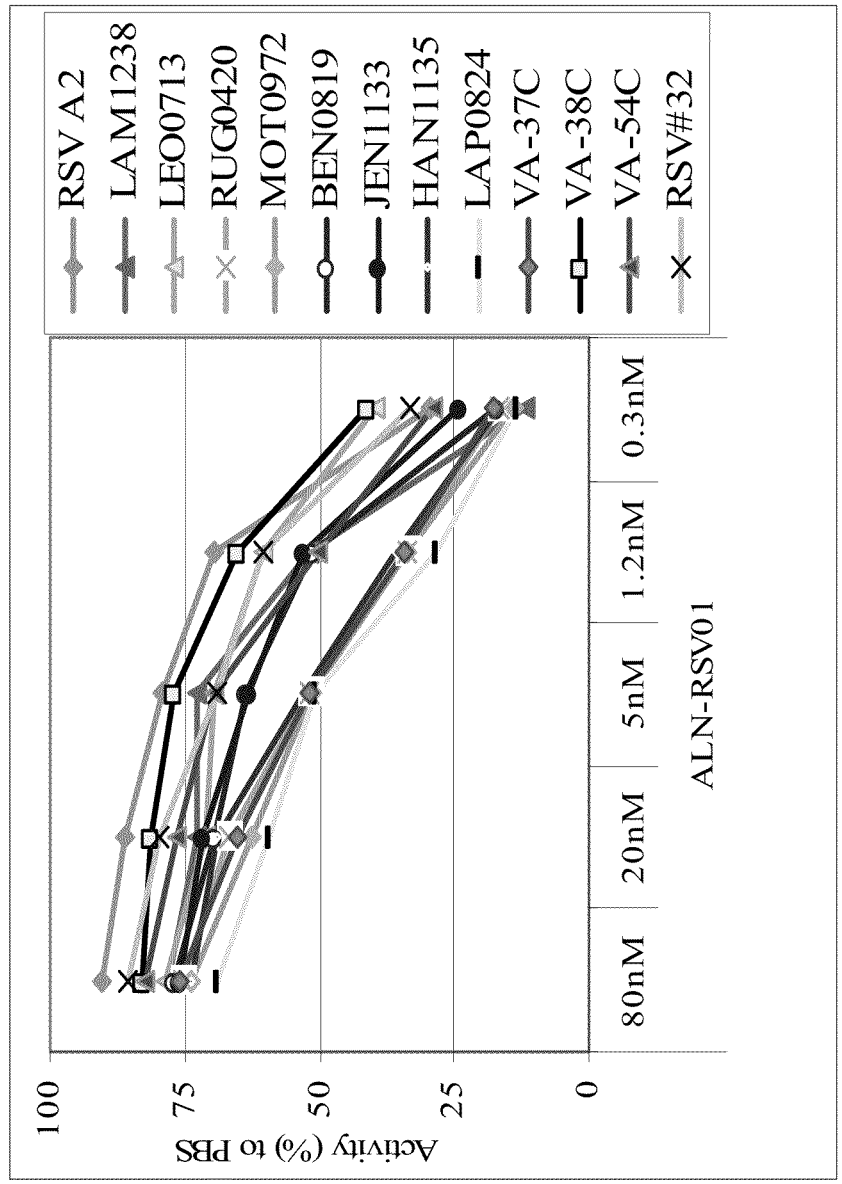

FIG. 27: In vitro inhibition of primary RSV isolates by ALN-RSV01. Vero cells in 24-well plates were transfected with decreasing concentrations of ALN-RSV01 followed by infection with 200-300 pfu of RSV primary isolates. At day 5 post-infection, cells were fixed, immunostained, and counted. Percent activity against PBS was plotted.

FIG. 28: A Sample Symptom Score Card is depicted.

FIG. 29: Table shows the baseline characteristics of subjects used in a randomized, double-blind, placebo controlled study of a therapeutic iRNA (ALN-RSV01) directed against RSV.

FIG. 30: Table summarizes the primary efficacy outcome: infection rate (cohorts 1-6).

FIG. 31: Table summarizes results of statistical analyses used to evaluate independent effects on infection, where infection is measured by quantitative culture.

FIG. 32: Table summarizes treatment-emergent adverse events (>5% incidence) documented during course of randomized study of RSV01 efficacy.

Figure 33:
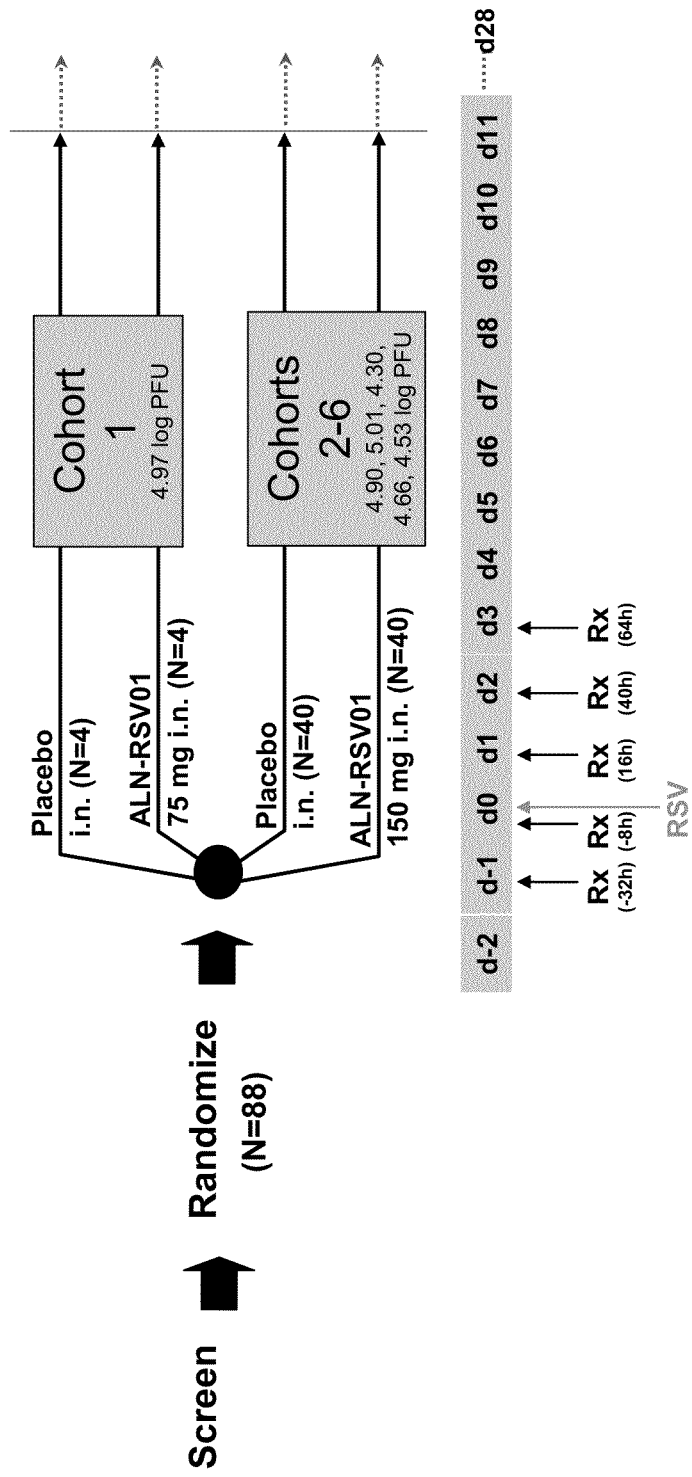

FIG. 33: Study Design for Randomized Phase II trial of Intranasal ALN-RSV01 Versus Placebo in Subjects Experimentally Infected with RSV. i.n.: intranasal; d: study day; h: hours; Rx: dosing with ALN-RSV01 or placebo; RSV: inoculation with RSV, with quantity of inoculum administered to subjects in each cohort indicated in the boxes labeled "Cohort 1" and "Cohorts 2-6." Three subjects (1 active, 2 placebo) were withdrawn from Cohort 6 due to food-related gastroenteritis having received one study drug dose, and without receiving RSV inoculation. Thus, 88 were evaluated for safety and 85 for efficacy. Subjects were quarantined from Day −2 through Day 11. Nasal washes were obtained daily during quarantine except on days −1, 0, and 1 so as not to affect study drug or RSV inoculation.

Figure 34:
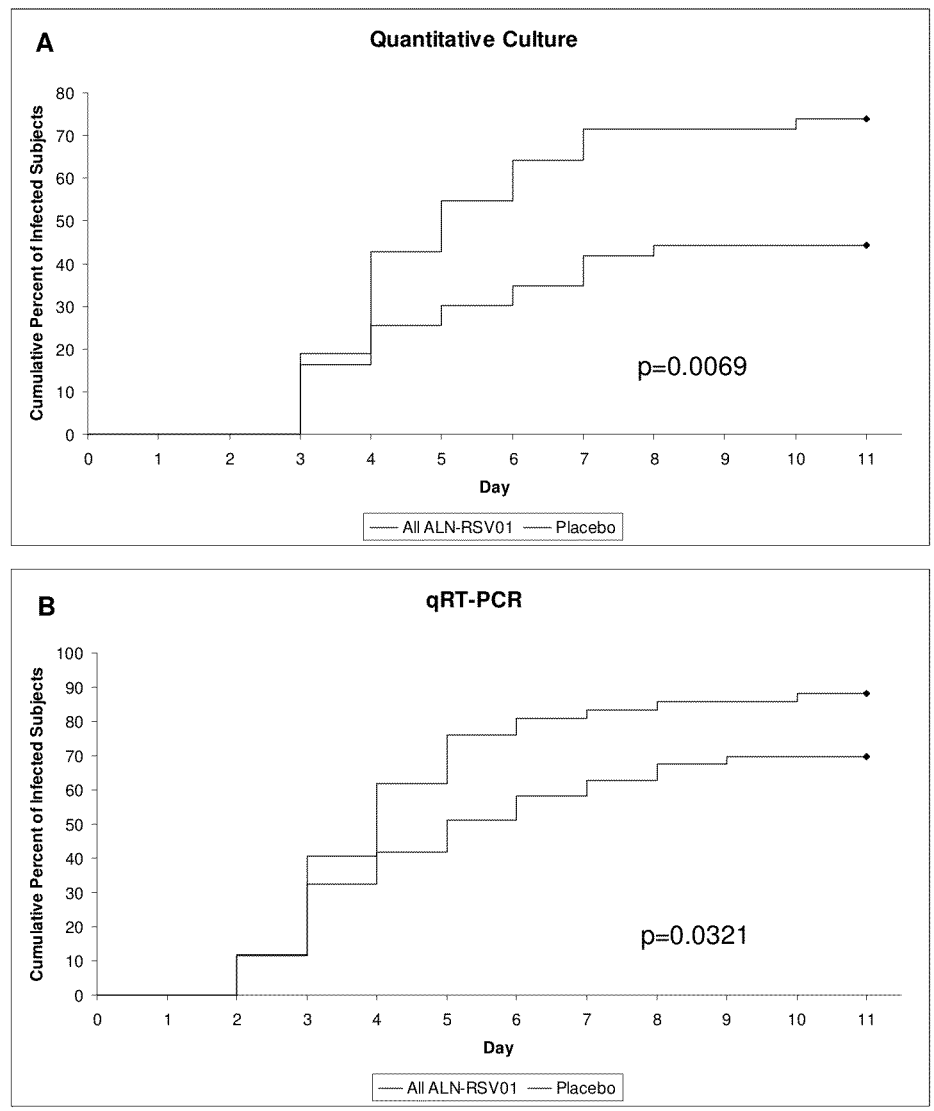

FIG. 34: Reverse Kaplan-Meier curves are shown for ALN-RSV01 and placebo, with infection determined either by (A) quantitative culture (plaque assay) or (B) qRT-PCR. Inoculation with RSV occurred at Day 0, while daily treatment with intranasal ALN-RSV01 or placebo continued from Day −1 through Day 3.

FIG. 35: Quantitative Viral and Disease Measures in Subjects Treated with ALNRSV01 or Placebo. Panels A-D: Results shown are for both infected and uninfected subjects combined in each treatment arm, with infection measured either by quantitative culture or qRT-PCR. In panels (A) and (B), the bars show the mean and standard error for viral AUC and peak viral load over Days 2-11 27 following viral inoculation on Day 0. In panels (C) and (D), the curves show the mean and standard error for viral load on each day from Days 2-11. Panels E-G: Results are for all subjects in each treatment arm, with individual results (dots) and mean for the group (horizontal bar) shown for (E) mean total symptom score, (F) mean total directed physical exam (DPE) score, and (G) mean mucus weight. Panels H-I: Mean daily symptom score and standard error for ALN-RSV01 or placebo by study day, with results shown for (H) all subjects or for (I) infected subjects, with infection confirmed by quantitative culture or qRT-PCR. Inoculation with RSV occurred on Day 0, and the period of treatment with either ALN-RSV01 or placebo is shown by the solid horizontal bar.

Figure 36:
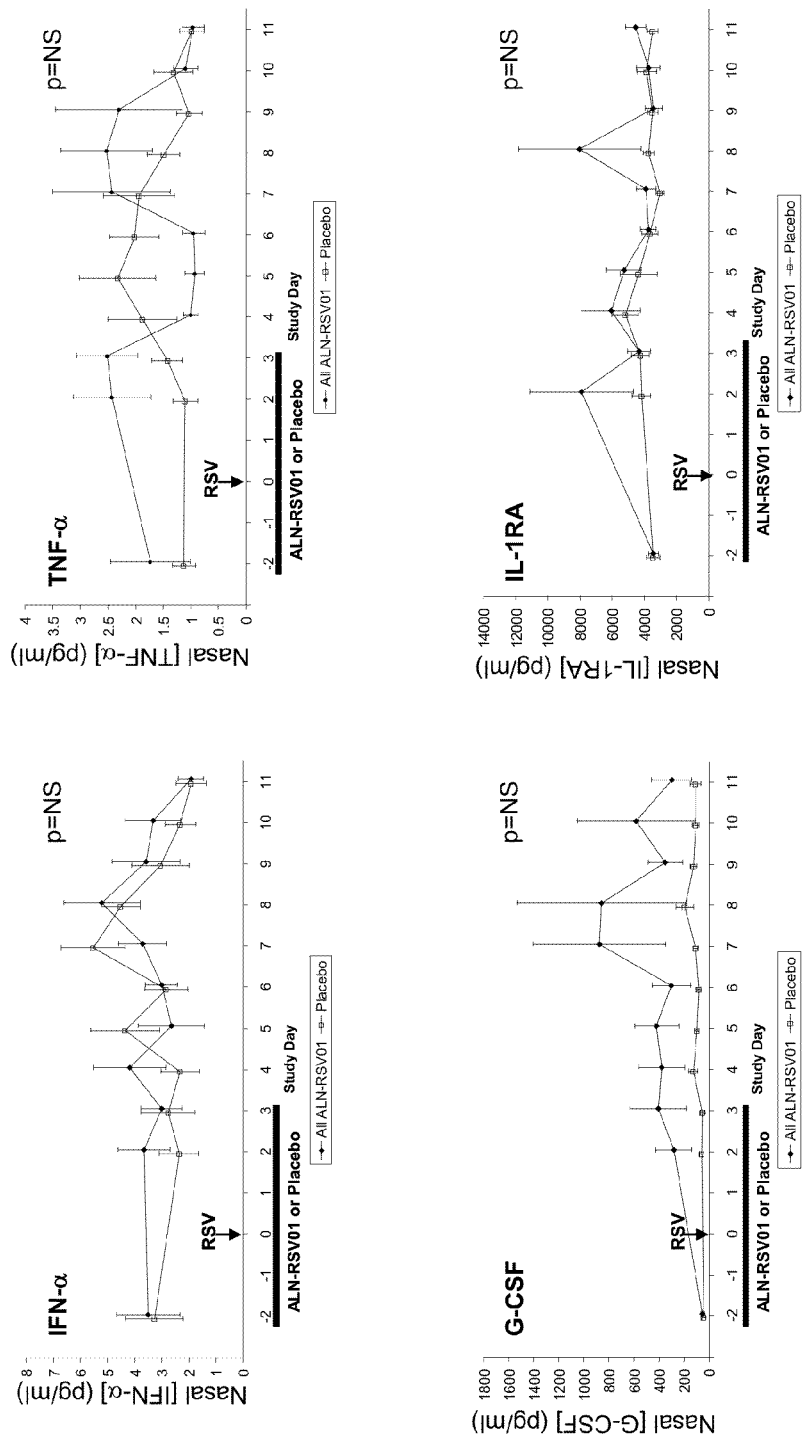

FIG. 36. Intranasal Cytokine Concentrations in Subjects Treated with ALN-RSV01 or Placebo. Shown are mean daily nasal wash cytokine concentrations and standard errors on study day −2 and study days 2-11 for subjects receiving ALN-RSV01 (closed diamonds) or placebo (open squares). Inoculation with RSV occurred on Day 0, and the period of treatment with either ALN-RSV01 or placebo is shown by the solid horizontal bar.

FIG. 37. Specific iRNA mediated cleavage products in human patients. (A) shows that nasal samples taken from patients treated with ALN-RSV01 have increased levels of specific cleavage products relative to patients treated with placebo. (B) shows a plot of RSV titer versus % correct cleavage (left), and the relationship between % correct cleavage versus time after drug dosing (right).

DETAILED DESCRIPTION

The instant specification may refer to one or more of the following abbreviations whose meanings are defined in Table 2, below.

TABLE 2

LIST OF ABBREVIATIONS

| | |
|---|---|
| A | Adenosine |
| AAS | Atomic Absorption Spectroscopy |
| Ado | Adenosine |
| AE | Adverse Event |
| ALT | Alanine aminotransferase |
| AST | Aspartate aminotransferase |
| AUC | Area under the concentration-time curve |
| AX-HPLC | Anion Exchange High Performance Liquid Chromatography |
| BMI | Body mass index |
| bpm | Beats per minute |
| BUN | Blood urea nitrogen |
| C | Cytidine |
| Ca | Calcium |
| CBC | Complete blood cell [count] |
| CDER | Center for Drug Evaluation and Research |
| CFR | Code of Federal Regulations |
| CFU | Colony-Forming Units |
| cGMP | Current Good Manufacturing Practices |
| Cl | Chloride |
| COPD | Chronic Obstructive Pulmonary Disease |
| CPG | Controlled Pore Glass |
| CRF | Case Report Form |
| CRO | Contract Research Organization |
| CRP | c-Reactive Protein |

TABLE 2-continued

LIST OF ABBREVIATIONS

| | |
|---|---|
| CTCAE | Common Terminology Criteria for Adverse Events |
| CV | Curriculum Vitae |
| Cyd | Cytidine |
| Da | Daltons |
| DLT | Dose-limiting toxicity (ies) |
| DMT | Dimethoxytrityl |
| dsRNA | Double-stranded ribonucleic acid |
| dT | Thymidine |
| dThd | Thymidine |
| ECG | Electrocardiogram |
| EP | European Pharmacopeia |
| ESI | Electrospray Ionization |
| EU | Endotoxin Units |
| FDA | Food and Drug Administration |
| FLP | Full Length Product |
| FTIR | Fourier Transform Infrared Spectroscopy |
| G | Gram |
| G | Guanosine |
| GC | Gas Chromatography |
| GCP | Good Clinical Practice |
| G-CSF | Granulocyte colony stimulating factor |
| GMP | Good Manufacturing Practices |
| Guo | Guanosine |
| HBsAg | Hepatitis B Surface Antigen |
| Hct | Hematocrit |
| HCV | Hepatitis C Virus |
| HFIP | Hexafluoroisopropanol |
| Hgb | Hemoglobin |
| HIPAA | Health Insurance Portability and Accountability Act |
| HIV | Human Immunodeficiency Virus |
| HPLC | High Performance Liquid Chromatography |
| IB | Investigator's Brochure |
| ICF | Informed Consent Form |
| ICH | International Conference on Harmonization |
| ICP | Inductively Coupled Plasma |
| ICP-MS | Inductively Coupled Plasma Mass Spectrometry |
| ID | Identity |
| IEC | Independent Ethics Committee |
| IL-10 | Interleukin 10 |
| IL-8 | Interleukin 8 |
| IMPD | Investigational Medicinal Product Dossier |
| INR | International Normalized Ratio |
| IRB | Institutional Review Board |
| IRC | Independent Review Committee |
| ITT | Intent to treat |
| K | Potassium |
| kg | Kilogram |
| LAL | Limulus Amebocyte Lysate |
| LC-MS | Liquid Chromatography-Mass Spectrometry |
| LDH | Lactate dehydrogenase |
| LLOQ | Lower Limit of Quantification |
| M | Molar |
| MALDI-TOF | Matrix Assisted Laser Desorption Ionization - Time of Flight |
| MCH | Mean corpuscular hemoglobin |
| MCHC | Mean corpuscular hemoglobin concentration |
| MCV | Mean corpuscular volume |
| MedDRA | Medical Dictionary for Regulatory Activities |
| mg | Milligram |
| mL | Milliliter |
| mM | Millimolar |
| mRNA | Messenger Ribonucleic Acid |
| MS | Mass Spectrometry |
| MTD | Maximum tolerated dose |
| MW | Molecular Weight |
| N | Full Length Oligonucleotide of the Intermediate Single Strands |
| Na | Sodium |
| NaCl | Sodium chloride |
| ND | Not Detected |
| NF | National Formulary |
| nm | Nanometer |
| NMR | Nuclear Magnetic Resonance |
| NOAEL | No observed adverse effect level |
| NOEL | No observed effect level |
| NT | Not Tested |
| OTC | Over the counter |
| PBS | Phosphate Buffered Solution |

TABLE 2-continued

LIST OF ABBREVIATIONS

| | |
|---|---|
| PE | Physical examination |
| PES | Polyethersulfone |
| pH | Potential of Hydrogen |
| PI | Principal Investigator |
| PK | Pharmacokinetics |
| PP | Per protocol |
| ppm | Parts Per Million |
| PT | Prothrombin Time |
| PTT | Partial thromboplastin time |
| PVDF | Polyvinylidene Difluoride |
| q.s. | Quantity Sufficient |
| QC | Quality Control |
| RBC | Red Blood Cell |
| RH | Relative Humidity |
| RISC | RNA induced silencing complex |
| RNA | Ribonucleic Acid |
| RNAi | RNA interference |
| RRT | Relative Retention Time |
| RSV | Respiratory Syncytial Virus |
| RTM | RSV Transport Media |
| rt-PCR | Reverse transcriptase polymerase chain reaction |
| SAE | Serious adverse event |
| SAP | Statistical Analysis Plan |
| SAR | Seasonal allergic rhinitis |
| SEC | Size Exclusion Chromatography |
| siRNA | Small Interfering Ribonucleic Acid |
| SOP | Standard Operating Procedure |
| SP | Safety Population |
| TBDMS | Tert-butyldimethylsilyl |
| TCID50 | Tissue culture infective dose producing 50% infection |
| TFF | Tangential Flow Filtration |
| Tm | Duplex Helix to Coil Melting Temperature |
| TNF | Tumor necrosis factor |
| U | Uridine |
| UF | Ultrafiltration |
| UK | United Kingdom |
| Urd | Uridine |
| US | United States |
| USP | United States Pharmacopeia |
| USP/NF | United States Pharmacopeia/National Formulary |
| UV | Ultraviolet |
| w/v | Weight by Volume |
| w/w | Weight by Weight |
| WBC | White Blood Cell |
| WHO | World Health Organization |

For ease of exposition the term "nucleotide" or "ribonucleotide" is sometimes used herein in reference to one or more monomeric subunits of an RNA agent. It will be understood that the usage of the term "ribonucleotide" or "nucleotide" herein can, in the case of a modified RNA or nucleotide surrogate, also refer to a modified nucleotide, or surrogate replacement moiety, as further described below, at one or more positions.

An "RNA agent" as used herein, is an unmodified RNA, modified RNA, or nucleoside surrogate, all of which are described herein or are well known in the RNA synthetic art. While numerous modified RNAs and nucleoside surrogates are described, preferred examples include those which have greater resistance to nuclease degradation than do unmodified RNAs. Preferred examples include those that have a 2' sugar modification, a modification in a single strand overhang, preferably a 3' single strand overhang, or, particularly if single stranded, a 5'-modification which includes one or more phosphate groups or one or more analogs of a phosphate group.

An "iRNA agent" (abbreviation for "interfering RNA agent") as used herein, is an RNA agent, which can down-regulate the expression of a target gene, e.g., RSV. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can be a double stranded (ds) iRNA agent.

A "ds iRNA agent" (abbreviation for "double stranded iRNA agent"), as used herein, is an iRNA agent which includes more than one, and preferably two, strands in which interchain hybridization can form a region of duplex structure. A "strand" herein refers to a contiguous sequence of nucleotides (including non-naturally occurring or modified nucleotides). The two or more strands may be, or each form a part of, separate molecules, or they may be covalently interconnected, e.g. by a linker, e.g. a polyethyleneglycol linker, to form but one molecule. At least one strand can include a region which is sufficiently complementary to a target RNA. Such strand is termed the "antisense strand". A second strand comprised in the dsRNA agent which comprises a region complementary to the antisense strand is termed the "sense strand". However, a ds iRNA agent can also be formed from a single RNA molecule which is, at least partly; self-complementary, forming, e.g., a hairpin or panhandle structure, including a duplex region. In such case, the term "strand" refers to one of the regions of the RNA molecule that is complementary to another region of the same RNA molecule.

Although, in mammalian cells, long ds iRNA agents can induce the interferon response which is frequently deleterious, short ds iRNA agents do not trigger the interferon response, at least not to an extent that is deleterious to the cell and/or host. The iRNA agents of the present invention include molecules which are sufficiently short that they do not trigger a deleterious interferon response in mammalian cells. Thus, the administration of a composition of an iRNA agent (e.g., formulated as described herein) to a mammalian cell can be used to silence expression of an RSV gene while circumventing a deleterious interferon response. Molecules that are short enough that they do not trigger a deleterious interferon response are termed siRNA agents or siRNAs herein. "siRNA agent" or "siRNA" as used herein, refers to an iRNA agent, e.g., a ds iRNA agent, that is sufficiently short that it does not induce a deleterious interferon response in a human cell, e.g., it has a duplexed region of less than 30 nucleotide pairs.

The isolated iRNA agents described herein, including ds iRNA agents and siRNA agents, can mediate silencing of a gene, e.g., by RNA degradation. For convenience, such RNA is also referred to herein as the RNA to be silenced. Such a gene is also referred to as a target gene. Preferably, the RNA to be silenced is a gene product of an RSV gene, particularly the P, N or L gene product.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secret at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element.

In the anti viral uses of the present invention, silencing of a target gene will result in a reduction in "viral titer" in the cell or in the subject. As used herein, "reduction in viral titer" refers to a decrease in the number of viable virus produced by a cell or found in an organism undergoing the silencing of a viral target gene. Reduction in the cellular amount of virus produced will preferably lead to a decrease in the amount of measurable virus produced in the tissues of a subject undergoing treatment and a reduction in the severity of the symptoms of the viral infection. iRNA agents of the present invention are also referred to as "antiviral iRNA agents".

As used herein, a "RSV gene" refers to any one of the genes identified in the RSV virus genome (See Falsey, A. R., and E. E. Walsh, 2000, Clinical Microbiological Reviews 13:371-84). These genes are readily known in the art and include the N, P and L genes which are exemplified herein.

As used herein, the term "complementary" is used to indicate a sufficient degree of complementarity such that stable and specific binding occurs between a compound of the invention and a target RNA molecule, e.g. an RSV viral mRNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 4 nucleotides.

As used herein, an iRNA agent is "sufficiently complementary" to a target RNA, e.g., a target mRNA (e.g., a target RSV mRNA) if the iRNA agent reduces the production of a protein encoded by the target RNA in a cell. The iRNA agent may also be "exactly complementary" to the target RNA, e.g., the target RNA and the iRNA agent anneal, preferably to form a hybrid made exclusively of Watson-Crick base pairs in the region of exact complementarity. A "sufficiently complementary" iRNA agent can include an internal region (e.g., of at least 10 nucleotides) that is exactly complementary to a target viral RNA. Moreover, in some embodiments, the iRNA agent specifically discriminates a single-nucleotide difference. In this case, the iRNA agent only mediates RNAi if exact complementarity is found in the region (e.g., within 7 nucleotides of) the single-nucleotide difference. Preferred iRNA agents will be based on or consist or comprise the sense and antisense sequences provided in the Examples.

As used herein, "essentially identical" when used referring to a first nucleotide sequence in comparison to a second nucleotide sequence means that the first nucleotide sequence is identical to the second nucleotide sequence except for up to one, two or three nucleotide substitutions (e.g. adenosine replaced by uracil).

As used herein, a "subject" refers to a mammalian organism undergoing treatment for a disorder mediated by viral expression, such as RSV infection or undergoing treatment prophylactically to prevent viral infection. The subject can be any mammal, such as a primate, cow, horse, mouse, rat, dog, pig, goat. In the preferred embodiment, the subject is a human.

As used herein, treating RSV infection refers to the amelioration of any biological or pathological endpoints that 1) is mediated in part by the presence of the virus in the subject and 2) whose outcome can be affected by reducing the level of viral gene products present.

Design and Selection of iRNA Agents

The present invention is based on the demonstration of target gene silencing of a respiratory viral gene in vivo following local administration to the lungs and nasal passage of an iRNA agent either via intranasal administration/inhalation or systemically/parenterally via injection and the resulting treatment of viral infection. The present invention is further extended to the use of iRNA agents to more than one respiratory virus and the treatment of both virus infections with co-administration of two or more iRNA agents.

Based on these results, the invention specifically provides an iRNA agent that can be used in treating viral infection, particularly respiratory viruses and in particular RSV infection, in isolated form and as a pharmaceutical composition described below. Such agents will include a sense strand having at least 15 or more contiguous nucleotides that are complementary to a viral gene and an antisense strand having at least 15 or more contiguous nucleotides that are complementary to the sense strand sequence. Particularly useful are iRNA agents that consist of, consist essentially of or comprise a nucleotide sequence from the P N and L gene of RSV as provided in Table 1 (a-c).

The iRNA agents of the present invention are based on and comprise at least 15 or more contiguous nucleotides from one of the iRNA agents shown to be active in Table 1 (a-c). In such agents, the agent can consist of consist essentially of or comprise the entire sequence provided in the table or can comprise 15 or more contiguous residues provided in Table 1a-c along with additional nucleotides from contiguous regions of the target gene.

An iRNA agent can be rationally designed based on sequence information and desired characteristics and the information provided in Table 1 (a-c). For example, an iRNA agent can be designed according to sequence of the agents provided in the Tables as well as in view of the entire coding sequence of the target gene.

Accordingly, the present invention provides iRNA agents comprising a sense strand and antisense strand each comprising a sequence of at least 15, 16, 17, 18, 19, 20, 21, 22 or 23 nucleotides which is essentially identical to, as defined above, a portion of a gene from a respiratory virus, particularly the P, N or L protein genes of RSV. Exemplified iRNA agents include those that comprise 15 or more contiguous nucleotides from one of the agents provided in Table 1 (a-c).

The antisense strand of an iRNA agent should be equal to or at least, 15, 16 17, 18, 19, 20, 21, 22, 23, 24, 25, 26, 27, 28, 29, 30, 40, or 50 nucleotides in length. It should be equal to or less than 50, 40, or 30, nucleotides in length. Preferred ranges are 15-30, 17 to 25, 19 to 23, and 19 to 21 nucleotides in length. Exemplified iRNA agents include those that comprise 15 or more nucleotides from one of the antisense strands of one of the agents in Table 1 (a-c).

The sense strand of an iRNA agent should be equal to or at least 15, 16 17, 18, 19, 20, 21, 22, 23, 24, 25, 26, 27, 28, 29, 30, 40, or 50 nucleotides in length. It should be equal to or less than 50, 40, or 30 nucleotides in length. Preferred ranges are 15-30, 17 to 25, 19 to 23, and 19 to 21 nucleotides in length. Exemplified iRNA agents include those that comprise 15 or more nucleotides from one of the sense strands of one of the agents in Table 1 (a-c).

The double stranded portion of an iRNA agent should be equal to or at least, 15, 16 17, 18, 19, 20, 21, 22, 23, 24, 25, 26, 27, 28, 29, 30, 40, or 50 nucleotide pairs in length. It should be equal to or less than 50, 40, or 30 nucleotides pairs in length. Preferred ranges are 15-30, 17 to 25, 19 to 23, and 19 to 21 nucleotides pairs in length.

The agents provided in Table 1 (a-c) are 21 nucleotides in length for each strand. The iRNA agents contain a 19 nucleotide double stranded region with a 2 nucleotide overhang on each of the 3' ends of the agent. These agents can be modified as described herein to obtain equivalent agents comprising at least a portion of these sequences (15 or more contiguous nucleotides) and or modifications to the oligonucleotide bases and linkages.

Generally, the iRNA agents of the instant invention include a region of sufficient complementarity to the viral gene, e.g. the P, N or L protein of RSV, and are of sufficient length in terms of nucleotides, that the iRNA agent, or a fragment thereof, can mediate down regulation of the specific viral gene. The antisense strands of the iRNA agents of the present invention are preferably fully complementary to the mRNA sequences of viral gene, as is herein for the P, L or N proteins of RSV. However, it is not necessary that there be perfect complementarity between the iRNA agent and the target, but the correspondence must be sufficient to enable the iRNA agent, or a cleavage product thereof, to direct sequence specific silencing, e.g., by RNAi cleavage of an RSV mRNA.

Therefore, the iRNA agents of the instant invention include agents comprising a sense strand and antisense strand each comprising a sequence of at least 16, 17 or 18 nucleotides which is essentially identical, as defined below, to one of the sequences of a viral gene, particularly the P, N or L protein of RSV, such as those agent provided in Table 1 (a-c), except that not more than 1, 2 or 3 nucleotides per strand, respectively, have been substituted by other nucleotides (e.g. adenosine replaced by uracil), while essentially retaining the ability to inhibit RSV expression in cultured human cells, as defined below. These agents will therefore possess at least 15 or more nucleotides identical to one of the sequences of a viral gene, particularly the P, L or N protein gene of RSV, but 1, 2 or 3 base mismatches with respect to either the target viral mRNA sequence or between the sense and antisense strand are introduced. Mismatches to the target viral mRNA sequence, particularly in the antisense strand, are most tolerated in the terminal regions and if present are preferably in a terminal region or regions, e.g., within 6, 5, 4, or 3 nucleotides of a 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the overall double stranded character of the molecule.

It is preferred that the sense and antisense strands be chosen such that the iRNA agent includes a single strand or unpaired region at one or both ends of the molecule, such as those exemplified in Table 1 (a-c). Thus, an iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred siRNA agents will have single-stranded overhangs, preferably 3' overhangs, of 1 to 4, or preferably 2 or 3 nucleotides, in length, on one or both ends of the iRNA agent. The overhangs can be the result of one strand being longer than the other, or the result of two strands of the same length being staggered. 5'-ends are preferably phosphorylated.

Preferred lengths for the duplexed region are between 15 and 30, most preferably 18, 19, 20, 21, 22, and 23 nucleotides in length, e.g., in the siRNA agent range discussed above. Embodiments in which the two strands of the siRNA agent are linked, e.g., covalently linked are also included. Hairpin, or other single strand structures which provide the required double stranded region, and preferably a 3' overhang are also within the invention.

Evaluation of Candidate Irna Agents

A candidate iRNA agent can be evaluated for its ability to down regulate target gene expression. For example, a candidate iRNA agent can be provided, and contacted with a cell, e.g., a human cell, that has been infected with or will be infected with the virus of interest, e.g., a virus containing the target gene. Alternatively, the cell can be transfected with a construct from which a target viral gene is expressed, thus preventing the need for a viral infectivity model. The level of target gene expression prior to and following contact with the candidate iRNA agent can be compared, e.g., on an RNA, protein level or viral titer. If it is determined that the amount of RNA, protein or virus expressed from the target gene is lower following contact with the iRNA agent, then it can be concluded that the iRNA agent down-regulates target gene expression. The level of target viral RNA or viral protein in the cell or viral titer in a cell or tissue can be determined by any method desired. For example, the level of target RNA can be determined by Northern blot analysis, reverse transcription coupled with polymerase chain reaction (RT-PCR), bDNA analysis, or RNAse protection assay. The level of protein can be determined, for example, by Western blot analysis or immuno-fluorescence. Viral titer can be detected through a plaque formation assay.

Stability Testing, Modification, and Retesting of Irna Agents

A candidate iRNA agent can be evaluated with respect to stability, e.g., its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject.

When sites susceptible to cleavage are identified, a further iRNA agent can be designed and/or synthesized wherein the potential cleavage site is made resistant to cleavage, e.g. by introduction of a 2'-modification on the site of cleavage, e.g. a 2'-O-methyl group. This further iRNA agent can be retested for stability, and this process may be iterated until an iRNA agent is found exhibiting the desired stability.

In Vivo Testing

An iRNA agent identified as being capable of inhibiting viral gene expression can be tested for functionality in vivo in an animal model (e.g., in a mammal, such as in mouse, rat or primate) as shown in the examples. For example, the iRNA agent can be administered to an animal, and the iRNA agent evaluated with respect to its biodistribution, stability, and its ability to inhibit viral, e.g., RSV, gene expression or to reduce viral titer.

The iRNA agent can be administered directly to the target tissue, such as by injection, or the iRNA agent can be administered to the animal model in the same manner that it would be administered to a human. As shown herein, the agent can be preferably administered intranasally or via inhalation as a means of preventing or treating viral infection.

The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as 35S, 32P, 33P, or 3H; gold particles; or antigen particles for immunohistochemistry) or other suitable detection method.

The iRNA agent can be evaluated with respect to its ability to down regulate viral gene expression. Levels of viral gene expression in vivo can be measured, for example, by in situ hybridization, or by the isolation of RNA from tissue prior to and following exposure to the iRNA agent. Where the animal needs to be sacrificed in order to harvest the tissue, an untreated control animal will serve for comparison. Target viral mRNA can be detected by any desired method, including but not limited to RT-PCR, Northern blot, branched-DNA assay, or RNAse protection assay. Alternatively, or additionally, viral gene expression can be monitored by performing Western blot analysis on tissue extracts treated with the iRNA agent or by ELISA. Viral titer can be determined using a pfu assay.

Irna Chemistry

Described herein are isolated iRNA agents, e.g., ds iRNA agents, that mediate RNAi to inhibit expression of a viral gene, e.g., the P protein of RSV.

Methods for producing and purifying iRNA agents are well known to those of skill in the art of nucleic acid chemistry. In certain embodiments the production methods can include solid phase synthesis using phosphoramidite monomers with commercial nucleic acid synthesizers. See, e.g., "Solid-Phase Synthesis: A Practical Guide," (Steven A. Kates and Fernando Albericio (eds.), Marcel Dekker, Inc., New York, 2000). In certain embodiments the invention is practiced using processes and reagents for oligonucleotide synthesis and purification as described in co-owned PCT Application No. PCT/US2005/011490 filed Apr. 5, 2005.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res.* 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking 0 of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g., pharmacodynamic properties, which are further discussed below. Other suitable modifications to a sugar, base, or backbone of an iRNA agent are described in co-owned PCT Application No. PCT/US2004/01193, filed Jan. 16, 2004. An iRNA agent can include a non-naturally occurring base, such as the bases described in co-owned PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in co-owned PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in co-owned PCT Application No. PCT/US2004/07070 filed on Mar. 8, 2004.

An iRNA agent can include ligand-conjugated monomer subunits and monomers for oligonucleotide synthesis. Exemplary monomers are described in co-owned U.S. application Ser. No. 10/916,185, filed on Aug. 10, 2004.

An iRNA agent can have a ZXY structure, such as is described in co-owned PCT Application No. PCT/US2004/07070 filed on Mar. 8, 2004.

An iRNA agent can be complexed with an amphipathic moiety. Exemplary amphipathic moieties for use with iRNA agents are described in co-owned PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070 filed on Mar. 8, 2004.

Enhanced Nuclease Resistance

An iRNA agent, e.g., an iRNA agent that targets RSV, can have enhanced resistance to nucleases.

For increased nuclease resistance and/or binding affinity to the target, an iRNA agent, e.g., the sense and/or antisense strands of the iRNA agent, can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)$ AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e., deoxyribose sugars, which are of particular relevance to the overhang portions of partially ds RNA); halo (e.g., fluoro); amino (e.g., $NH_2$; alkylamino, dialkylamino, heterocyclyl, arylamino, diaryl amino, heteroaryl amino, diheteroaryl amino, or amino acid); NH(CH2CH2NH)nCH2CH2-AMINE (AMINE=NH2; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substituents are 2'O-methyl (OMe), 2'-methoxyethyl, 2'-OCH3, 2'-O-allyl, 2'-C-allyl, and 2'-fluoro (2'F). In one aspect, both 2'OMe and 2'F are used as substituents on an iRNA agent.

One way to increase resistance is to identify cleavage sites and modify such sites to inhibit cleavage, as described in co-owned U.S. Application No. 60/559,917, filed on May 4, 2004. For example, the dinucleotides 5'-UA-3', 5' UG 3',5'-CA-3', 5' UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of such dinucleotides. In certain embodiments, all the pyrimidines of an iRNA agent carry a 2'-modification, and the iRNA agent therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

In one aspect, a hydroxy pyrollidine (hp) linker provides exonuclease protection.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications that can inhibit hybridization are preferably used only in terminal regions, and more preferably not at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In most cases, the NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (as described in Elbashir et al., 2001, Genes and Dev. 15: 188, hereby incorporated by reference). Cleavage of the target occurs about in the middle of a 20 or 21 nt antisense strand, or about 10 or 11 nucleotides upstream of the first nucleotide on the target mRNA which is complementary to the antisense strand. As used herein cleavage site refers to the nucleotides on either side of the site of cleavage, on the target mRNA or on the iRNA agent strand which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

Tethered Ligands

The properties of an iRNA agent, including its pharmacological properties, can be influenced and tailored, for example, by the introduction of ligands, e.g., tethered ligands.

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_nNH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic molecules, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g., low density lipoprotein (LDL), or albumins, e.g., human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule preferably binds a serum protein, e.g., human serum albumin (HSA). Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

5'-Phosphate Modifications

In preferred embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)$_2$(O)P—O-5'); 5'-diphosphate ((HO)2(O)P—O—P(HO)(O)—O-5'); 5'-triphosphate ((HO)2(O)P-β-(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Delivery of iRNA Agents to Tissues and Cells

Formulation

The iRNA agents described herein can be formulated for administration to a subject, preferably for administration locally to the lungs and nasal passage (respiratory tissues) via inhalation or intranasal administration, or parenterally, e.g., via injection.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water, this form being the preferred form for administration via inhalation.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA agent preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are directed to the same virus but different target sequences. In another embodiment, each iRNA agents is directed to a different virus. As demonstrated in the Example, more than one virus can be inhibited by co-administering two iRNA agents simultaneously, or at closely time intervals, each one directed to one of the viruses being treated.

Treatment Methods and Routes of Delivery

A composition that includes an iRNA agent of the present invention, e.g., an iRNA agent that targets RSV, can be delivered to a subject by a variety of routes. The pharmaceutical compositions of the present invention may be administered in a number of ways depending upon whether local or systemic treatment is desired and upon the area to be treated. Administration may be topical (including intranasal or intrapulmonary), oral or parenteral. Exemplary routes include inhalation, intravenous, nasal, or oral delivery.

In general, the delivery of the iRNA agents of the present invention is done to achieve delivery into the subject to the site of infection. This objective can be achieved through either a local (i.e., topical) administration to the lungs or nasal passage, e.g., into the respiratory tissues via inhalation, nebulization or intranasal administration, or via systemic administration, e.g., parental administration. Parenteral administration includes intravenous drip, subcutaneous, intraperitoneal or intramuscular injection. The preferred means of administering the iRNA agents of the present invention is through direct topical administration to the lungs and/or nasal passage by inhalation of an aerosolized liquid such as a nebulized mist or a nasal spray.

An iRNA agent can be incorporated into pharmaceutical compositions suitable for administration. For example, compositions can include one or more iRNA agents and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Formulations for inhalation, intranasal, or parenteral administration are well known in the art. Such formulations may include sterile aqueous solutions which may also contain buffers, diluents and other suitable additives, an example being PBS or Dextrose 5% in water. For intravenous use, the total concentration of solutes should be controlled to render the preparation isotonic.

The active compounds disclosed herein are preferably administered to the lung(s) or nasal passage of a subject by any suitable means. Active compounds may be administered by administering an aerosol suspension of respirable particles comprised of the active compound or active compounds, which the subject inhales. The active compound can be aerosolized in a variety of forms, such as, but not limited to, dry powder inhalants, metered dose inhalants, or liquid/liquid suspensions. The respirable particles may be liquid or solid. The particles may optionally contain other therapeutic ingredients such as amiloride, benzamil or phenamil, with the selected compound included in an amount effective to inhibit the reabsorption of water from airway mucous secretions, as described in U.S. Pat. No. 4,501,729.

The particulate pharmaceutical composition may optionally be combined with a carrier to aid in dispersion or transport. A suitable carrier such as a sugar (i.e., dextrose, lactose, sucrose, trehalose, mannitol) may be blended with the active compound or compounds in any suitable ratio (e.g., a 1 to 1 ratio by weight).

In one embodiment, an active compound is topically administered by inhalation. As used in this specification, administration by "inhalation" generally refers to the inspiration of particles comprised of the active compound that are of respirable size, that is, particles of a size sufficiently small to pass through the mouth or nose and larynx upon inhalation and into the bronchi and alveoli of the lungs. In general, particles ranging from about 1 to 10 microns in size (more particularly, less than about 5 microns in size) are respirable and suitable for administration by inhalation.

In another embodiment, an active compound is topically delivered by intranasal administration. As used in this specification, "intranasal" administration refers to administration of a dosage form formulated and delivered to topically treat the nasal epithelium. Particles or droplets used for intranasal administration generally have a diameter that is larger than those used for administration by inhalation. For intranasal administration, a particle size in the range of 10-500 microns is preferred to ensure retention in the nasal cavity. Particles of non-respirable size which are included in the aerosol tend to deposit in the throat and be swallowed, and the quantity of non-respirable particles in the aerosol is preferably minimized.

Liquid pharmaceutical compositions of active compound for producing an aerosol can be prepared by combining the active compound with a suitable vehicle, such as sterile pyrogen free water. In certain embodiments hypertonic saline solutions are used to carry out the present invention. These are preferably sterile, pyrogen-free solutions, comprising from one to fifteen percent (by weight) of a physiologically acceptable salt, and more preferably from three to seven percent by weight of the physiologically acceptable salt.

Aerosols of liquid particles comprising the active compound may be produced by any suitable means, such as with a pressure-driven jet nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation.

Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic, but may be hypertonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate therapeutic aerosol generator. Aerosol generators for administering solid particulate therapeutics to a subject produce particles which are respirable and generate a volume of aerosol containing a predetermined metered dose of a therapeutic at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

A second type of illustrative aerosol generator comprises a metered dose inhaler. Metered dose inhalers are pressurized aerosol dispensers, typically containing a suspension or solution formulation of the active ingredient in a liquefied propellant. During use these devices discharge the formulation through a valve adapted to deliver a metered volume, typically from 10 µl to 200 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidant and suitable flavoring agents.

Administration can be provided by the subject or by another person, e.g., a caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent. The medication can be provided in measured doses or in a dispenser which delivers a metered dose.

The term "therapeutically effective amount" is the amount present in the composition that is needed to provide the desired level of drug in the subject to be treated to give the anticipated physiological response. In one embodiment, therapeutically effective amounts of two or more iRNA agents, each one directed to a different respiratory virus, e.g., RSV, and FIV are administered concurrently to a subject.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The term "co-administration" refers to administering to a subject two or more agents, and in particular two or more iRNA agents. The agents can be contained in a single pharmaceutical composition and be administered at the same time, or the agents can be contained in separate formulation and administered serially to a subject. So long as the two agents can be detected in the subject at the same time, the two agents are said to be co-administered.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-beta-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

Dosage.

An iRNA agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of iRNA agent (e.g., about 4.4×10$^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of iRNA agent per kg of bodyweight. The unit dose, for example, can be administered by an inhaled dose or nebulization or by injection. In one example, dosage ranges of 0.02-25 mg/kg is used.

Delivery of an iRNA agent directly to the lungs or nasal passage can be at a dosage on the order of about 1 mg to about 150 mg/nasal passage, such as, e.g., 25, 50, 75, 100 or 150 mg/nasal passage.

The dosage can be an amount effective to treat or prevent a disease or disorder.

In one embodiment, the unit dose is administered once a day. In other usage, a unit dose is administered twice the first day and then daily. Alternatively, unit dosing can be less than once a day, e.g., less than every 2, 4, 8 or 30 days. In another embodiment, the unit dose is not administered with a frequency (e.g., not a regular frequency). For example, the unit dose may be administered a single time. Because iRNA agent mediated silencing can persist for several days after administering the iRNA agent composition, in many instances, it is possible to administer the composition with a frequency of less than once per day, or, for some instances, only once for the entire therapeutic regimen.

In one embodiment, a subject is administered an initial dose, and one or more maintenance doses of an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 µg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5-14 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

In one embodiment, the iRNA agent pharmaceutical composition includes a plurality of iRNA agent species. The iRNA agent species can have sequences that are non-overlapping and non-adjacent with respect to a naturally occurring target sequence, e.g., a target sequence of the RSV gene. In another embodiment, the plurality of iRNA agent species is specific for different naturally occurring target genes. For example, an iRNA agent that targets the P protein gene of RSV can be present in the same pharmaceutical composition as an iRNA agent that targets a different gene, for example the N protein gene. In another embodiment, the iRNA agents are specific for different viruses, e.g., RSV.

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g., nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. It will also be appreciated that the effective dosage of an iRNA agent such as an siRNA agent used for treatment may increase or decrease over the course of a particular treatment. Changes in dosage may result and become apparent from the results of diagnostic assays. For example, the subject can be monitored after administering an iRNA agent composition. Based on information from the monitoring, an additional amount of the iRNA agent composition can be administered.

Generally speaking, administration of the therapeutic compositions of the invention can occur in a hospital or clinical setting ("inpatient management"), or can occur in an "outpatient" setting, e.g., at the patient's home. Inpatient treatment would be most appropriate where the patient is suffering from severe symptoms of RSV, including apnea, respiratory distress, low oxygen intake, and/or hydration or starvation. Depending on the patient's age and ability, the patient can administer the therapeutic compositions to himself or herself. Treatment with the therapeutic compositions of the invention may be accompanied by, e.g., hydration, steam, bronchodilators (e.g., albuteraol), anti-fever or anti-inflammatory medications (e.g., Tylenol) and the intake of food, liquids, and/or vitamin supplements. In addition, and typically in an inpatient setting, the patient may also receive oxygen treatment, intravenous hydration, and treatment with steroids.

The invention is further illustrated by the following examples, which should not be construed as further limiting.

EXAMPLES

Example 1

Designing Antiviral siRNAs Against RSV mRNA siRNA against RSV P, N and L mRNA were synthesized chemically using known procedures. The siRNA sequences and some inhibition cross-subtype activity and 1050 values as described below are listed in Tables 1a, 1b, and 1c.

TABLE 1a

| \multicolumn{7}{|c|}{RSV L Gene siRNA sequences} |
| Actual start | Whitehead Start Pos | SEQ ID NO. | Sense | SEQ ID NO. | Antisense | RSV L gene duplex |
| --- | --- | --- | --- | --- | --- | --- |
| 3 | 1 | 3 | GGAUCCCAUUAUUAAUGGAdTdT | 117 | UCCAUUAAUAAUGGGAUCCdTdT | AL-DP-2024 |
| 4 | 2 | 4 | GAUCCCAUUAUUAAUGGAAdTdT | 118 | UUCCAUUAAUAAUGGGAUCdTdT | AL-DP-2026 |
| 49 | 47 | 5 | AGUUAUUUAAAAGGUGUUUAdTdT | 119 | UAACACCUUUUAAAUAACUdTdT | AL-DP-2116 |
| 50 | 48 | 6 | GUUAUUUAAAAGGUGUUUAUdTdT | 120 | AUAACACCUUUUAAAUAACdTdT | AL-DP-2117 |
| 53 | 51 | 7 | AUUUAAAAGGUGUUUAUCUCdTdT | 121 | GAGAUAACACCUUUUAAAUdTdT | AL-DP-2118 |
| 55 | 53 | 8 | UUAAAAGGUGUUUAUCUCUUdTdT | 122 | AAGAGAUAACACCUUUUAAdTdT | AL-DP-2119 |
| 156 | 154 | 9 | AAGUCCACUACUAGAGCAUdTdT | 123 | AUGCUCUAGUAGUGGACUUdTdT | AL-DP-2027 |
| 157 | 155 | 10 | AGUCCACUACUAGAGCAUAdTdT | 124 | UAUGCUCUAGUAGUGGACUdTdT | AL-DP-2028 |
| 158 | 156 | 11 | GUCCACUACUAGAGCAUAUdTdT | 125 | AUAUGCUCUAGUAGUGGACdTdT | AL-DP-2029 |
| 159 | 157 | 12 | UCCACUACUAGAGCAUAUGdTdT | 126 | CAUAUGCUCUAGUAGUGGAdTdT | AL-DP-2030 |
| 341 | 339 | 13 | GAAGAGCUAUAGAAAUAAGdTdT | 127 | CUUAUUUCUAUAGCUCUUCdTdT | AL-DP-2120 |
| 344 | 342 | 14 | GAGCUAUAGAAAUAAGUGAdTdT | 128 | UCACUUAUUUCUAUAGCUCdTdT | AL-DP-2121 |
| 347 | 345 | 15 | CUAUAGAAAUAAGUGAUGUdTdT | 129 | ACAUCACUUAUUUCUAUAGdTdT | AL-DP-2031 |
| 554 | 552 | 16 | UCAAAACAACACUCUUGAAdTdT | 130 | UUCAAGAGUGUUGUUUUGAdTdT | AL-DP-2122 |

TABLE 1a-continued

| 1004 | 1002 | 17 | UAGAGGGAUUUAUUAUGUCdTdT | 131 | GACAUAAUAAAUCCCUCUAdTdT | AL-DP-2123 |
| --- | --- | --- | --- | --- | --- | --- |
| 1408 | 1406 | 18 | AUAAAGGGUUUGUAAAUAdTdT | 132 | UAUUUACAAACCCUUUUAUdTdT | AL-DP-2124 |
| 1867 | 1865 | 19 | CUCAGUGUAGGUAGAAUGUdTdT | 133 | ACAUUCUACCUACACUGAGdTdT | AL-DP-2032 |
| 1868 | 1866 | 20 | UCAGUGUAGGUAGAAUGUUdTdT | 134 | AACAUUCUACCUACACUGAdTdT | AL-DP-2033 |
| 1869 | 1867 | 21 | CAGUGUAGGUAGAAUGUUUdTdT | 135 | AAACAUUCUACCUACACUGdTdT | AL-DP-2034 |
| 1870 | 1868 | 22 | AGUGUAGGUAGAAUGUUUGdTdT | 136 | CAAACAUUCUACCUACACUdTdT | AL-DP-2112 |
| 1871 | 1869 | 23 | GUGUAGGUAGAAUGUUUGCdTdT | 137 | GCAAACAUUCUACCUACACdTdT | AL-DP-2113 |
| 1978 | 1976 | 24 | ACAAGAUAUGGUGAUCUAGdTdT | 138 | CUAGAUCACCAUAUCUUGUdTdT | AL-DP-2035 |
| 2104 | 2102 | 25 | AGCAAAUUCAAUCAAGCAUdTdT | 139 | AUGCUUGAUUGAAUUUGCUdTdT | AL-DP-2036 |
| 2105 | 2103 | 26 | GCAAAUUCAAUCAAGCAUUdTdT | 140 | AAUGCUUGAUUGAAUUUGCdTdT | AL-DP-2037 |
| 2290 | 2288 | 27 | GAUGAACAAAGUGGAUUAUdTdT | 141 | AUAAUCCACUUUGUUCAUCdTdT | AL-DP-2038 |
| 2384 | 2382 | 28 | UAAUAUCUCUCAAAGGGAAdTdT | 142 | UUCCCUUUGAGAGAUAUUAdTdT | AL-DP-2125 |
| 2386 | 2384 | 29 | AUAUCUCUCAAAGGGAAAUdTdT | 143 | AUUUCCCUUUGAGAGAUAUdTdT | AL-DP-2126 |
| 2387 | 2385 | 30 | UAUCUCUCAAAGGGAAAUUdTdT | 144 | AAUUUCCCUUUGAGAGAUAdTdT | AL-DP-2127 |
| 2485 | 2483 | 31 | CAUGCUCAAGCAGAUUAUUdTdT | 145 | AAUAAUCUGCUUGAGCAUGdTdT | AL-DP-2039 |
| 2487 | 2485 | 32 | UGCUCAAGCAGAUUAUUUGdTdT | 146 | CAAAUAAUCUGCUUGAGCAdTdT | AL-DP-2040 |
| 2507 | 2505 | 33 | UAGCAUUAAAUAGCCUUAAdTdT | 147 | UUAAGGCUAUUUAAUGCUAdTdT | AL-DP-2041 |
| 2508 | 2506 | 34 | AGCAUUAAAUAGCCUUAAAdTdT | 148 | UUUAAGGCUAUUUAAUGCUdTdT | AL-DP-2114 |
| 2509 | 2507 | 35 | GCAUUAAAUAGCCUUAAAUdTdT | 149 | AUUUAAGGCUAUUUAAUGCdTdT | AL-DP-2042 |
| 2510 | 2508 | 36 | CAUUAAAUAGCCUUAAAUUdTdT | 150 | AAUUUAAGGCUAUUUAAUGdTdT | AL-DP-2043 |
| 2765 | 2763 | 37 | UAUUAUGCAGUUUAAUAUUdTdT | 151 | AAUAUUAAACUGCAUAAUAdTdT | AL-DP-2044 |
| 2767 | 2765 | 38 | UUAUGCAGUUUAAUAUUUAdTdT | 152 | UAAAUAUUAAACUGCAUAAdTdT | AL-DP-2045 |
| 3283 | 3281 | 39 | AAAAGUGCACAACAUUAUAdTdT | 153 | UAUAAUGUUGUGCACUUUUdTdT | AL-DP-2128 |
| 3284 | 3282 | 40 | AAAGUGCACAACAUUAUACdTdT | 154 | GUAUAAUGUUGUGCACUUUdTdT | AL-DP-2046 |
| 3338 | 3336 | 41 | AUAUAGAACCUACAUAUCCdTdT | 155 | GGAUAUGUAGGUUCUAUAUdTdT | AL-DP-2047 |
| 3339 | 3337 | 42 | UAUAGAACCUACAUAUCCUdTdT | 156 | AGGAUAUGUAGGUUCUAUAdTdT | AL-DP-2048 |
| 3365 | 3363 | 43 | UAAGAGUUGUUUAUGAAAGdTdT | 157 | CUUUCAUAAACAACUCUUAdTdT | AL-DP-2129 |
| 4021 | 4019 | 44 | ACAGUCAGUAGUAGACCAUdTdT | 158 | AUGGUCUACUACUGACUGUdTdT | AL-DP-2049 |
| 4022 | 4020 | 45 | CAGUCAGUAGUAGACCAUGdTdT | 159 | CAUGGUCUACUACUGACUGdTdT | AL-DP-2050 |
| 4023 | 4021 | 46 | AGUCAGUAGUAGACCAUGUdTdT | 160 | ACAUGGUCUACUACUGACUdTdT | AL-DP-2051 |
| 4024 | 4022 | 47 | GUCAGUAGUAGACCAUGUGdTdT | 161 | CACAUGGUCUACUACUGACdTdT | AL-DP-2052 |
| 4025 | 4023 | 48 | UCAGUAGUAGACCAUGUGAdTdT | 162 | UCACAUGGUCUACUACUGAdTdT | AL-DP-2053 |
| 4037 | 4035 | 49 | CAUGUGAAUUCCUGCAUCdTdT | 163 | GAUGCAGGGAAUUCACAUGdTdT | AL-DP-2054 |
| 4038 | 4036 | 50 | AUGUGAAUUCCUGCAUCAdTdT | 164 | UGAUGCAGGGAAUUCACAUdTdT | AL-DP-2055 |
| 4039 | 4037 | 51 | UGUGAAUUCCUGCAUCAAdTdT | 165 | UUGAUGCAGGGAAUUCACAdTdT | AL-DP-2056 |
| 4040 | 4038 | 52 | GUGAAUUCCUGCAUCAAUdTdT | 166 | AUUGAUGCAGGGAAUUCACdTdT | AL-DP-2115 |
| 4043 | 4041 | 53 | AAUUCCCUGCAUCAAUACCdTdT | 167 | GGUAUUGAUGCAGGGAAUUdTdT | AL-DP-2057 |
| 4051 | 4049 | 54 | GCAUCAAUACCAGCUUAUAdTdT | 168 | UAUAAGCUGGUAUUGAUGCdTdT | AL-DP-2058 |
| 4052 | 4050 | 55 | CAUCAAUACCAGCUUAUAGdTdT | 169 | CUAUAAGCUGGUAUUGAUGdTdT | AL-DP-2059 |
| 4057 | 4055 | 56 | AUACCAGCUUAUAGAACAAdTdT | 170 | UUGUUCUAUAAGCUGGUAUdTdT | AL-DP-2060 |

TABLE 1a-continued

| | | | | | | |
|---|---|---|---|---|---|---|
| 4058 | 4056 | 57 | UACCAGCUUAUAGAACAACAdTdT | 171 | GUUGUUCUAUAAGCUGGUAdTdT | AL-DP-2061 |
| 4059 | 4057 | 58 | ACCAGCUUAUAGAACAACAdTdT | 172 | UGUUGUUCUAUAAGCUGGUdTdT | AL-DP-2062 |
| 4060 | 4058 | 59 | CCAGCUUAUAGAACAACAAdTdT | 173 | UUGUUGUUCUAUAAGCUGGdTdT | AL-DP-2063 |
| 4061 | 4059 | 60 | CAGCUUAUAGAACAACAAAdTdT | 174 | UUUGUUGUUCUAUAAGCUGdTdT | AL-DP-2064 |
| 4067 | 4065 | 61 | AUAGAACAACAAAUUAUCAdTdT | 175 | UGAUAAUUUGUUGUUCUAUdTdT | AL-DP-2065 |
| 4112 | 4110 | 62 | UAUUAACAGAAAAGUAUGGdTdT | 176 | CCAUACUUUUCUGUUAAUAdTdT | AL-DP-2130 |
| 4251 | 4249 | 63 | UGAGAUACAUUUGAUGAAAdTdT | 177 | UUUCAUCAAAUGUAUCUCAdTdT | AL-DP-2066 |
| 4252 | 4250 | 64 | GAGAUACAUUUGAUGAAACdTdT | 178 | GUUUCAUCAAAUGUAUCUCdTdT | AL-DP-2067 |
| 4254 | 4252 | 65 | GAUACAUUUGAUGAAACCUdTdT | 179 | AGGUUUCAUCAAAUGUAUCdTdT | AL-DP-2068 |
| 4255 | 4253 | 66 | AUACAUUUGAUGAAACCUCdTdT | 180 | GAGGUUUCAUCAAAUGUAUdTdT | AL-DP-2069 |
| 4256 | 4254 | 67 | UACAUUUGAUGAAACCUCCdTdT | 181 | GGAGGUUUCAUCAAAUGUAdTdT | AL-DP-2074 |
| 4313 | 4311 | 68 | AAGUGAUACAAAAACAGCAdTdT | 182 | UGCUGUUUUUGUAUCACUUdTdT | AL-DP-2131 |
| 4314 | 4312 | 69 | AGUGAUACAAAAACAGCAUdTdT | 183 | AUGCUGUUUUUGUAUCACUdTdT | AL-DP-2132 |
| 4316 | 4314 | 70 | UGAUACAAAAACAGCAUAUdTdT | 184 | AUAUGCUGUUUUUGUAUCAdTdT | AL-DP-2133 |
| 4473 | 4471 | 71 | UUUAAGUACUAAUUUAGCUdTdT | 185 | AGCUAAAUUAGUACUUAAAdTdT | AL-DP-2075 |
| 4474 | 4472 | 72 | UUAAGUACUAAUUUAGCUGdTdT | 186 | CAGCUAAAUUAGUACUUAAdTdT | AL-DP-2076 |
| 4475 | 4473 | 73 | UAAGUACUAAUUUAGCUGGdTdT | 187 | CCAGCUAAAUUAGUACUUAdTdT | AL-DP-2077 |
| 4476 | 4474 | 74 | AAGUACUAAUUUAGCUGGAdTdT | 188 | UCCAGCUAAAUUAGUACUUdTdT | AL-DP-2078 |
| 4477 | 4475 | 75 | AGUACUAAUUUAGCUGGACdTdT | 189 | GUCCAGCUAAAUUAGUACUdTdT | AL-DP-2079 |
| 4478 | 4476 | 76 | GUACUAAUUUAGCUGGACAdTdT | 190 | UGUCCAGCUAAAUUAGUACdTdT | AL-DP-2080 |
| 4480 | 4478 | 77 | ACUAAUUUAGCUGGACAUUdTdT | 191 | AAUGUCCAGCUAAAUUAGUdTdT | AL-DP-2081 |
| 4483 | 4481 | 78 | AAUUUAGCUGGACAUUGGAdTdT | 192 | UCCAAUGUCCAGCUAAAUUdTdT | AL-DP-2082 |
| 4484 | 4482 | 79 | AUUUAGCUGGACAUUGGAUdTdT | 193 | AUCCAAUGUCCAGCUAAAUdTdT | AL-DP-2083 |
| 4486 | 4484 | 80 | UUAGCUGGACAUUGGAUUCdTdT | 194 | GAAUCCAAUGUCCAGCUAAdTdT | AL-DP-2084 |
| 4539 | 4537 | 81 | UUUUGAAAAGAUUGGGGAdTdT | 195 | UCCCCAAUCUUUUUCAAAAdTdT | AL-DP-2134 |
| 4540 | 4538 | 82 | UUUGAAAAGAUUGGGGAGdTdT | 196 | CUCCCCAAUCUUUUUCAAAdTdT | AL-DP-2135 |
| 4542 | 4540 | 83 | UGAAAAGAUUGGGGAGAGdTdT | 197 | CUCUCCCCAAUCUUUUUCAdTdT | AL-DP-2136 |
| 4543 | 4541 | 84 | GAAAAGAUUGGGGAGAGGdTdT | 198 | CCUCUCCCCAAUCUUUUUCdTdT | AL-DP-2137 |
| 4671 | 4669 | 85 | UAUGAACACUUCAGAUCUUdTdT | 199 | AAGAUCUGAAGUGUUCAUAdTdT | AL-DP-2085 |
| 4672 | 4670 | 86 | AUGAACACUUCAGAUCUUCdTdT | 200 | GAAGAUCUGAAGUGUUCAUdTdT | AL-DP-2086 |
| 4867 | 4865 | 87 | UGCCCUUGGGUUGUUAACAdTdT | 201 | UGUUAACAACCCAAGGGCAdTdT | AL-DP-2087 |
| 4868 | 4866 | 88 | GCCCUUGGGUUGUUAACAUdTdT | 202 | AUGUUAACAACCCAAGGGCdTdT | AL-DP-2088 |
| 5544 | 5542 | 89 | UAUAGCAUUCAUAGGUGAAdTdT | 203 | UUCACCUAUGAAUGCUAUAdTdT | AL-DP-2089 |
| 5545 | 5543 | 90 | AUAGCAUUCAUAGGUGAAGdTdT | 204 | CUUCACCUAUGAAUGCUAUdTdT | AL-DP-2090 |
| 5546 | 5544 | 91 | UAGCAUUCAUAGGUGAAGGdTdT | 205 | CCUUCACCUAUGAAUGCUAdTdT | AL-DP-2091 |
| 5550 | 5548 | 92 | AUUCAUAGGUGAAGGAGCAdTdT | 206 | UGCUCCUUCACCUAUGAAUdTdT | AL-DP-2092 |
| 5640 | 5638 | 93 | UUGCAAUGAUCAUAGUUUAdTdT | 207 | UAAACUAUGAUCAUUGCAAdTdT | AL-DP-2093 |
| 5641 | 5639 | 94 | UGCAAUGAUCAUAGUUUACdTdT | 208 | GUAAACUAUGAUCAUUGCAdTdT | AL-DP-2094 |
| 5642 | 5640 | 95 | GCAAUGAUCAUAGUUUACCdTdT | 209 | GGUAAACUAUGAUCAUUGCdTdT | AL-DP-2095 |
| 5643 | 5641 | 96 | CAAUGAUCAUAGUUUACCUdTdT | 210 | AGGUAAACUAUGAUCAUUGdTdT | AL-DP-2096 |

TABLE 1a-continued

| | | | | | | |
|---|---|---|---|---|---|---|
| 5644 | 5642 | 97 | AAUGAUCAUAGUUUACCUAdTdT | 211 | UAGGUAAACUAUGAUCAUUdTdT | AL-DP-2097 |
| 5645 | 5643 | 98 | AUGAUCAUAGUUUACCUAUdTdT | 212 | AUAGGUAAACUAUGAUCAUdTdT | AL-DP-2098 |
| 5647 | 5645 | 99 | GAUCAUAGUUUACCUAUUGdTdT | 213 | CAAUAGGUAAACUAUGAUCdTdT | AL-DP-2138 |
| 5648 | 5646 | 100 | AUCAUAGUUUACCUAUUGAdTdT | 214 | UCAAUAGGUAAACUAUGAUdTdT | AL-DP-2139 |
| 5649 | 5647 | 101 | UCAUAGUUUACCUAUUGAGdTdT | 215 | CUCAAUAGGUAAACUAUGAdTdT | AL-DP-2140 |
| 5650 | 5648 | 102 | CAUAGUUUACCUAUUGAGUdTdT | 216 | ACUCAAUAGGUAAACUAUGdTdT | AL-DP-2099 |
| 5651 | 5649 | 103 | AUAGUUUACCUAUUGAGUUdTdT | 217 | AACUCAAUAGGUAAACUAUdTdT | AL-DP-2100 |
| 5752 | 5750 | 104 | CAUUGGUCUUAUUUACAUAdTdT | 218 | UAUGUAAAUAAGACCAAUGdTdT | AL-DP-2101 |
| 5754 | 5752 | 105 | UUGGUCUUAUUUACAUAUAdTdT | 219 | UAUAUGUAAAUAAGACCAAdTdT | AL-DP-2102 |
| 5755 | 5753 | 106 | UGGUCUUAUUUACAUAUAAdTdT | 220 | UUAUAUGUAAAUAAGACCAdTdT | AL-DP-2103 |
| 5756 | 5754 | 107 | GGUCUUAUUUACAUAUAAAdTdT | 221 | UUUAUAUGUAAAUAAGACCdTdT | AL-DP-2141 |
| 5919 | 5917 | 108 | AUAUCAUGCUCAAGAUGAUdTdT | 222 | AUCAUCUUGAGCAUGAUAUdTdT | AL-DP-2142 |
| 5920 | 5918 | 109 | UAUCAUGCUCAAGAUGAUAdTdT | 223 | UAUCAUCUUGAGCAUGAUAdTdT | AL-DP-2104 |
| 5934 | 5932 | 110 | UGAUAUUGAUUUCAAAUUAdTdT | 224 | UAAUUUGAAAUCAAUAUCAdTdT | AL-DP-2105 |
| 6016 | 6014 | 111 | UACUUAGUCCUUACAAUAGdTdT | 225 | CUAUUGUAAGGACUAAGUAdTdT | AL-DP-2106 |
| 6019 | 6017 | 112 | UUAGUCCUUACAAUAGGUCdTdT | 226 | GACCUAUUGUAAGGACUAAdTdT | AL-DP-2107 |
| 6020 | 6018 | 113 | UAGUCCUUACAAUAGGUCCdTdT | 227 | GGACCUAUUGUAAGGACUAdTdT | AL-DP-2108 |
| 6252 | 6250 | 114 | AUAUUCUAUAGCUGGACGUdTdT | 228 | ACGUCCAGCUAUAGAAUAUdTdT | AL-DP-2109 |
| 6253 | 6251 | 115 | UAUUCUAUAGCUGGACGUAdTdT | 229 | UACGUCCAGCUAUAGAAUAdTdT | AL-DP-2110 |
| 6254 | 6252 | 116 | AUUCUAUAGCUGGACGUAAdTdT | 230 | UUACGUCCAGCUAUAGAAUdTdT | AL-DP-2111 |

RSV L Gene siRNA Activity

| RSV L gene duplex | % inh RSV A2 (5 nM) | % inh RSV A2 500 pM | % inh RSV A2 50 pM | % inh RSV A2 5pM | % inh RSV B (5 nM) |
|---|---|---|---|---|---|
| AL-DP-2038 | 11 | | | | |
| AL-DP-2031 | 15 | | | | |
| AL-DP-2045 | 15 | | | | |
| AL-DP-2050 | 15 | | | | |
| AL-DP-2056 | 16 | | | | |
| AL-DP-2049 | 24 | | | | |
| AL-DP-2026 | 82 | | | | |
| AL-DP-2033 | 84 | | | | |
| AL-DP-2048 | 84 | | | | |
| AL-DP-2027 | 86 | | | | |
| AL-DP-2030 | 86 | | | | |
| AL-DP-2034 | 86 | | | | |
| AL-DP-2058 | 86 | | | | |
| AL-DP-2066 | 86 | | | | |
| AL-DP-2036 | 87 | | | | |
| AL-DP-2039 | 87 | | | | |
| AL-DP-2047 | 87 | | | | |
| AL-DP-2051 | 87 | | | | |

TABLE 1a-continued

| | | | | | |
|---|---|---|---|---|---|
| AL-DP-2040 | 88 | | | | |
| AL-DP-2055 | 88 | | | | |
| AL-DP-2061 | 88 | | | | |
| AL-DP-2029 | 89 | | | | |
| AL-DP-2035 | 89 | | | | |
| AL-DP-2069 | 89 | | | | |
| AL-DP-2028 | 90 | | | | |
| AL-DP-2032 | 90 | | | | |
| AL-DP-2063 | 90 | | | | |
| AL-DP-2037 | 91 | | | | |
| AL-DP-2059 | 91 | | | | |
| AL-DP-2065 | 91 | | | | |
| AL-DP-2024 | 92 | | | | |
| AL-DP-2053 | 92 | 84 | 79 | 76 | 74 |
| AL-DP-2060 | 92 | | | | |
| AL-DP-2067 | 92 | | | | |
| AL-DP-2068 | 93 | | | | |
| AL-DP-2046 | 94 | 94 | 91 | 91 | 93 |
| AL-DP-2057 | 94 | 91 | 86 | 79 | 69 |
| AL-DP-2064 | 94 | 86 | 76 | 67 | 83 |
| AL-DP-2062 | 95 | 79 | 78 | 72 | 94 |
| AL-DP-2041 | 96 | 76 | 73 | 69 | 94 |
| AL-DP-2042 | 96 | 98 | 97 | 97 | 90 |
| AL-DP-2052 | 96 | 84 | 76 | 69 | 87 |
| AL-DP-2043 | 97 | 86 | 79 | 75 | 94 |
| AL-DP-2044 | 97 | 79 | 72 | 67 | 84 |
| AL-DP-2054 | 97 | 79 | 78 | 69 | 96 |

TABLE 1b

RSV P Gene siRNA sequences

| Actual start | Start Pos | SEQ ID NO. | Sense | SEQ ID NO. | Antisense | RSVP gene duplex ID # |
|---|---|---|---|---|---|---|
| 55 | 53 | 231 | AAAUUCCUAGAAUCAAUAAdTdT | 250 | UUAUUGAUUCUAGGAAUUUdTdT | AL-DP-2000 |
| 56 | 54 | 232 | AAUUCCUAGAAUCAAUAAAdTdT | 251 | UUUAUUGAUUCUAGGAAUUdTdT | AL-DP-2001 |
| 58 | 56 | 233 | UUCCUAGAAUCAAUAAAGGdTdT | 252 | CCUUUAUUGAUUCUAGGAAdTdT | AL-DP-2002 |
| 59 | 57 | 234 | UCCUAGAAUCAAUAAAGGGdTdT | 253 | CCCUUUAUUGAUUCUAGGAdTdT | AL-DP-2003 |
| 61 | 59 | 235 | CUAGAAUCAAUAAAGGGCAdTdT | 254 | UGCCCUUUAUUGAUUCUAGdTdT | AL-DP-2004 |
| 322 | 320 | 236 | ACAUUUGAUAACAAUGAAGdTdT | 255 | CUUCAUUGUUAUCAAAUGUdTdT | AL-DP-2005 |
| 323 | 321 | 237 | CAUUUGAUAACAAUGAAGAdTdT | 256 | UCUUCAUUGUUAUCAAAUGdTdT | AL-DP-2006 |
| 324 | 322 | 238 | AUUUGAUAACAAUGAAGAAdTdT | 257 | UUCUUCAUUGUUAUCAAAUdTdT | AL-DP-2007 |

TABLE 1b-continued

| | | | | | | |
|---|---|---|---|---|---|---|
| 325 | 323 | 239 | UUUGAUAACAAUGAAGAAGdTdT | 258 | CUUCUUCAUUGUUAUCAAAdTdT | AL-DP-2008 |
| 426 | 424 | 240 | AAGUGAAAUACUAGGAAUGdTdT | 259 | CAUUCCUAGUAUUUCACUUdTdT | AL-DP-2009 |
| 427 | 425 | 241 | AGUGAAAUACUAGGAAUGCdTdT | 260 | GCAUUCCUAGUAUUUCACUdTdT | AL-DP-2010 |
| 428 | 426 | 242 | GUGAAAUACUAGGAAUGCUdTdT | 261 | AGCAUUCCUAGUAUUUCACdTdT | AL-DP-2011 |
| 429 | 427 | 243 | UGAAAUACUAGGAAUGCUUdTdT | 262 | AAGCAUUCCUAGUAUUUCAdTdT | AL-DP-2012 |
| 430 | 428 | 244 | GAAAUACUAGGAAUGCUUCdTdT | 263 | GAAGCAUUCCUAGUAUUUCdTdT | AL-DP-2013 |
| 431 | 429 | 245 | AAAUACUAGGAAUGCUUCAdTdT | 264 | UGAAGCAUUCCUAGUAUUUdTdT | AL-DP-2014 |
| 550 | 548 | 246 | GAAGCAUUAAUGACCAAUGdTdT | 265 | CAUUGGUCAUUAAUGCUUCdTdT | AL-DP-2015 |
| 551 | 549 | 247 | AAGCAUUAAUGACCAAUGAdTdT | 266 | UCAUUGGUCAUUAAUGCUUdTdT | AL-DP-2016 |
| | | 248 | CGAUAAUAUAACAGCAAGAdTsdT | 267 | UCUUGCUGUUAUAUUAUCGdTsdT | AL-DP-1729 |
| | | 249 | CGAUUAUAUUACAGGAUGAdTsdT | 268 | UCAUCCUGUAAUAUAAUCGdTsdT | AL-DP-1730 |

RSV P Gene Activity

| RSV P gene duplex ID # | % inhibition (5 nM) | % inhibition RSV A2 500 pM | % inhibition RSV A2 50 pM | % inhibition RSV A2 5 pM | % inhibition RSV B (5 nM) |
|---|---|---|---|---|---|
| AL-DP-2000 | 3 | | | | |
| AL-DP-2001 | 4 | | | | |
| AL-DP-2002 | 7 | | | | |
| AL-DP-2003 | 98 | 93 | 92 | 84 | 97 |
| AL-DP-2004 | 3 | | | | |
| AL-DP-2005 | 7 | | | | |
| AL-DP-2006 | 5 | | | | |
| AL-DP-2007 | 4 | | | | |
| AL-DP-2008 | 7 | | | | |
| AL-DP-2009 | 2 | | | | |
| AL-DP-2010 | 7 | | | | |
| AL-DP-2011 | 4 | | | | |
| AL-DP-2012 | 96 | 77 | 68 | 66 | 92 |
| AL-DP-2013 | 98 | 85 | 76 | 75 | 89 |
| AL-DP-2014 | 98 | 85 | 81 | 68 | 66 |
| AL-DP-2015 | 7 | | | | |
| AL-DP-2016 | 98 | 88 | 82 | 75 | 94 |
| AL-DP-1729 | 90 | | | | |
| AL-DP-1730 | | | | | |

TABLE 1c

RSV N Gene siRNA sequences

| Actual start | SEQ ID NO. | Sense | SEQ ID NO. | Antisense | RSV N gene DUPLEX ID # |
|---|---|---|---|---|---|
| 3 | 1 | GGCUCUUAGCAAAGUCAAGdTdT | 2 | CUUGACUUUGCUAAGAGCCdTdT | AL-DP-2017 |
| 5 | 269 | CUCUUAGCAAAGUCAAGUUdTdT | 277 | AACUUGACUUUGCUAAGAGdTdT | AL-DP-2018 |

TABLE 1c-continued

| | | | | | | |
|---|---|---|---|---|---|---|
| 52 | 270 | CUGUCAUCCAGCAAAUACAdTdT | 278 | UGUAUUUGCUGGAUGACAGdTdT | AL-DP-2019 |
| 53 | 271 | UGUCAUCCAGCAAAUACACdTdT | 279 | GUGUAUUUGCUGGAUGACAdTdT | AL-DP-2020 |
| 191 | 272 | UAAUAGGUAUGUUAUAUGCdTdT | 280 | GCAUAUAACAUACCUAUUAdTdT | AL-DP-2021 |
| 379 | 273 | AUUGAGAUAGAAUCUAGAAdTdT | 281 | UUCUAGAUUCUAUCUCAAUdTdT | AL-DP-2022 |
| 897 | 274 | AUUCUACCAUAUAUUGAACdTdT | 282 | GUUCAAUAUAUGGUAGAAUdTdT | AL-DP-2023 |
| 898 | 275 | UUCUACCAUAUAUUGAACAdTdT | 283 | UGUUCAAUAUAUGGUAGAAdTdT | AL-DP-2024 |
| 899 | 276 | UCUACCAUAUAUUGAACAAdTdT | 284 | UUGUUCAAUAUAUGGUAGAdTdT | AL-DP-2025 |

RSV N Gene Activity

| RSV N gene Duplex ID # | % inhibition (5 nM) | % inhibition RSV A2 500 pM | % inhibition RSV A2 50 pM | % inhibition RSV A2 5pM | % inhibition RSV B (5 nM) |
|---|---|---|---|---|---|
| AL-DP-2017 | 98 | 86 | 84 | 80 | 93 |
| AL-DP-2018 | 2 | | | | |
| AL-DP-2019 | 5 | | | | |
| AL-DP-2020 | 2 | | | | |
| AL-DP-2021 | 3 | | | | |
| AL-DP-2022 | 98 | 78 | 77 | 75 | 94 |
| AL-DP-2023 | 1 | | | | |
| AL-DP-2024 | 7 | | | | |
| AL-DP-2025 | 96 | 89 | 84 | 77 | 96 |

Example 2

In Vitro Assay and Virus Infection

Vero E6 cells were cultured to 80% confluency in DMEM containing 10% heat-inactivated FBS. For siRNA introduction, 4 µl of Transit-TKO was added to 50 µl of serum-free DMEM and incubated at room temperature for 10 minutes. Then, an indicated concentration of siRNA was added to media/TKO reagent respectively and incubated at room temperature for 10 minutes. This mixture was added to 200 µA of DMEM containing 10% FBS and then to a monolayer of cultured cells. The cells were incubated at 37° C., 5% $CO_2$ for 6 hours. The RNA mixture was removed by gentle washing with 1× Hank's Balanced Salt Solutions (HBSS) and 300 plaque-forming units (pfu) per well of RSV/A2 (MOI=30) was added to wells and adsorbed for 1 hour at 37° C., 5% $CO_2$. Virus was removed and the cells were washed with 1×HBSS. Cells were overlaid with 1% methylcellulose in DMEM containing 10% FBS media, and incubated for 6 days at 37° C., 5% $CO_2$. Cells were immunostained for plaques using anti-F protein monoclonal antibody 131-2A.

Example 3 siRNA Delivery and Virus Infection In Vivo

Pathogen-free 4 week old female BALB/c mice were purchased from Harlan. Mice were under anesthesia during infection and intranasal instillation (i.n.). Mice were immunized by intranasal instillation with indicated amount of siRNA, either uncomplexed, or complexed with 5 µl Transit TKO. 150 µg of Synagis (monoclonal antibody clone 143-6C, anti-RSV F protein) and Mouse Isotype control (IgG1) were administered intraperitoneal (i.p.) four hours prior to RSV challenge ($10^6$ PFU of RSV/A2). Ten mice per group were used. Animal weights were monitored at days 0, 2, 4, and 6 post-infection. Lungs were harvested at day 6 post-infection, and assayed for RSV by immunostaining plaque assay.

Example 4

Immunostaining Plaque Assay 24-well plates of Vero E6 cells were cultured to 90% confluency in DMEM containing 10% heat inactivated FBS. Mice lungs were homogenized with hand-held homogenizer in 1 ml sterile Dulbecco's PBS (D-PBS) and 10 fold diluted in serum-free DMEM. Virus containing lung lysate dilutions were plated onto 24 well plates in triplicate and adsorbed for 1 hour at 37° C., 5% $CO_2$. Wells were overlaid with 1% methylcellulose in DMEM containing 10% FBS. Then, plates were incubated for 6 days at 37° C., 5% $CO_2$. After 6 days, overlaid media was removed and cells were fixed in acetone: methanol (60:40) for 15 minutes. Cells were blocked with 5% dry Milk/PBS for 1 hour at 37° C. 1:500 dilution of anti-RSV F protein antibody (131-2A) was added to wells and incubated for 2 hours at 37° C. Cells were washed twice in PBS/0.5% Tween 20. 1:500 dilution of goat anti-mouse IgG-Alkaline Phosphatase was added to wells and incubated for 1 hour at 37° C. Cells were washed twice in PBS/0.5% Tween 20. Reaction was developed using Vector's Alkaline Phosphatase substrate kit II (Vector Black), and counterstained with Hematoxylin. Plaques were visualized and counted using an Olympus Inverted microscope.

Example 5

Treatment Assay

Mice were challenged with RSV ($10^6$ PFU of RSV/A2) by intranasal instillation at day 0 and treated with 50 μg of indicated siRNA, delivered by intranasal instillation, at the indicated times (day 1-4 post viral challenge). 3-5 mice per group were used and viral titers were measured from lung lysates at day 5 post viral challenge, as previously described.

Example 6

In Vitro Inhibition of RSV Using iRNA Agents iRNA agents provided in Table 1 (a-c) were tested for anti-RSV activity in a plaque formation assay as described above. Results are shown in FIG. 1. Each column (bar) represents an iRNA agent provided in Table 1 (a-c), e.g., column 1 is the first agent in Table 1a, second column is the second agent and so on. Active iRNA agents were identified by the % of virus remaining Several agents were identified that showed as much as 90% inhibition. The results are summarized in Table 1 (a-c).

In vitro dose response inhibition of RSV using iRNA agents was determined. Examples of active agents from Table 1 were tested for anti-RSV activity in a plaque formation assay as described above at four concentrations. A dose-dependent response was found with active iRNA agents tested as illustrated in FIG. 2) and summarized in Tables 1(a-c).

In vitro inhibition of RSV B subtype using iRNA agents was tested as described above. iRNA agents provided in FIG. 2 were tested at 5 nM for anti-RSV activity against subtype B as shown in FIG. 3. RSV subtype B was inhibited by the iRNA agents tested to varying degrees. These results also are summarized in Table 1(a-c).

Example 7

In Vivo Inhibition of RSV Using iRNA Agents

In vivo inhibition of RSV using AL1729 and AL1730 was tested as described above. Agents as described in FIG. 4 were tested for anti-RSV activity in a mouse model. The iRNA agents were effective at reducing viral titers in vivo and more effective than a control antibody (Mab 143-6c, a mouse IgG1 Ab that is approved for RSV treatment).

AL1730 was tested for dose-dependent activity using the methods provided above. The agent showed a dose-dependent response as illustrated in FIG. 5.

iRNA agents showing in vitro activity were tested for anti-RSV activity in vivo as outlined above. Several agents showed a reduction in viral titers of >4 logs when given prophylactically as illustrated in FIG. 6.

iRNA agents showing in vitro and/or in vivo activity were tested for anti-RSV activity in vivo as in the treatment protocol outlined above. Several agents showed a reduction in viral titers of 2-3 logs as shown in FIG. 7 when given 1-2 days following viral infection.

Example 8

Sequence Analysis of Isolates Across Target Sequence

Growth of Isolates and RNA Isolation:
Clinical isolates from RSV infected patients were obtained from Larry Anderson at the CDC in Atlanta Ga. (4 strains) and John DeVincenzo at the University of Tenn., Memphis (15 strains). When these were grown in HEp-2, human epithelial cells (ATCC, Cat# CCL-23) cells, it was noted that the 4 isolates from Georgia were slower growing than the strains from Tennessee; hence, these were processed and analyzed separately. The procedure is briefly described as follows:

Vero E6, monkey kidney epithelial cells (ATCC, Cat# CRL-1586) were grown to 95% confluency and infected with a 1/10 dilution of primary isolates. The virus was absorbed for 1 hour at 37° C., then cells were supplemented with D-MEM and incubated at 37° C. On a daily basis, cells were monitored for cytopathic effect (CPE) by light microscopy. At 90% CPE, the cells were harvested by scraping and pelleted by centrifugation at 3000 rpm for 10 minutes. RNA preparations were performed by standard procedures according to manufacturer's protocol.

Amplification of RSV N Gene:
Amplification of the RSV N gene fragment containing the ALN-RSV01 recognition site was performed using two step RT-PCR.

First, RNA was reverse transcribed using random hexamers and Superscript III Reverse transcriptase (Invitrogen, Carlsbad, Calif.) at 42° C. for 1 hour, to generate a cDNA library. Next a 1200 nt gene specific fragment was amplified using the forward primer RSV NF: 5'-AGAAAACTTGAT-GAAAGACA-3' (SEQ ID NO: 285); and the reverse primer RSV NR: 5'-ACCATAGGCATTCATAAA-3' (SEQ ID NO: 286) for 35 cycles at 55° C. for 30 sec followed by 68° C. for 1 min, using Platinum Taq polymerase (Invitrogen, Carlsbad, Calif.). PCR products were analyzed by 1% agarose gel electrophoresis.

Results:
Sequence analysis of the first 15 isolates confirmed that the target site for ALN-RSV01 was completely conserved across every strain. Sequence alignments are provided in FIG. 8. Importantly, this conservation was maintained across the diverse populations, which included isolates from both RSV A and B subtypes. Interestingly, when the 4 slower-growing isolates were analyzed, we observed that one of the 4 (LAP6824) had a single base mutation in the ALN-RSV01 recognition site as shown in the top part of FIG. 9. This mutation changed the coding sequence at position 13 of the RSV N gene in this isolate from an A to a G (FIG. 9, bottom).

Conclusions:
From 19 patient isolates, the sequence of the RSV N gene at the target site for ALN-RSV01 has been determined. In 18 of 19 cases (95%), the recognition element for ALN-RSV01 was determined to be 100% conserved. In one of the isolates, there was detected a single base alteration changing the nucleotide at position 13 from an A to a G within the RSV N gene. This alteration creates a single G:U wobble between the antisense strand of ALN-RSV01 and the target sequence as shown in FIG. 9, bottom. Based on an understanding of the hybridization potential of such a G:U wobble, ALN-RSV01 is predicted to be effective in silencing the RSV N gene in this isolate.

Example 9

Synthesis and Purification of ALN-RSV01

As shown in FIG. 10, the process for manufacturing the ALN-RSV01 drug substance consists of synthesizing the two single strand oligonucleotides (sense and antisense) by conventional solid phase synthesis using 3'-O-(2-cyanoethyl) phosphoramidite chemistry with the 5'-hydroxyls protected with 4,4'-dimethoxytriphenylmethyl (dimethoxytrityl, DMT)

groups and tert-butyldimethylsilyl (TBDMS) protection on the 2'-hydroxyls of the ribose nucleosides. The crude single strand oligonucleotides were cleaved from the solid support, de-protected in a two-step process and purified by preparative anion exchange high performance liquid chromatography (AX-HPLC). The two single strands were combined in an equimolar ratio followed by annealing and lyophilization to produce the ALN-RSV01 drug substance.

Solid Phase Synthesis:

Assembly of an oligonucleotide chain by the phosphoramidite method on a solid support, such as controlled pore glass (CPG) or polystyrene followed the iterative process outlined in FIG. 11. The synthesis of ALN-RSV01 sense and antisense single strand intermediates was carried out on support loaded with 5'-dimethoxytrityl thymidine. Each intermediate was assembled from the 3' to the 5' terminus by the addition of protected nucleoside phosphoramidites and an activator. All the reactions took place on the derivatized support in a packed column. Each elongation cycle consisted of four distinct steps.

5'-Hydroxyl Deprotection (Detritylation, FIG. 11 step A):

In the beginning of the synthesis the DMT-thymidine support was subjected to removal of the acid labile 4,4'-dimethoxytrityl protecting group from the 5'-hydroxyl. Each cycle of the synthesis thereafter commenced with removal of the corresponding DMT protecting group from the 5' oxygen atom of the support-bound oligonucleotide (FIG. 11 step A). This was accomplished by treatment with a solution of dichloroacetic acid in toluene. Following detritylation the support-bound material was washed with acetonitrile in preparation for the next reaction.

Coupling (FIG. 11 step B):

The elongation of the growing oligonucleotide chain was achieved by reaction of the 5'-hydroxyl group of the support-bound oligonucleotide with an excess of a solution of the protected nucleoside phosphoramidite, in the presence of the activator 5-ethylthio-1H-tetrazole. The amidite required in each step was determined by the oligonucleotide sequence described in Table 1c. This resulted in the formation of a phosphite triester internucleotide linkage. After allowing sufficient time for the coupling reaction to complete, excess phosphoramidite and activator was rinsed from the reactor using acetonitrile.

Oxidation (FIG. 11 step C):

The newly created phosphite triester linkage was then oxidized by treatment with a solution of iodine in pyridine in the presence of water. This resulted in the formation of the corresponding phosphotriester bond (FIG. 11 step C). After the oxidation was complete, the excess reagent (iodine in pyridine/water) was removed from the column by rinsing the support with acetonitrile.

Capping (FIG. 11 step D):

Although the coupling reaction proceeds in very high yield it is not quite quantitative. A small proportion (typically less than 1%) of the 5'-hydroxy groups, available in any given cycle, fails to couple with the activated phosphoramidite. In order to prevent reaction during subsequent cycles these sites were blocked by using capping reagents (acetic anhydride and N methylimidazole/2,6 lutidine/acetonitrile). As a result 5'-O-acetylated ('capped') support-bound oligonucleotide sequences were formed.

Cleavage and De-protection:

Reiteration of this basic four-step cycle using the appropriate protected nucleoside phosphoramidites allowed assembly of the entire protected sequence. The DMT group protecting the hydroxyl at the 5'-terminus of the oligonucleotide chain was removed. The crude oligonucleotide was cleaved from the solid support by aqueous methylamine treatment with concomitant removal of the cyanoethyl phosphate protecting group. The support was removed by filtration and washed with dimethyl sulfoxide. The cleavage solution and wash were combined and held at room temperature or elevated temperatures to complete the deprotection of the exocyclic amino groups (benzoyl, isobutyryl, and acetyl) as shown in FIG. 12 step A. The 2'-O-TBDMS protecting groups were then cleaved using a solution of pyridine-hydrogen fluoride to yield the crude oligonucleotide (FIG. 12 step B). At the completion of the deprotection the solution was diluted with aqueous buffer and subjected to the purification step.

AX-HPLC Purification:

Purification of each crude product solution was accomplished by AX-HPLC. A solution of crude product was loaded onto the purification column packed with Source 15Q media. The purification run was performed using sodium phosphate buffered eluents containing approximately 10% acetonitrile. A sodium chloride gradient was used to elute the oligonucleotide from the column. The purification was carried out at elevated temperatures (65-75° C.). The elution profile was monitored by UV absorption spectroscopy. Fractions were collected and pooled. Pools containing product at target purity levels were subjected to the next step in the process. Fractions that did not meet the acceptance criteria were, in some instances, repurified.

Desalting:

The oligonucleotide solutions were concentrated using tangential flow filtration (TFF) using a polyethersulfone (PES) membrane cassette with a nominal 1,000 molecular weight cut-off. The retentate from the concentration step was pH adjusted and diafiltered with water to remove salts and solvents used in the AX-HPLC purification. The desalted product solution (retentate) was sometimes further concentrated by TFF before transfer to the next step.

Duplex Formation:

The ultrafiltered solutions of the sense and antisense strand were combined in the desired proportions to form an equimolar mixture of the two intermediates. The required amounts of each single strand oligonucleotide were calculated based on UV assay and their molecular weights. To assure better control, the calculated amount of the first strand was mixed with less than the calculated amount of the second strand. AX-HPLC analysis of a sample of that mixture showed a well-resolved peak for the excess of the first strand together with a peak for the duplex. An additional amount of the second strand was added and a sample was analyzed again. This process was repeated until excess of one of the strands is was determined to be ≤1 area % as judged by the HPLC chromatogram. The solution was then heated and cooled under controlled conditions to anneal the duplex.

Freeze Drying:

The duplex solution was filtered through a 0.2-micron filter before loading into disposable single use trays for bulk drying. The filtered product solution was freeze dried using a cycle consisting of three steps: (1) a freeze step, (2) primary drying at 0° C., and (3) secondary drying at 25° C. The result of this process is a lyophilized powder, i.e., a powder produced by the process that includes the steps of freezing a liquid and, drying the frozen liquid product under vacuum to remove by sublimation some or all of the frozen water.

Container Closure System:

The lyophilized ALN-RSV01 drug substance was packaged in clean high-density polyethylene bottles with screw closures, labeled and stored in a freezer at −10 to −25° C. until shipment. In some instances, a moisture barrier bag was added to the packaging of the inventory. The selected bag (Model LF4835W from Laminated Films & Packaging) has three layers (white PET, foil, and polyethylene) and is specifically recommended as a barrier for oxygen and moisture.

Drug Finishing:

ALN-RSV01 drug substance was delivered to a sterile fill/finish site as a lyophilized powder in sealed containers. Each container held a known weight of ALN-RSV01 drug substance. The bulk weight, the duplex purity, and the water content value were used to calculate the ALN-RSV01 drug substance available for formulation. As the drug substance is hygroscopic, whole containers were allocated for the manufacturing process. The size of the containers used allowed drug allocation to be close to the target lot size. The phosphate buffer solution was prepared to the required composition in a quantity in excess of that required to prepare the target lot size. The pH of the buffer was adjusted to 7.4±0.7. Allocated ALN-RSV01 drug substance, in whole vials, was dissolved into 80% of the target batch volume of phosphate buffer solution. An in-process sample was taken and the potency measured by UV/SEC. Using this assay value the theoretical batch size was calculated to give 100% potency. Using the remaining prepared buffer the lot was brought to this theoretical volume. The pH was monitored and adjusted as needed to 6.6+1.0. The lot was then aseptically filtered through two 0.22 μm sterile filters in series, filled into individual, sterile vials, stoppered, sealed, inspected (100% visual), and labeled. All vials were stored at 2-8° C.

Formulation Development:

ALN-RSV01 drug product was formulated to a pH of 6.6 with sodium phosphate buffer. Phosphoric acid and sodium hydroxide were available for pH adjustment as needed. The formulation was near isotonicity, therefore there was no need to use sodium chloride to adjust osmolality. Osmolality of the ALN-RSV01 drug product used for intranasal administration or inhalation preferably ranges between 200-400 mOsm/kg.

Each vial of ALN-RSV01 drug product contains a volume of 0.5 mL. The product was filled into clear Type I glass vials sealed with Teflon-coated butyl rubber stoppers with aluminum flip-off overseals. All vials were maintained at 2-8° C. and were warmed to room temperature prior to use. In some instances, dilutions of drug product were prepared in normal saline by pharmacy staff.

Description and Composition of the Drug Product:

ALN-RSV01 drug product was formulated as an aqueous solution in 50 mM phosphate buffer, pH 6.6 at a nominal concentration of 150 mg/mL. The quantitative composition of the ALN-RSV01 drug product is shown in Table 3. The weight shown for formulation reflects pure, anhydrous oligonucleotide. The amount of active ingredient per batch was calculated to account for the "as is" purity as determined by UV, ALN-RSV01 area value by SEC and the moisture content.

TABLE 3

Quantitative Composition Of The ALN-RSV01 Drug Product

| Ingredient | Quantity per mL | Function |
|---|---|---|
| ALN-RSV01 | 150 mg | Active Ingredient |
| Dibasic Sodium Phosphate Heptahydrate | 11.42 mg | Buffer |
| Monobasic Sodium Phosphate Monohydrate | 1.01 mg | Buffer |
| Phosphoric Acid | q.s. | pH Adjustment |
| Sodium Hydroxide | q.s | pH Adjustment |
| Water for Injection | q.s. to 1 mL | Vehicle |

Stability Studies:

ALN-RSV01 (Lot# R01) was evaluated after initial, one, two, three, six and nine months of storage and found to be chemically stable using stability indicating methods such as denaturing AX-HPLC and SEC. Follow on studies confirmed stability of an aqueous buffered solution of the drug substance when stored at 2° C.-8° C. The lyophilized drug substance stored at −20° C. is expected to be at least as stable as the aqueous buffered solution. As used herein, "stable" means resistant to chemical changes that preclude product use in human subjects. Stability can be assessed by measuring stability and purity using methods that include denaturing AX-HPLC and SEC to provide measures of the overall proportion of the drug product comprised of the sense and antisense strands, as well as the fraction of the drug product that is found in duplex form. Other measures of stability include one or more of: tests for pyrogens, analysis of water content, tests of the Tm, i.e., the parameter that addresses the quality of the duplex, and assay values for inhibition of RSV gene expression, drop in viral titre, etc. using, e.g., tests exemplified in the working examples.

Compatibility with BD AccuSpray™ Nasal Spray System:

A phase 2a clinical study was conducted by nasal instillation using the commercially available Becton-Dickinson Accuspray™ nasal spray system. Compatibility of ALN-RSV01 drug product was confirmed by evaluating the stability of ALN-RSV01 drug product in contact with the system over a fourteen-day period, both in ambient and refrigerated (2-8° C.) conditions. No degradation was observed upon storage of up to 14 days at 10 and 150 mg/mL, in ambient and refrigerated conditions as measured by appearance, SEC, stability indicating denaturing AX-HPLC, pH, osmolality and UV assay.

Example 9

Silencing Data on Isolates

Methods:

Vero E6 cells were cultured to 80% confluency in DMEM containing 10% heat-inactivated FBS. For siRNA introduction, 4 μl of Transit-TKO was added to 50 μl of serum-free DMEM and incubated at room temperature for 10 minutes. Then, indicated concentration of siRNA was added to media/TKO reagent respectively and incubated at room temperature for 10 minutes. RNA mixture was added to 200 μl of DMEM containing 10% FBS and then to cell monolayer. Cells were incubated at 37° C., 5% $CO_2$ for 6 hours. RNA mixture was removed by gentle washing with 1× Hank's Balanced Salt Solutions (HBSS) and 300 plaque-forming units (pfu) per well of RSV/A2 (MOI=30) was added to wells and adsorbed for 1 hour at 37° C., 5% $CO_2$. Virus was removed and cells were washed with 1×HBSS. Cells were overlaid with 1% methylcellulose in DMEM containing 10% FBS media, and incubated for 6 days at 37° C., 5% $CO_2$. Cells were immunostained for plaques using anti-F protein monoclonal antibody 131-2A.

Results:

Silencing by ALN-RSV01 was seen for all isolates as shown in Table 4.

TABLE 4

Silencing Of Isolates By ALN-RSV01

| Isolate name | ALN-RSV01 % plaques remaining | 2153 % plaques remaining |
|---|---|---|
| RSV/A2 | 4.49 | 80.34 |
| RSV/96 | 5.36 | 87.50 |
| RSV/87 | 10.20 | 79.59 |
| RSV/110 | 5.41 | 81.08 |
| RSV/37 | 4.80 | 89.60 |
| RSV/67 | 2.22 | 91.67 |
| RSV/121 | 6.25 | 82.50 |
| RSV/31 | 4.03 | 96.77 |
| RSV/38 | 2.00 | 92.67 |
| RSV/98 | 5.13 | 91.03 |
| RSV/124 | 3.74 | 90.37 |
| RSV/95 | 7.32 | 64.02 |
| RSV/32 | 5.45 | 92.73 |
| RSV/91 | 8.42 | 95.79 |
| RSV/110 | 12.07 | 94.83 |
| RSV/54 | 1.90 | 89.87 |
| RSV/53 | 7.41 | 94.07 |
| RSV/33 | 7.69 | 95.19 |

Conclusion:
All clinical isolates tested were specifically inhibited by ALN-RSV01 by greater than 85%. No isolates were significantly inhibited by the mismatch control siRNA 2153.

Example 10

Silencing in Plasmid Based Assay

Methods:
A 24-well plate was seeded with HeLa S6 cells and grown to 80% confluence. For each well, 1 μg of RSV N-V5 plasmid was mixed with a siRNA (at indicated concentration), in 50 ul OPTI-MEM which then was added to a Lipofectamine 2000 (Invitrogen)-Optimem mixture prepared according to manufacturer's instructions. This mixture was incubated for 20 minutes at room temperature to allow time for complex formation between the siRNA and the Lipofectamine-Optimem components. The complexed mixture was added complex to cells and incubated at 37° C. overnight. The media was removed, cells were washed with phosphate-buffered saline (PBS) and then lysed by the incubation with 50 ul Lysis buffer (RIPA buffer (50 mM Tris-HCl pH 8.0, 150 mM NaCl, 1 mM EDTA, 0.5% Na deoxycholate, 1% NP-40, 0.05% SDS) for 1-2 min. Lysates were analyzed and inhibition of RSV-N protein expression was quantified by measuring the level of RSV-N protein in cell lysates, as detected by Western blotting with an anti-V5 antibody.

Results:
Transient plasmid expression was shown to be an effective assay for RNAi agents (Table 5).

TABLE 5

Silencing as measured in a plasmid based assay

| | siRNA | Concentration | Protein % | Activity % |
|---|---|---|---|---|
| 1 | ALN-RSV01 | 10 nM | 0 | 100 |
| 2 | ALN-RSV01 | 1 nM | 0 | 100 |
| 3 | ALN-RSV01 | 100 pM | 0 | 100 |
| 4 | ALN-RSV01 | 10 pM | 11.78 | 88.22 |
| 5 | ALN-RSV01 | 1 pM | 70.63 | 29.37 |
| 6 | ALN-RSV01 | 100 fM | 72.7 | 27.3 |
| 7 | Control | PBS | 100 | 0 |
| 8 | 2153 | 10 nM | 94.54 | 4.5 |

Conclusions:
siRNA 2017 (ALN-RSV01) was shown to specifically and dose-dependently inhibit the production of RSV N protein when transiently cotranfected with a plasmid expressing the RSV N gene. Inhibition is not observed using mismatch control siRNA 2153.

Example 11

Silencing of RSV Via Aerosol Delivery of siRNA

Method:
A 2 mg/ml solution of AL-DP-1729 or AL-DP-1730 was delivered via nebulization using an aerosol device for a total of 60 sec. Viral samples were prepared from lung as described above and measured using an ELISA instead of a plaque assay. The ELISA measures the concentration of the RSV N protein in virus-infected cells obtained from mouse lung lysates.

Methods:
Lung lysate was diluted 1:1 with carbonate-bicarbonate buffer ($NaHCO_3$ pH 9.6) to a working concentration of 6-10 μg/1004, added to each test well and incubated at 37° C. for 1 hour or overnight at 4° C. Wells were washed 3× with PBS/0.5% Tween 20 then blocked with 5% dry milk/PBS for 1 hour at 37° C. or overnight at 4° C. Primary antibody (F protein positive control=clone 131-2A; G protein positive control=130-2G; negative control=normal IgG11c, (BD Pharmingen, cat. #553454, test sera, or hybridoma supernatant) was added to the wells at a final dilution of 1:1000, and incubated at 37° C. for 1 hour or overnight at 4° C. Wells were washed 3× with PBS/0.5% Tween 20. Secondary antibody (Goat Anti-mouse IgG (H+L) whole molecule-alkaline phosphatase conjugated) was added to the wells at a final dilution of 1:1000 (100 μl/well) and incubated at 37° C. for 1 hour or overnight at 4° C. The wells were washed 3× with PBS/0.5% Tween 20, after which time 200 μl of Npp (Sigmafast) substrate (Sigma Aldrich N2770) made according to manufacturer's instructions was added to the wells. This mixture was incubated for 10-15 at 37° C., and absorbances at OD 405/495 were measured.

Conclusion:
Delivery of RSV specific siRNA decreases the levels of RSV N protein in mouse lungs as compared to the mismatch control siRNA (FIG. 13a-b).

Example 12

In Vivo Inhibition at Day −3-Prophylaxis

Method:
In vivo prophylaxis was tested using the in vivo method described above except that the siRNA is delivered at different times prior to infection with RSV from 3 days before to 4 hrs before. Results were obtained for AL-DP-1729 (active) and AL-DP-1730 (mismatch control).

Results:
Active siRNA delivered intranasally up to 3 days prior to viral challenge show specific and significant silencing in vivo as shown in FIG. 14.

Example 13

Nebulization of ALN-RSV01 with Pad eFlow® Device

Droplet Size and Analytical Integrity
Methods: A 150 mg/ml solution of ALN-RSV01 (in 2 mls of PBS) was filled into the Pari eFlow® electronic device and run until nebulization was completed and all aerosol was collected and allowed to condense in a polypropylene tube. Aliquots of material post nebulization were analyzed to determine geometric droplet size distribution by laser diffraction (Malvern MasterSizerX) under standard conditions. Aliquots of material pre and post nebulization were analyzed to determine analytical integrity by a stability using anion exchange HPLC methodology.

Results:

Aerosolized ALN-RSV01 had a Mass Median Diameter (MMD) of 3.1 µm, a Geometric Standard Deviation (GSD) of 1.6 and a total respirable fraction of 85% (i.e., % particles<5 µm) confirming that a 75 mg/ml solution could be aerosolized to yield respirable material with appropriate particle size. Comparison to control samples of ALN-RSV01 formulation which were not nebulized showed matching chromatograms, demonstrating that the oligonucleotide can be nebulized by eFlow® without degradation.

Biological Activity:

A 25 mg/ml solution of ALN-RSV01 (in 1 ml of PBS) was prepared, 100 µl was removed (pre-nebulization aliquot) prior to nebulization with the Pari eFlow® electronic device, and 500 ul of the nebulized solution was collected after condensing by passage over an ice bath into a chilled 50 ml conical tube (post-nebulization aliquot). Serial dilutions of both aliquots were tested in our in vitro transfection/infection plaque assay as previously described with the exception that siRNA was complexed with lipofetamine-2000.

Results:

siRNA pre and post nebulization efficiently inhibited RSV viral replication in a Vero cell plaque assay. The degree of inhibition was almost identical between the two samples and showed a dose response leading to >80% silencing at the highest siRNA concentrations confirming that nebulized ALN-RSV01 maintains biological activity. Results are shown in FIG. 15.

Example 14

Inhalable siRNAs: ALN-RSV01

To investigate the in vivo effects of aerosolization and delivery by inhalation of siRNAs targeting RSV as well as the pharmacokinetic properties of inhaled siRNAs, a double-blind, randomized, placebo-controlled, evaluation study in human adult subjects was performed. The study measured routine bloods and clinical observations, inflammatory biomarkers, tolerability and plasma pharmacokinetics. As used in this specification "inhalation" refers to administration of a dosage form that is formulated and delivered for topical treatment of the pulmonary epithelium. As described above, an inhalable dosage form comprise particles of respirable size, i.e., particles that are sufficiently small to pass through the mouth or nose and larynx upon inhalation and into the bronchi and alveoli of the lungs.

In the study, ascending doses of aerosolized ALN-RSV01 or placebo were administered once daily by inhalation for 3 consecutive days to 4 cohorts of 12 subjects each with 8 subjects receiving ALN-RSV01 and 4 subjects receiving placebo in each cohort for a total of 48 subjects. ALN-RSV01 maximum solubility concentration in the finished product is 150 mg/mL. Therefore, a 150 mg/ml solution of ALN-RSV01 was diluted to the appropriate concentration and filled into the Pari eFlow® electronic device and run until nebulization was completed.

Blood samples evaluated for pharmacokinetics (PK) included pre dose and post dose at 2, 5, 15, and 30 minutes, 1 hour and 24 hours on Day 0 and post third dose at 2, 5, 15, and 30 minutes, 1 hour and 24 hours after the third dose (13 samples per subject). Urine collection for PK included: pre dose and post third dose at 0-6 hours, 6-12 hours and 12-24 hours.

Plasma ALN-RSV01 concentrations, and derived parameters ($C_{pre}$, $C_{max}$, $t_{max}$, $t_{1/2}$, CL/F, $V_d$/F, $AUC_{last}$) were evaluated for PK.

ALN-RSV01 has previously been evaluated for toxicity by inhalation administration in rats and monkeys at doses as high as 36 mg/kg/day and 30 mg/kg/day, respectively. The highest dose to be administered in the single dose part of the current study was 210 mg/day (or 3 mg/kg, assuming 70 kg body weight). On a mg/kg basis, this dose is approximately 10 fold lower than the doses given previously to rats and monkeys.

The initial doses in this study were 7.0 mg, 21.0 mg and 70.0 mg providing a safety margin of about 300 fold, 100-fold and 30 fold, respectively.

Dose levels for the multiple dose part of the study were 7.0 mg, 21.0 mg, 70.0 mg and 210 mg, given as a daily delivered dose (DD) for three consecutive days.

The highest dose to be administered in the single dose part of the current study was chosen at 210 mg/day (or 3 mg/kg, assuming 70 kg body weight).

Study drug exposure duration in the multiple dose part of the study was chosen to be 3 days, with once daily dosing, based on the intended therapeutic dosing duration which is likely to be short due to the acute nature of RSV infections.

Pulmonary Function Tests

PFT were conducted at screening to identify healthy volunteers with respect to capacities and flow-rates. PFT provides an objective method for assessing the mechanical and functional properties of the lungs and chest wall. PFT measures:

Lung capacities e.g., Slow Vital Capacity (SVC) and Force Vital Capacity (FVC), which provide a measurement of the size of the various compartments within the lung Volume parameters (e.g., FEV1) and flow-rates (e.g., FEF25-75), which measure maximal flow within the airways Serial evaluations of pulmonary function after inhalation of ALN-RSV01 or placebo were conducted. Additional PFT testing was conducted on Day 0 at pre-dose (about −30 min) and at 30 min and 2 h, 6 h, and 12 h on Days 1, 1 and 2 at the same time as pre-dose on Day 0.

PFT provides lung capacities and flow-rates. The SVC is the volume of gas slowly inhaled when going from complete expiration to complete inhalation. The FVC is the volume expired when going from complete inhalation to complete exhalation as hard and fast as possible. The FEV1 is the amount expired during the first second of the FVC maneuver. The Forced Expiratory Flow (FEF25-75) is the average expiratory flow over the middle half of the FVC. SVC, FVC, FEV1 and FEF25-75 was measured according the ATS/ERS guidelines. In this study, FEV1 was the main parameter.

As shown in FIG. 16, no significant change in lung function was seen on aerosol administration of ALN-RSV01.

Plasma

For single dosing, blood samples were collected for the analysis of ALN-RSV01 in plasma at pre dose and post dose (post nebulization) at 2, 5, 15, and 30 minutes, 1 hour and 24 hours on Day 0 (7 samples per volunteer).

For multi-dosing, blood samples were collected for analysis of ALN-RSV01 in plasma at pre-dose and at 2, 5, 15 and 30 min, 1 h, and 24 h post first-dose on Day 0 (post nebulization), and at 2, 5, 15, 30 min, 1 h, and 24 h after the third dose (post dose nebulization of third dose).

Blood samples of 5 mL each were taken via an indwelling intravenous catheter or by direct venipuncture into tubes containing K3EDTA as the anticoagulant. In case of sampling through the intravenous catheter, the first 1 mL of blood was discarded in order to prevent any dilution of blood with heparin used to flush the catheter.

Results

A safe and well tolerated regimen of ALN-RSV01 has been defined for further clinical development. To this end the data show that plasma exposure for a given dose in man is greater than in nonhuman primates. See FIG. 17. While single dose administration at 3 mg/kg equivalent was associated with a greater incidence of a flu-like adverse event (cough, headache, non-cardiac chest pain, pharyngo-laryngeal pain and chills) relative to placebo multi-dose administration of AL-DP 2017 was safe and well-tolerated when given once daily for 3 days up to 0.6 mg/kg per dose. There was also no evidence of neutrophil leucocytosis after multi dosing of AL-DP-2107 in the highest dose cohort (0.6 mg/kg). See FIG. 18.

Example 15

A Split Dose of ALN-RSV01 Reduced RSV Titer Levels In Vivo

A fixed dose (120 μg) of ALN-RSV01 was administered to rodents intranasally 4 hours prior to RSV instillation ($10^6$ pfu at timepoint zero). Mice were then administered 120 μg of ALN-RSV01 intranasally on the first, second or third day following instillation, or in three administrations split equally over days 1, 2, and 3 following instillation. The dose administered over the course of three days maintained the same reduced RSV titer levels in the lung as observed by the single dose of the siRNA on the first day following infection. See FIG. 19.

Example 16

RNAi-Specific Activity of RSV-Targeted siRNAs

Materials And Methods

Animals. Six- to eight-week old, pathogen-free female BALB/c mice were purchased from Harlan Sprague-Dawley Laboratories (Indianapolis, Ind.). The mice were housed in microisolator cages and fed sterilized water and food ad libitum.

Virus Preparation, Cell Lines and Viral Titering.

Vero E6 cells were maintained in tissue culture medium (TCM) consisting of Dulbecco's Modified Eagle Medium (D-MEM, GIBCO Invitrogen, Carlsbad, Calif.) supplemented with 10% fetal bovine serum (Hyclone, Logan, Utah). RSV/A2 and RSV/B1 were prepared in Vero E6 cells. Briefly, confluent Vero E6 cells (American Type Culture Collection, Manassas, Va.) in serum-free D-MEM, were infected with RSV at a multiplicity of infection (MOI) of 0.1. The virus was adsorbed for 1 h at 37° C. after which TCM was added. Infected cells were incubated for 72-96 h at 37° C. until >90% cytopathic effect (CPE) was observed by light microscopy. Infected cells were harvested by removal of the medium and replacement with a minimal volume of serum-free D-MEM followed by three freeze-thaw cycles at −70 and 4° C., respectively. The contents were collected and centrifuged at 4000×g for 20 min at 4° C. to remove cell debris, and the titer was determined by immunostaining plaque assay as previously described. Briefly, Vero E6 cells are infected with serial dilutions of stock RSV, adsorbed for 1 h at 37° C., then overlayed with 2% methylcellulose media (DMEM, supplemented with 2% fetal bovine serum, 1% antibiotic/antimycotic solution, 2% methylcellulose). After 5 days at 37° C./5% $CO_2$, plates are removed and cells are fixed with ice-cold Acetone:Methanol (60:40). Cells are blocked with Powerblock, universal blocking reagent (Biogenix, San Ramon, Calif.), incubated with Anti-RSV F protein monoclonal antibody 131-2A dilute 1:200 (Millipore-Chemicon), followed by Goat anti-mouse IgG whole molecule alkaline phosphatase secondary antibody. The reaction was developed with Alkaline phosphatase substrate kit (Vector Black, Vector Laboratories, Burlingame, Calif.) and plaques were visualized and counted using a light microscope. For RSV primary isolate cultures, samples were obtained from Dr. John DeVincenzo from the University of Tennessee, Memphis, Tenn. RSV isolates were obtained from RSV infected children diagnosed by either a conventional direct fluorescent antibody (DFA) method or by a rapid antigen detection method in the Le Bonheur Children's Medical Center Virology Laboratory in Memphis, Tenn. Nasal secretions were collected by aspiration, grown and passaged in HEp-2 cells and harvested at 90% cytopathic effect. Individual aliquots of supernatant containing RSV were then subjected to nucleic acid extraction using QiAmp Viral RNA mini kit, according to the manufacturer's protocol (Qiagen, Valencia, Calif.). RSV isolates were also obtained from Mark Van Ranst from the University of Leuven, Leuven, Belgium and Larry Anderson from the Centers for Disease Control and Prevention, Atlanta, Ga.

RSV-Specific siRNA Selection.

Using one of the National Center for Biotechnology Information (NCBI) databases a Basic Local Alignment Search Tool (BLAST), was performed. In this analysis, a sequence comparison algorithm is used to search sequence databases for optimal local alignments to a query (2). In this case, the query is the 19 nt sequence comprising the sense or antisense strand of ALN-RSV01, excluding the dTdT overhang. The database, Reference Sequence (RefSeq), provides a comprehensive, integrated, non-redundant set of sequences, including genomic DNA, transcript (RNA), and protein products, and is updated weekly (49). Only siRNAs that showed no significant homology to any sequence from the RefSeq database were selected for synthesis and further study.

In Vitro RSV Inhibition Assay.

Vero cells, in 24-well plates, were grown in a 5% $CO_2$ humidified incubator at 37° C. in DMEM supplemented with 10% fetal bovine serum (Life Technologies-Invitrogen, Carlsbad, Calif.), 100 units/ml penicillin, and 100 g/ml streptomycin (BioChrom, Cambridge, UK) to 80% confluence. siRNAs were diluted to the indicated concentrations in 50 μl Opti-MEM Reduced Serum Medium (Invitrogen). Separately, 3 μl Lipofectamine 2000 (Invitrogen) was diluted in 50 μl Opti-MEM mixed and incubated for 5 minutes at room temperature. siRNA and lipofectamine mixtures were combined, incubated for 20-25 minutes at room temperature, then added to cells and incubated at 37° C. overnight. The mixture was then removed from cells and 200-400 plaque forming units of RSV/A2 was incubated with cells for 1 hour at 37° C. The infected cells were covered with methylcellulose media and incubated for 5 days at 37° C. and plaques visualized by immunostaining plaque assay as described.

In Vivo Screening of RSV-Specific siRNAs.

For the prophylaxis model, BALB/c mice were anesthetized by intraperitoneal (i.p.) administration of 2,2,2-tribromoethanol (Avertin) and instilled intranasally (i.n.) with siRNA in a total volume of 50 μl of PBS. At 4 hours post siRNA instillation, the mice were anesthetized and infected i.n. with $1 \times 10^6$ PFU of RSV/A2 in 50 μl. Prior to removal of lungs at day 4 post-infection, anesthetized mice were exsanguinated by severing the right caudal artery. Lung tissue was collected in 1 ml ice cold phosphate-buffered saline (PBS; GIBCO Invitrogen). RSV titers from lungs were measured by immunostaining plaque assay. Lungs were homogenized with a hand-held Tissumiser homogenizer (Fisher Scientific, Pittsburgh, Pa.) and lung homogenates were placed on ice for 5-10 minutes to allow debris to settle. Clarified lung lysates were serially diluted 10-fold in serum-free D-MEM, added to 95% confluent Vero E6 cells cultured in D-MEM in 24-well plates (BD Falcon, San Jose, Calif.), and plaque assays were performed as described above. For the treatment model, BALB/c mice were anesthetized as above and instilled i.n. with $1 \times 10^6$ PFU of RSV/A2 in 50 µl. At one, two, three or four days post viral infection, mice were reanesthetized and instilled i.n. with siRNA in 50 µl and then viral concentrations were measured in the lungs on day 5 post infection, as described above.

siRNA Generation.

RNA oligonucleotides were synthesized using commercially available 5'-O-(4,4'-dimethoxytrityl)'3'O-(2-cyanoethyl-N,N-diisopropyl) phosphoramidite monomers of uridine (U), 4-N-benzyoylcytidine ($C^{Bz}$), 6-N-benzoyladenosine ($A^{bz}$) and 2-N-isobutyrlguanosine)($G^{iBu}$) with 2'-O-t-butyldimethylsilyl protected phosphoramidites according to standard solid phase oligonucleotide synthesis protocols (13). After cleavage and de-protection, RNA oligonucleotides were purified by anion-exchange high-performance liquid chromatography and characterized by ES mass spectrometry. To generate siRNAs from RNA single strands, equimolar amounts of complementary sense and antisense strands were mixed and annealed, and siRNAs were further characterized by CGE.

PBMC Assay.

To examine the ability of siRNAs to stimulate interferon alpha (IFNα) or tumor necrosis factor alpha (TNFα), human peripheral blood mononuclear cells (hPBMCs) were isolated from concentrated fractions of leukocytes (buffy coats) obtained from the Blood Bank Suhl, Institute for Transfusion Medicine, Germany. Buffy coats were diluted 1:1 in PBS, added to a tube of Histopaque (Sigma, St. Louis, Mo.) and centrifuged for 20 minutes at 2200 rpm to allow fractionation. White blood cells were collected, washed in PBS, followed by centrifugation. Cells were resuspended in RPMI 1640 culture medium (Invitrogen) supplemented with 10% fetal calf serum, IL-3 (10 ng/ml) (Sigma) and phytohemagglutinin-P (PHA-P) (5 µg/ml) (Sigma) for IFNα assay, or with no additive for TNFα assay at a concentration of $1 \times 10^6$ cells/ml, seeded onto 96-well plates and incubated at 37° C., 5% $CO_2$. Control oligonucleotides siRNA AL-DP-5048 duplex: 5'-GUCAUCACACUGAAUACCAAU-3' (SEQ ID NO: 287) and 3'-CACAGUAGUGUGACUUAUGGUUA-5' (SEQ ID NO: 288); siRNA AL-DP-7296 duplex: 5'-CUACACAAAU-CAGCGAUUUCCAUGU-3' (SEQ ID NO: 289) and 3'-GAUGUGUUUAGUCGCUAAAGGUACA-5' (SEQ ID NO: 290); siRNA AL-DP-1730 duplex: 5'-CGAUUAUA-UUACAGGAUGAdTsdT-3' (SEQ ID NO: 249) and 3'-dTs-dTGCUAAUAUAAUGUCCUACU-5' (SEQ ID NO: 268); and siRNA AL-DP-2153 duplex: 5'-GGCUCUAAGC-UAACUGAAGdTdT-3' (SEQ ID NO: 291) and 3'-dTdTC-CGAGAUUCGAUUGACUUC-5' (SEQ ID NO: 292) Cells in culture were combined with either 500 nM oligonucleotide, pre-diluted in OptiMEM (Invitrogen), or 133 nM oligonucleotide pre-diluted in OptiMEM and Geneporter, GP2 transfection reagent (Genlantis, San Diego, Calif.) for IFNα assay or N-[1-(2,3-Dioleoyloxy)propyl]-N,N,N-trimethylammonium methylsulfate (DOTAP) (Roche, Switzerland) for TNFα assay and incubated at 37° C. for 24 hrs. IFNα and TNFα were measured using the Bender MedSystems (Vienna, Austria) instant ELISA kit according to manufacturer's instruction.

In Vitro and In Vivo RACE.

Total RNA was purified from either in vitro transfected Vero E6 cells or from lungs harvested at day 5 post-infection as described above, using Tryzol (Invitrogen), followed by DNase treatment and final processing using RNeasy, according to manufacturer instructions (Qiagen). Five to ten microliters of RNA preparation from pooled samples was ligated to GeneRacer adaptor (5'-CGACUGGAGCACGAGGA-CACUGACAUGGACUGAAGGAGUAGAAA-3' (SEQ ID NO: 293)) without prior treatment. Ligated RNA was reverse transcribed using a gene specific primer (cDNA primer: 5'-CTCAAAGCTCTACATCATTATC-3' (SEQ ID NO: 294)). To detect RNAi specific cleavage products, two rounds of consecutive PCR were performed using primers complimentary to the RNA adaptor and RSV A2 N gene mRNA (GR 5' primer: 5'-CGACTGGAGCACGAGGACACTGA-3' (SEQ ID NO: 295) and Rev Primer: 5'-CCACTC-CATTTGCTTTTACATGATATCC-3' (SEQ ID NO: 296)) for the first round, followed by a second round of nested PCR (GRN 5' primer: GGACACTGACATGGACTGAAG-GAGTA-3' (SEQ ID NO: 297) and Rev N Primer: 5'-GCTTT-TACATGATATCCCGCATCTCTGAG-3' (SEQ ID NO: 298)). Amplified products were resolved by agarose gel electrophoresis and visualized by ethidium bromide staining. Specific cleavage products migrating at the correct size were excised, cloned into a sequencing vector and sequenced by standard method.

Sequence Analysis of Clinical Isolates for ALN-RSV01 Target Site Conservation.

Amplification of the RSV N gene fragment containing the ALN-RSV01 recognition site was performed using two-step RT-PCR. Briefly, RNA was reverse transcribed using random hexamers and Superscript III reverse transcriptase (Invitrogen) at 42° C. for 1 hr to generate a cDNA library. A 1200 nucleotide gene specific fragment was amplified using the RSV N forward primer: 5'-AGAAAACTTGATGAAA-GACA-3' (SEQ ID NO: 285) and the RSV N reverse primer: 5'-ACCATAGGCATTCATAAA-3' (SEQ ID NO: 286) for 35 cycles at 55° C. for 30 sec followed by 68° C. for 1 min using Platinum Taq polymerase (Invitrogen). PCR products were analyzed by 1% agarose gel electrophoresis. As a control, a laboratory strain of RSV A long was subjected to the identical procedures for analysis. PCR products were purified using QIAquick PCR purification kit (Qiagen) according to the manufacturer's protocol and sequenced using standard protocols (Agencourt Bioscience, Beverly, Mass.). For each clone, forward and reverse sequence was obtained. Sequences were analyzed and aligned via Clustal W and ContigExpress using Vector NTI software (Invitrogen).

RSV Viral Genotyping.

Genotyping of all 21 isolates received from Mark Van Ranst were performed as described previously (78). Genotyping of the remaining 78 (57 from Dr. John DeVincenzo, University of Tennessee, 13 from Dr. Larry Anderson, Centers for Disease Control and Prevention, and 8 from Dr. Jeffrey Kahn, Yale University) isolates was performed by Dr. Jeffrey Kahn's Laboratory, Department of Pediatrics, Yale University, New Haven, Conn. Analysis of the RSV G gene was performed by first generating cDNA using random hexamers and M-MuLV reverse transcriptase (New England Biolabs, Beverly, Mass.) at 37° C. for 1 hr, followed by PCR amplification using G gene specific primers GTmF: 5'-CCGCGGGTTCTGGCAATGATAATCTCAAC-3' (SEQ ID NO: 299) and subgroup specific G gene specific primers RSV A-GAR2: 5'-GCCGCGTGTATAATTCATAAACCT-TGGTAG-3' (SEQ ID NO: 300) or RSV B-GBR: 5'-GGGGCCCCGCGGCCGCGCATTAATAG-CAAGAGTTAGGAAG-3' (SEQ ID NO: 301) by denaturing at 95° C. for 15 min, followed by 40 cycles of 95° C. for 1 min, 60° C. for 1 min and 72° C. for 1 min, followed by a single 10 min extension at 72° C. using HotStar Taq DNA polymerase (Qiagen). PCR products were analyzed by 2% agarose gel electrophoresis. If an appropriate size PCR product was identified (RSV A: 1200 nt or RSV B: 900 nt), the product was purified using QIAquick Extraction Kit (Qiagen) according to the manufacturer's protocol. Purified PCR products were analyzed by agarose gel electrophoresis and sequenced on a 3730 XL DNA Analyzer (Applied Biosystems, Foster City, Calif.).

Nucleotide sequences were aligned manually and alignment confirmed using Clustal W. RSV A and RSV β isolates were distinguished by comparing G gene nucleotide sequences and laboratory standards. Phylogenetic analysis for RSV A isolates was performed using an aligned 417 nt segment of the G gene corresponding to nucleotide position 5010 to 5426 (GenBank Accession # M74568). Phylogenetic analysis of RSV B isolates was performed using an aligned 288 nt segment of the G gene corresponding to nucleotide positions 5036 to 5323 (GenBank Accession #AF013254). Bootstrap datasets containing 1000 aligned permuted nucleotide sequence sets were produced using SEQBOOT (PHYLIP 3.65). Maximum likelihood phylogenetic trees were obtained using DNAML (PHYLIP 3.65) with default settings and the bootstrap datasets. CONSENSE (PHYLIP 3.65) was used to produce an extended majority rule consensus tree and the trees were MEGA4. Bootstrap values, isolate clustering and previous genotype assignments were used to determine RSV genotypes (FIG. 26).

Results

Bioinformatic Analysis of RSV Genome and Selection of ALN-RSV01.

The three proteins contained within the nucleocapsid (nucleoprotein (N), phosphoprotein (P), and polymerase (L)) are required for various steps within the replication cycle of RSV (Collins, P., K. McIntosh, and R. Chanock. 1996. Respiratory Syncytial Virus, p. 1313-1351, Fields' Virology.), and are among the most highly conserved regions of the RSV genome (Sullender, W. M. 2000. Respiratory syncytial virus genetic and antigenic diversity. Clin Microbiol Rev 13:1-15, table of contents; Sullender, W. M., L. Sun, and L. J. Anderson. 1993. Analysis of respiratory syncytial virus genetic variability with amplified cDNAs. J Clin Microbiol 31:1224-31). To select appropriate siRNAs, GenBank sequences AF035006 (RSV/A2), AF013255 (RSV/B1), AY911262 (RSV/A Long), and D00736 (RSV/18537) were aligned using the Clustal W algorithm to identify conserved 19mers amongst all RSV sequences analyzed. To determine uniqueness of each 19 mer across the human genome, a Basic Local Alignment Search Tool (BLAST) analysis was performed against the Reference Sequence (RefSeq) database. Only siRNAs with homology of 16 nucleotides or fewer to any gene in the human genome were selected for further analysis.

Seventy siRNAs targeting the RSV N, P, and L genes were analyzed in a plaque inhibition assay and 19 exhibited >80% inhibition of plaque formation versus a PBS control at siRNA concentrations of 20 nM (data not shown). Of these 19 siRNAs, the siRNA designated "ALN-RSV01" (FIG. 20) that targets the N gene, consistently demonstrated the highest anti-viral activity. Indeed, ALN-RSV01 showed an IC50 of 0.7 nM in the RSV plaque inhibition assay (FIG. 21).

ALN-RSV01 Inhibition of RSV Primary Isolates.

The relationship between clinical disease and molecular epidemiology of RSV is poorly understood, as several different genotypes cocirculate during most seasons, and dominating genotypes can vary from year to year. It is therefore crucial that any prospective anti-viral agent targets the broadest possible array of identified genotypes. Based on the mechanism of RNAi, it is predicted that sequence identity between an siRNA and its target, implies functional silencing. For this reason, a series of primary isolates (genotype analysis, FIGS. 26A and 26B) taken from nasal washes of children with confirmed RSV disease, were sequenced across the ALN-RSV01 recognition element. Of the RSV primary isolates sequenced, 94% (89/95) showed absolute conservation across the ALN-RSV01 target site. The six isolates that were not 100% conserved each had a single base alteration within the ALN-RSV01 target site. Four had C-U mutations at position 4 with respect to the 5' end of the antisense strand of RSV01, one had A-G mutation at position 7 and one had G-A mutation at position 1. A subset of these 95 isolates was tested in the in vitro viral inhibition assay including one isolate with a mismatch at position 4 and another with a mismatch at position 7 (Table 16). Of these, 12/12 (100%) exhibited ~70% inhibition at 80 nM ALN-RSV01 as compared to PBS control, and all had similar dose response curves for ALN-RSV01 inhibition (FIG. 27).

TABLE 16

| Name | Target site | SEQ ID NO: |
|---|---|---|
| ALN-RSV01 | GGCUCUUAGCAAAGUCAAG | 302 |
| RSV A2 | GGCUCUUAGCAAAGUCAAG | 302 |
| LAM 1238 | GGCUCUUAGCAAAGUCAAG | 302 |
| LEO0713 | GGCUCUUAGCAAAGUCAAG | 302 |
| RUG0420 | GGCUCUUAGCAAAGUCAAG | 302 |
| MOT0972 | GGCUCUUAGCAAAGUCAAG | 302 |
| BEN0819 | GGCUCUUAGCAAAGUCAAG | 302 |
| JEN 1133 | GGCUCUUAGCAAAGUCAAG | 302 |
| HAN 1135 | GGCUCUUAGCAAAGUUAAG | 303 |
| LAP 0824 | GGCUCUUAGCAAGGUCAAG | 304 |
| VA-37C | GGCUCUUAGCAAAGUCAAG | 302 |
| VA-38C | GGCUCUUAGCAAAGUCAAG | 302 |
| VA-54C | GGCUCUUAGCAAAGUCAAG | 302 |
| RSV#32 | GGCUCUUAGCAAAGUCAAG | 302 |

In Vivo Studies of ALN-RSV01.

Figure 22A:
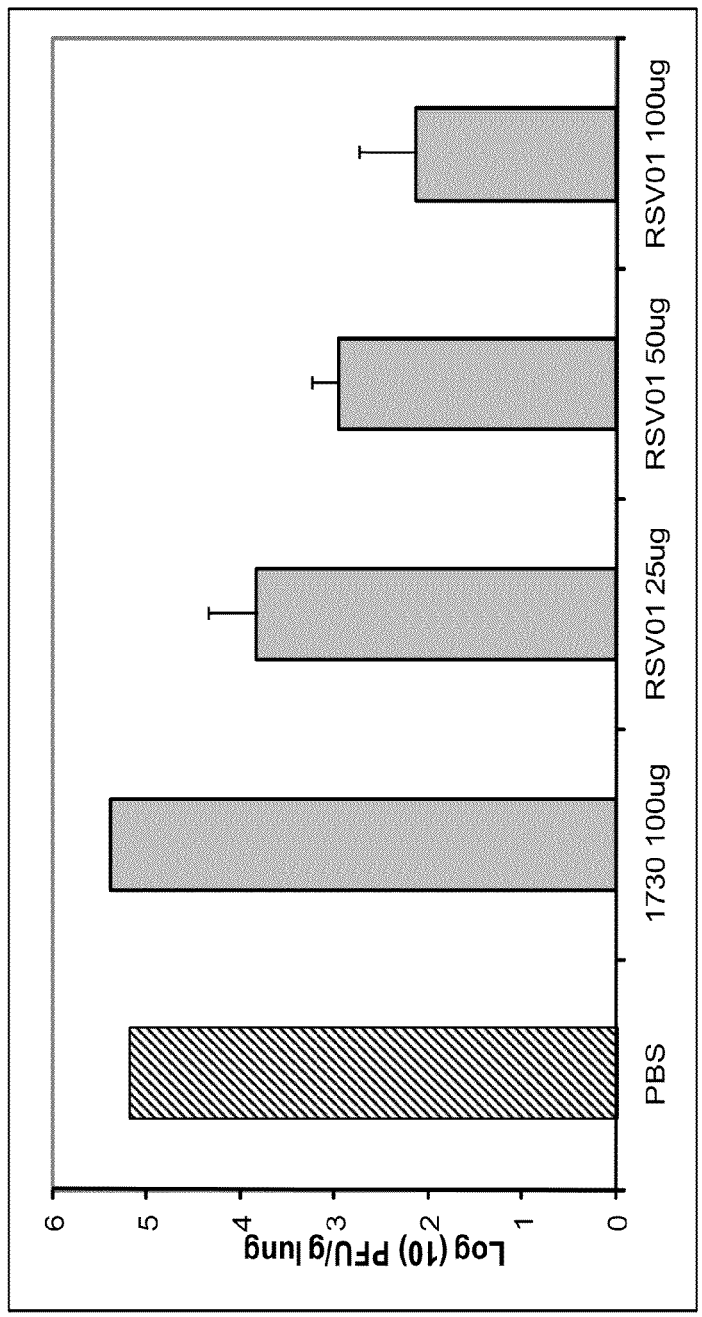

The BALB/c mouse is a well-established model for RSV infection, and was thus chosen as the in vivo system for evaluation of anti-viral efficacy of ALN-RSV01. Initially in a prophylaxis model, siRNA was administered intranasally (i.n.) to mice four hours prior to infection with $10^6$ pfu of RSV/A2. There was dose dependent inhibition of RSV/A2 replication in the lungs of mice, with a 100 µg dose of ALN-RSV01 reducing titers between 2.5 to 3.0 $\log_{10}$ pfu/g lung as compared to either PBS controls or a non-specific siRNA (FIG. 22A). Fifty and 25 µg doses yielded reductions of approximately 2.0 and 1.25 $\log_{10}$ pfu/g, respectively (FIG. 22A).

Figure 22B:
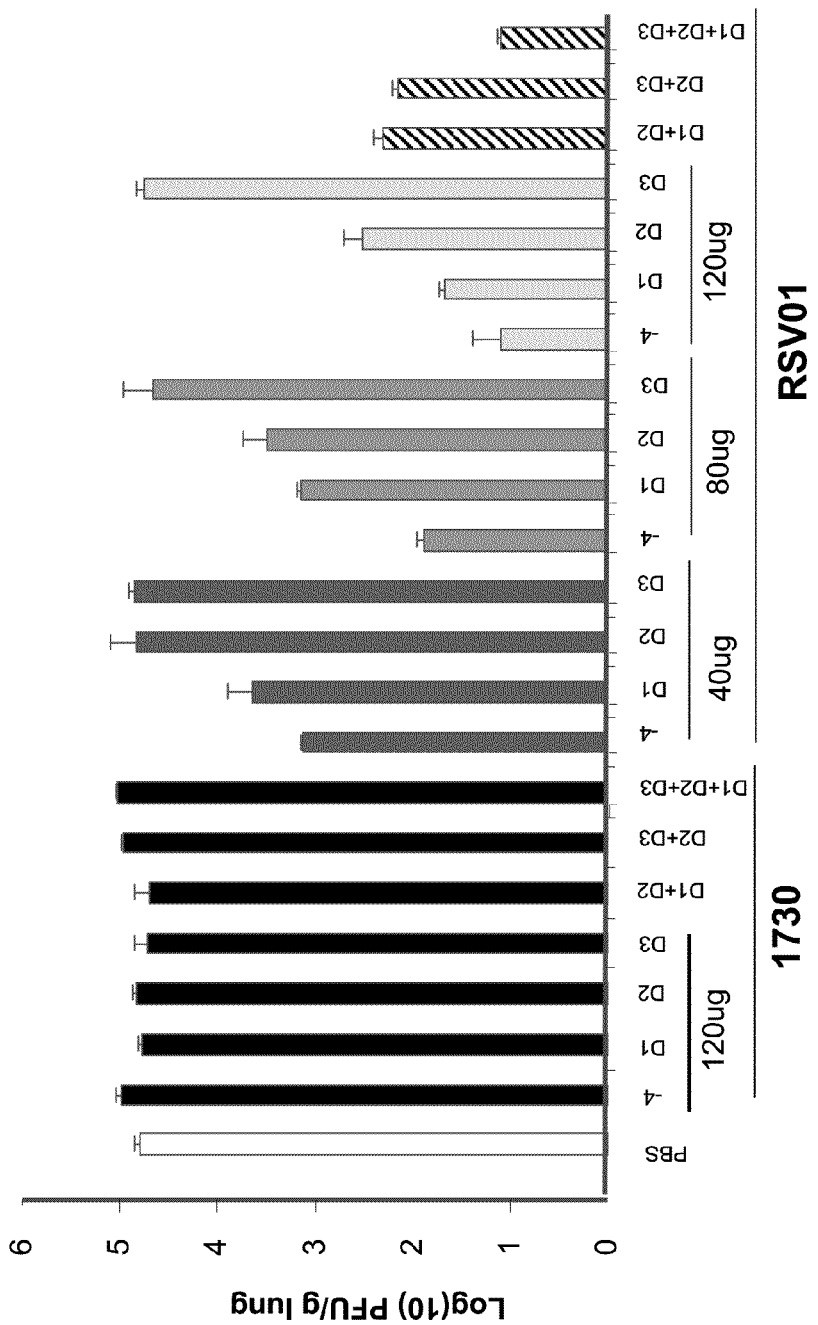

To evaluate the efficiency of viral inhibition in a treatment paradigm, ALN-RSV01 was delivered i.n., in single or multiple daily doses at 1, 2 and/or 3 days post infection. When delivered as a single dose, the most efficacious silencing by ALN-RSV01 occurred in prophylactic (−4 h) dosing in a dose-dependent fashion. As compared to the mismatch control AL-DP-1730, administration of 120 µg of ALN-RSV01 as a single prophylactic dose resulted in maximal viral inhibition, decreasing lung concentrations down to background levels in this assay. When ALN-RSV01 was administered in a treatment regime as a single dose following viral inoculation, anti-viral efficacy was maintained in a dose-dependent manner but found to decrease as a function of time of dosing post viral infection (FIG. 22B). Indeed, by Day 3 post infection, single doses as high as 120 µg did not yield any significant viral inhibition. However, when multiple 40 µg doses of ALN-RSV01 were delivered daily on days 1, 2, and 3, the efficiency of silencing was maintained and viral titers were again reduced to background levels (FIG. 22B).

Figure 22C:
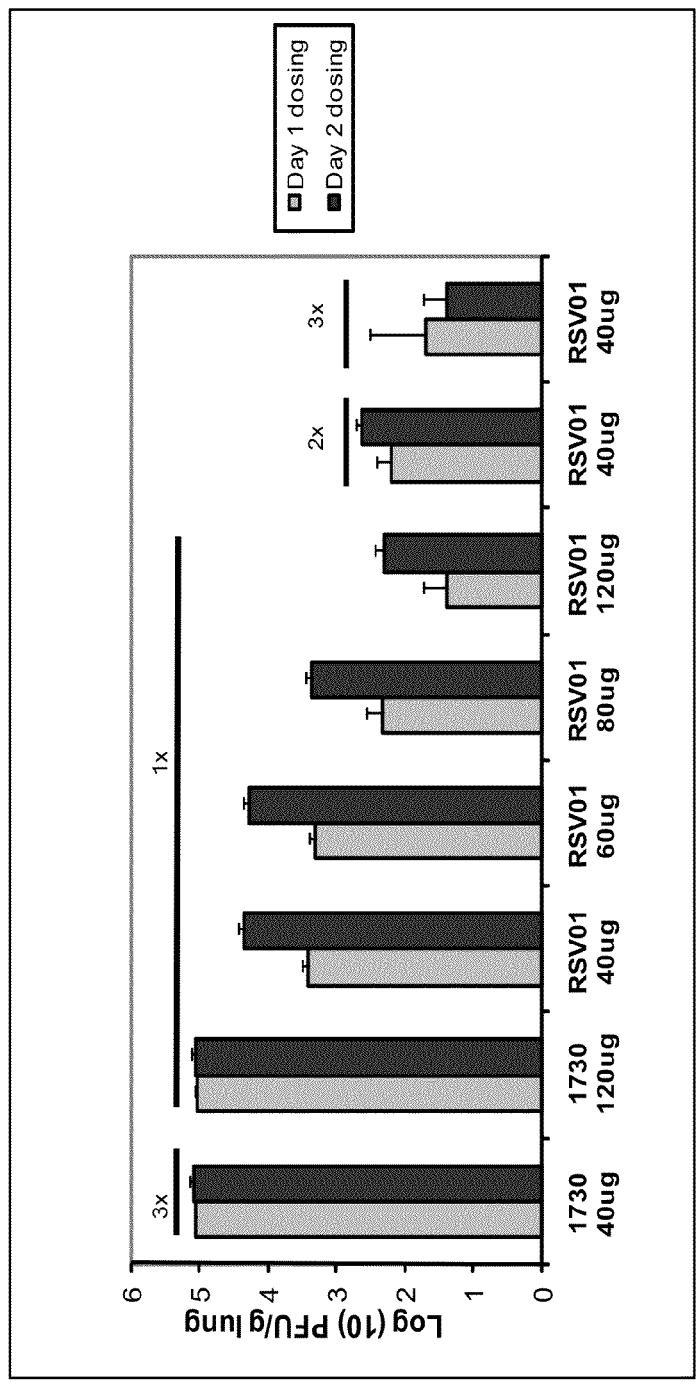

To further explore alternative dosing paradigms that could be employed in future clinical studies, additional multi-dose regimens were evaluated. To this end, RSV-infected mice were treated over a 12 hour period with ALN-RSV01 either in a 2× per day or 3× per day dose regimen. Interestingly, this multiple daily dose regimen of the RSV-specific siRNA (40 µg 3×/day) was found to be as efficacious as a single 120 µg dose (FIG. 22C). In aggregate, these data show that a multi-dose treatment regimen of ALN-RSV01 can provide maximal anti-viral efficacy in a fashion readily applicable to human clinical studies in relevant patient populations.

ALN-RSV01 and Cytokine Induction.

Figure 24C:
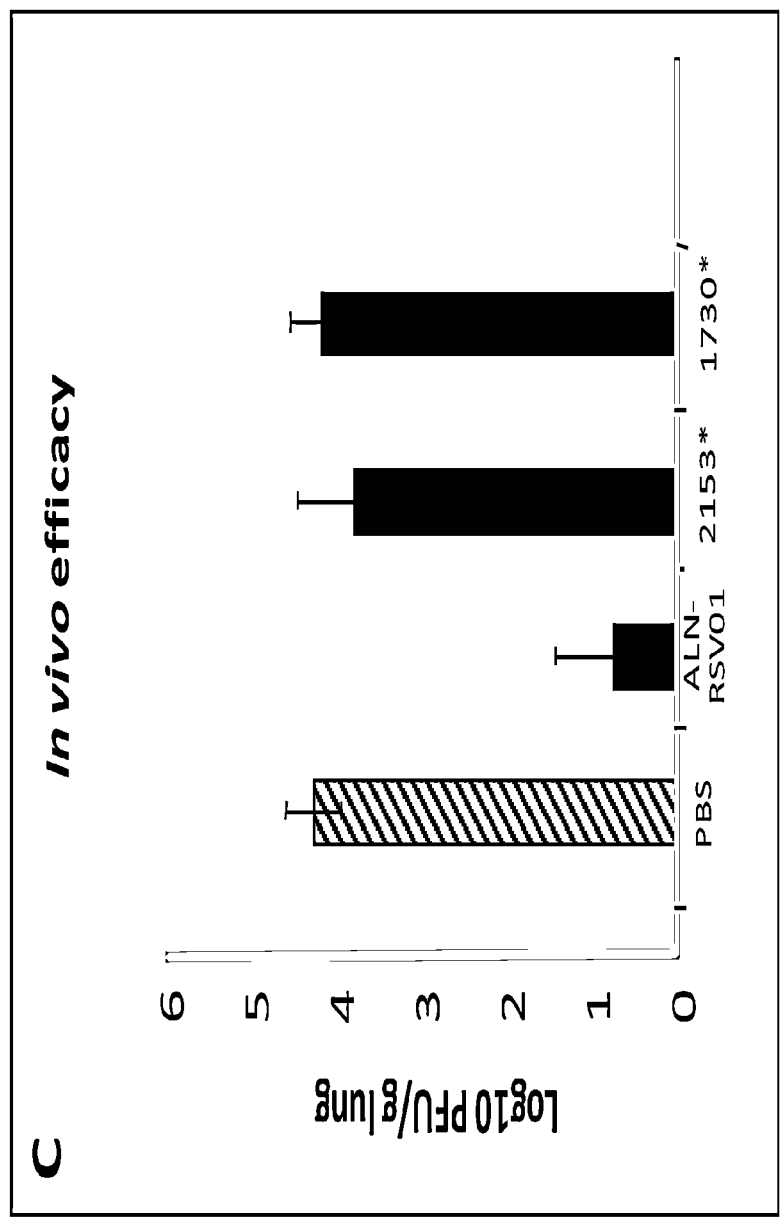

Many nucleic acids, including double-stranded RNA (dsRNA), single-stranded RNAs (ssRNA) and siRNAs have been shown to stimulate the innate immune response through a variety of RNA binding receptors (Robbins, M., A. Judge, L. Liang, K. McClintock, E. Yaworski, and I. MacLachlan. 2007. 2'-O-methyl-modified RNAs act as TLR7 antagonists. Mol Ther 15:1663-9). This stimulation can be monitored in vitro in a peripheral blood mononuclear cell (PBMC) assay (Sioud, M. 2005). Induction of inflammatory cytokines and interferon responses by double-stranded and single-stranded siRNAs is sequence-dependent and requires endosomal localization. (J Mol Biol 348:1079-90.). While an immunostimulatory property of an siRNA could act synergistically with an RNAi-mediated mechanism for the treatment of a viral infection, such a feature might also confound interpretation of results related to an siRNA treatment strategy. Accordingly, ALN-RSV01 was evaluated for its ability to stimulate IFNα and TNFα in vitro by incubating with freshly purified peripheral blood mononuclear cells (PBMCs) as previously described (Hornung, V., M. Guenthner-Biller, C. Bourquin, A. Ablasser, M. Schlee, S. Uematsu, A. Noronha, M. Manoharan, S. Akira, A. de Fougerolles, S. Endres, and G. Hartmann. 2005. Sequence-specific potent induction of IFN-alpha by short interfering RNA in plasmacytoid dendritic cells through TLR7. Nat Med 11:263-70). High concentrations of ALN-RSV01 were used in these assays (133 nM), exceeding the $IC_{50}$ for anti-viral effect by over 100-fold. After 24 hours, only modest levels of both IFNα and TNFα were detected by ELISA, with an average of approximately 147 pg/ml of IFNα (FIG. 23A) and 1500 pg/ml of TNFα (FIG. 23B) induced, as compared to media alone controls To verify that the antiviral activity of ALN-RSV01 was not influenced by this modest induction of cytokines, two non-RSV specific siRNAs previously shown to more significantly induce either IFNα or TNFα, were assayed in our in vivo BALB/c mouse model. Neither AL-DP-1730, a TNFα inducer (FIG. 24A) nor AL-DP-2153, a IFNα inducer (FIG. 24B) inhibited RSV/A2 when administered intranasally (100 µg) into mice, as compared to the strong inhibition observed when delivering ALN-RSV01 (FIG. 24C). Importantly, even 10 fold higher doses of AL-DP-1730 had no effect on RSV levels when delivered prophylactically, 4 hrs prior to infection (data not shown). These data support the conclusion that ALN-RSV01 antiviral effects are mediated via an RNAi mechanism and not via induction of innate immunity.

In Vitro and In Vivo RACE Analysis of ALN-RSV01 Cleavage Product.

The RISC-mediated cleavage of a specific mRNA transcript occurs exactly 10 nucleotides from the 5'-end of the siRNA antisense strand. To definitively confirm an RNAi-mediated mechanism of action for ALN-RSV01, a 5' Rapid Amplification of cDNA Ends (RACE) assay was used. This assay allows the potential capture and sequence analysis of the specific RNAi cleavage product mRNA intermediate following ALN-RSV01 treatment both in vitro and in vivo. Following siRNA transfection (200 nM) into Vero cells and subsequent infection with RSV/A2, a specific cleavage fragment could be detected only in the samples treated with ALN-RSV01 as compared to either PBS or a non-specific siRNA (AL-DP-2153) control (data not shown). In these experiments, 92% of the sequenced clones resulted from site-specific cleavage (between positions 26/27 of RSV/A2 N mRNA) (data not shown). When analyzed in vivo, 60-82% of clones isolated from lung tissue of ALN-RSV01 treated, RSV-infected mice demonstrated site-specific cleavage of the N-gene transcript between positions 26/27 (FIG. 25). Only animals treated with ALN-RSV01, in contradistinction with those treated with PBS or mismatch controls, yielded significant numbers of clones whose sequence was confirmed as the predicted cleavage site (FIG. 25).

Discussion

RSV can be classified into two subgroups, serotype A and B, which differ in all 11 genes identified. Genotypes can vary from year to year with certain serotypes dominating in some years, but co-circulation of multiple RSV strains is commonly observed. Although RSV-A may produce greater viral loads in infants, and RSV-A may produce slightly more severe disease than RSV-B, both RSV-A and RSV-B produce a similar and clinically indistinguishable disease spectrum. In the case of an RNAi therapeutic, broad spectrum activity is achieved by selecting an siRNA molecule whose corresponding mRNA target site is conserved across the various circulating RSV viral isolates. This is achieved for ALN-RSV01 by targeting the relatively conserved viral nucleocapsid which is less prone to mutation than surface viral proteins such as the G or F. Indeed, within RSV, the N gene is among the most conserved, with approximately 86% identity at the nucleic acid level and 96% identity at the amino acid level. Sequence differences within the target site were observed at low frequency in clinical specimens, and largely created a G:U wobble between the antisense strand of the siRNA and the target RSV mRNA. All clinical isolates tested were effectively inhibited in vitro by ALN-RSV01 (FIG. 27). Though the IC 50 for the two G:U wobble isolates was 5 nM (the top of the range), it should be noted that other isolates, namely RUG0420 and MOT0472, both of which show 100% sequence conservation at the ALN-RSV01 target site, also exhibited 5 nM IC50 values. Thus, target site divergence in the non conserved isolates does not account for the slightly higher IC50. It is likely that the growth and replication properties of these isolates account for their slightly higher IC50 values. These primary isolates spanned genotypes A and B indicating that ALN-RSV01 is likely active against all currently circulating strains. In a large series of in vivo studies, ALN-RSV01 was found to be a potent anti-viral in both prophylaxis and treatment paradigms, showing up to 3 log viral reduction as compared to either PBS or non-specific siRNA controls. Bitko et al. and Zhang et al., have also previously demonstrated siRNA inhibition of RSV in BALB/c mice, targeting either the phosphoprotein (P) mRNA or the non-structural one (NS-1) mRNA, respectively, with reductions similar to those described here. While these other siRNAs were effective inhibitors of viral replication in vivo, neither is ideally suited for RNAi therapeutic development. The P gene targeting siRNA of Bitko is directed against a region of the virus that is not conserved across RSV A and B serotypes. Further, the NS-1 targeting siRNA of Zhang et al, is believed to function (at least in part), as an immune modulator, by inhibiting the production of the RSV protein that inhibits IFN induction.

Applications of ALN-RSV01 in clinical settings will require optimization of the dosing strategy in terms of dose level and frequency. In the study described in this Example, multi-dosing with low doses of siRNA was equivalent or slightly more effective when compared to the equivalent total dose delivered in a single administration. Therefore, in certain circumstances, multi-dosing may be a preferred strategy for delivering ALN-RSV01.

Example 17

A Randomized, Double-Blind, Placebo-Controlled Study of an RNAi Therapeutic Directed Against Respiratory Syncytial Virus This Example describes the significant antiviral activity of ALN-RSV01 in adult humans infected with wild-type RSV. Eighty-eight healthy subjects were enrolled into a randomized, double-blind, placebo-controlled trial. A nasal spray of ALN-RSV01 or saline placebo was administered daily for two days before, and for three days after RSV inoculation. RSV was measured serially in nasal washes using multiple different viral assays. The results described below show that intranasal ALN-RSV01 was well-tolerated, exhibiting a safety profile similar to saline placebo. The proportion of culture defined RSV infections was 71.4% and 44.2% in placebo and ALN-RSV01 recipients respectively (P=0.009), representing a 38% decrease in the number of infected and a 95% increase in the number of uninfected subjects. The acquisition of infection over time was significantly lower in ALN-RSV01 recipients (P=0.007 and P=0.032, viral culture and PCR respectively). Multiple logistic regression models showed that the ALN-RSV01 antiviral effect was independent of other factors including pre-existing RSV antibody and intranasal pro-inflammatory cytokine concentrations.

Materials And Methods

Subjects

The study included healthy males age 18-45. Exclusion criteria included: asthma, smoking, fever or symptomatic respiratory infection within the previous 2 weeks, medications for rhinitis within the previous 7 days, contact with people at risk for severe RSV, steroid use in the past month, and chronic sinusitis. PCR testing on day −2 showed no RSV A-B, Influenza A-B, Parainfluenza 1, 2, 3 or Human Metapneumovirus infections.

Study Drug

ALN-RSV01 is a synthetic, double-stranded oligonucleotide. Two 21-nucleotide strands in a staggered duplex are formed by hybridization of two partially complementary single strand RNAs with 19 paired nucleotides and an overhang of two thymidine nucleotides at the 3' end. The antisense strand is complementary to a 19 nucleotide sequence (residues 3-21) of the mRNA encoding the RSV nucleocapsid N protein. ALN-RSV01 is formulated as a sterile phosphate-buffered solution diluted in normal saline before dosing. ALN-RSV01 (75 or 150 mg) or placebo (sterile normal saline) was administered by nasal spray (Becton-Dickinson Accuspray®), 0.5 mL/naris.

Inoculating Virus (RSV)

RSV-A (Memphis 37 strain), from an infant hospitalized for bronchiolitis, was GMP-manufactured using FDA-approved vero cells. The isolate was isolated by plaque-purification and then passaged 5 more times before inoculating subjects. RSV identity was confirmed by IFA, electron microscopy and N-gene sequencing. It was determined to be free of adventitial agents and other human pathogens. Memphis 37 was diluted in 25% sucrose immediately prior to inoculation of subjects by intranasal drops (0.5 mL/naris).

Study Design and Endpoints

The study was a 1:1 randomized, placebo-controlled, double-blind, parallel-group Phase II trial conducted at a single quarantine unit (Retroscreen Virology Ltd, UK). Local regulatory, institutional review board, and Ethics Committee approval was obtained. All subjects provided written informed consent.

Subjects were enrolled through 6 sequential cohorts (FIG. 33). In cohort 1 (N=8), ALN-RSV01 was dosed at 75 mg/day. In cohorts 2-6 (N=80), ALN-RSV01 was dosed at 150 mg/day. Cohorts 2-6 consisted of 8, 18, 16, 24 and 14 subjects respectively. Subjects were admitted to the quarantine unit for 14 days and were dosed with ALN-RSV01 or placebo 32 hrs (Day −1) and 8 hrs (Day 0) prior to RSV inoculation (Day 0). Daily dosing continued after RSV inoculation on Days 1, 2 and 3. The RSV inoculum was determined by plaque assay in HEp-2 cells at the exact time of inoculation of first and last subjects in each cohort. Nasal washes (5 mL normal saline per naris) for viral assays and cytokine measurements were obtained daily on the day of admission to the quarantine unit (Day −2) and on Days 2 through 11. For assessment of upper respiratory signs and symptoms, a physician's daily directed physical exam (DPE, Days-2 to 11) and a twice-daily subject-reported RSV symptom score card (Days −1 to 11) were completed (FIG. 28). Mucus weight for each 24-hour period was recorded from Days −1 through 11. Adverse events were recorded through the Day 28 follow-up visit.

The primary efficacy endpoint was the proportion of subjects who were RSV infected. Infection was pre-specified as two consecutive positive RSV assays, the first occurring between Days 2 and 8 post-inoculation inclusively. Additional antiviral efficacy measures included viral area under the curve (AUC) and peak viral load. Clinical efficacy endpoints examined included total symptom score, total DPE score, and mucus weight.

RSV and Antibody Assays

Nasal washes were collected into cold RSV stabilization media, transported on ice, and placed onto HEp-2 cell monolayers within 30 minutes of collection. Quantitative culture in HEp-2 cell plaque assays was performed in 12-well plates using triplicate 10-fold dilutions of nasal wash as previously described[18]. RSV quantitative standards (RSV-A Long ATCC VR-26) were run in parallel with each plaque assay. Nasal washes containing less than the lower limit of quantification (LLOQ) (<1.7 Log PFU/ml) were considered culture negative.

The quantitative real time RT-PCR (qRT-PCR) assay amplifying an N-gene sequence distinct from that of ALN-RSV01 was performed as previously described[19]. Duplicate specimens were run in 96 well plates incorporating internal standards of RNA extracted from parallel aliquots containing known RSV-A Long quantity as used in the plaque assays. Results are means of duplicates in Log plaque forming unit equivalents/ml (Log PFUe/ml).

Spin-enhanced cultures were performed using confluent HEp-2 cell monolayers on cover slips within shell vials and were inoculated with 200 µl fresh nasal wash and centrifuged at 700×g for 60 minutes. Monolayers were acetone-fixed after 2 days. Cover slips were evaluated for RSV by direct fluorescent antibody techniques using RSV-specific mouse monoclonal antibodies (Bartels, Trinity Biotech, Wicklow, Ireland).

Serum RSV-neutralizing antibodies were measured by a HEp-2 cell RSV 50% microneutralization assay as previously described but performed with Memphis 37 strain. To maximize infection, only subjects with a titer of ≤7.67 MU were included, representing the lower third of the normal distribution in healthy adults (data not shown).

Cytokine Assays

Nasal wash aliquots were analyzed at neat, 1:10 and 1:50 dilutions using Pierce Searchlight chemiluminescent multiplexed sandwich ELISA cytokine arrays (Woburn, Mass., USA) quantifying G-CSF (LLOQ 1.82 pg/mL), IFN-α (LLOQ 7.5 pg/mL), IL-1RA (LLOQ 4.4 pg/mL) and TNF-α (LLOQ 6.7 pg/mL)

Statistical Analysis

Statistical methods used International Conference on Harmonisation guidelines. Continuous values below the LLOQ were set at zero. Continuous efficacy variables, were evaluated using a two-sample t-test. Data not normally distributed was analyzed via the Wilcoxon rank-sum test. Because the outcome of different cohorts may have been affected by unknown factors and differences in RSV inoculum between cohorts, the primary efficacy endpoint comparing proportions of subjects infected was evaluated via a two-sided Cochran-Mantel-Haenszel (CMH) test controlling for cohort. All analyses were performed using SAS® v8.2 or higher for Windows.

Results

Patients

Eighty-eight subjects were enrolled into the study (FIG. 33). All 88 were evaluated for safety, and the 85 who received RSV inoculation were evaluated for efficacy. All subjects who were RSV-inoculated received all study drug doses and evaluations. The treatment groups were well balanced at baseline (FIG. 29).

Antiviral Effect

A significantly lower proportion of ALN-RSV01 treated subjects were infected compared to placebo (FIG. 30). By quantitative culture, ALN-RSV01 was associated with a 38.1% relative reduction in the number of infected subjects and a 95.1% increase in the number of uninfected subjects (P=0.009). This antiviral effect of ALN-RSV01 was consistent across the other viral assays with a similar magnitude of effect demonstrated by qRT-PCR and by spin-culture methods. When only those subjects receiving 150 mg of study drug were evaluated (cohorts 2-6) a statistically significant treatment effect was also observed (data not shown).

The timing of the antiviral effect was also examined. The median incubation period in the placebo group was 3.5 days. By both quantitative culture and qRT-PCR, the acquisition of infection over time was reduced in the ALN-RSV01 group (P=0.0069 and P=0.0321 respectively (FIG. 34). This reduction was observed early within 3-4 days post inoculation. No rebound in acquisition of infection was observed. If the data were censored after day 8, statistical significance remained (P<0.05 for both PCR and culture) (data not shown).

The study was not powered to detect statistically significant effects on viral load. However, study results showed consistent trends towards lower viral load in ALN-RSV01 recipients compared to placebo (FIG. 35), including lower viral AUC and peak viral load (FIG. 35, A-B). Mean daily viral loads (FIG. 35, C-D) were also lower from Days 4-6 (by quantitative culture) or from Days 4-7 (by qRT-PCR) after viral inoculation, with a maximal difference in mean viral load of approximately 1 Log PFU/ml. There were no differences in incubation period or duration of viral shedding between ALN-RSV01 and placebo and no viral rebound was observed (FIG. 35, C-D).

To determine whether the effect of ALN-RSV01 on RSV infection was independent of other variables, multivariate logistic regression analyses were performed evaluating the following variables: treatment assignment (ALN-RSV01 vs. placebo), RSV inoculum, pre-treatment RSV microneutralization titer, and intranasal proinflammatory cytokine concentrations (TNF-α, IFN-α, G-CSF, and IL-1RA). No statistically significant differences in cytokine AUC or peak cytokine concentrations occurred between ALN-RSV01 and placebo groups. The G-CSF concentrations in the ALN-RSV01 group appeared modestly elevated throughout the observation period compared to the placebo group whereas all other cytokine concentrations showed inconsistent trends (FIG. 36). Cytokines were examined by constructing different logistic regression models using pretreatment cytokine concentration (Day −2), cytokine AUC on Days 2-4 following RSV inoculation, and cytokine AUC on Days 2-8 for each cytokine respectively. Representative models are shown in the table of FIG. 31. In all models, including those for G-CSF, ALN-RSV01 was independently associated with reduced infection (by quantitative culture or qRT-PCR, P<0.05).

Clinical Effects

Experimental RSV infection of healthy volunteers produces only mild to moderate upper respiratory tract illness. Within this narrow disease severity spectrum, evaluation of disease measures in subjects treated with either ALN-RSV01 or placebo showed no statistically significant differences (FIG. 35 E-G). Analysis of mean symptom scores over time in all subjects or in those who were RSV-infected showed that the most marked lowering of symptom scores in ALN-RSV01 relative to placebo occurred on Days 4-7 (FIG. 35 H-I). This corresponded to the same time period when there was the greatest reduction in mean daily viral load (FIG. 35 C-D).

Safety

Intranasal ALN-RSV01 was well-tolerated. Adverse events were well balanced between ALN-RSV01 and placebo (FIG. 32), with few moderate adverse events (all of which occurred after discharge from quarantine) and no severe or serious adverse events.

In summary, in this randomized, double-blind, placebo-controlled trial, a statistically significant antiviral effect was demonstrated with the RNAi therapeutic, ALN-RSV01. The proportion of subjects infected as diagnosed by two different culture-based assays was significantly lower in recipients of ALN-RSV01 as compared to placebo (P<0.05) (FIG. 30). Furthermore, acquisition of infection over time as diagnosed by either culture or PCR was also significantly reduced (P<0.01 and P<0.05 respectively) (FIG. 34). Finally, multivariate logistical regression showed that this ALN-RSV01-associated antiviral effect is statistically independent of the possible effects of other variables (FIG. 31). ALN-RSV01 therefore produces a demonstrable antiviral effect.

Substantial evidence shows that RNAi is the mechanistic basis for the ALN-RSV01 antiviral effect. First, ALN-RSV01 reduces RSV in a murine model in which mismatched siRNAs (differing from ALN-RSV01 in as few as 4 nucleotides) produce no anti-RSV effect. Second, the cleavage products resulting from RNAi-mediated silencing of the RSV N-protein transcript have been observed in the lungs of RSV-infected mice treated with ALN-RSV01. Third, immunosilent siRNAs targeting the RSV N gene are active against RSV in mice whereas mismatched siRNAs with potent in vitro immunostimulatory activity do not demonstrate anti-RSV activity in mice (R. Meyers, unpublished data). And lastly, substantial evidence within this trial itself indicates that ALN-RSV01 is contributing to the observed antiviral effect independent of intranasal cytokine induction. Multivariate logistic regression models show that the statistically significant ALN-RSV01 antiviral effect was independent of the other variables examined, including levels of intranasal cytokines. Indeed, where a cytokine effect was evident, there was an association with increased rather than decreased infection (FIG. 31), likely due to RSV infection itself stimulating cytokines within human respiratory secretions. Thus, an antiviral effect which strongly appears mediated through RNAi has been demonstrated.

The timing of ALN-RSV01 can be further optimized to achieve maximal reductions in viral load or RSV disease measures if infection did occur. Here, ALN-RSV01 was dosed twice prior to RSV inoculation and three times subsequently. ALN-RSV01 was stopped 2-4 days prior to the occurrence of peak viral load and peak clinical symptoms of infection. The incubation period of RSV in the placebo arm was a median of 3.5 days; thereafter, a consistently lower daily viral load was found in ALN-RSV01 recipients, and the antiviral effect appeared to continue through Days 6-7 post-inoculation with a maximum 1 Log reduction in viral load compared to placebo. Concurrent to this transient reduction in viral load, the most marked lowering of symptom scores for the ALN-RSV01 group relative to placebo occurred on Days 4-7. In children, lower RSV loads are associated with decreased requirements for intensive care, decreased respiratory failure and shorter hospitalizations. Therefore, robust reductions in RSV load, if achieved, are likely to translate into reduced disease severity and clinical benefit. Optimal dosing of ALN-RSV01, so as to be administered through times of active viral replication, may maximize its effect on viral dynamics and clinical outcomes.

There is a time delay in natural RSV infection: RSV infects and causes symptoms in the upper respiratory tract before subsequently moving to involve the lungs. In light of the significant effect of intranasal ALN-RSV01 shown here on preventing RSV infection when administered prior to and early during the course of infection, aerosolized ALN-RSV01 can be utilized to alter the spread of an early RSV infection into the lower airways. The delivery of aerosolized drug simultaneously to both the upper and lower respiratory tracts at varying time intervals following infection initiated by relatively low inoculum natural RSV exposures can assist in the optimization of anti-RSV therapy.

Example 18

ALN-RSV01 Specificity in Humans as Analyzed by 5' Race Assay

This Example confirms that the antiviral effect of ALN-RSV01 in humans is mediated by RNAi. The 5' RACE assay is discussed above in more detail (e.g., FIG. 25 and accompanying description).

RNA isolation: Total RNA was purified from nasal samples using RNA STAT-50 LS reagent (Tel-Test) according to manufacturer's instructions. The 5' RACE assay was done using a modified GeneRacer kit (Invitrogen cat#L1502-01). To detect cleavage product, 3 rounds of consecutive PCR were performed using primers complementary to the RNA adaptor and RSV A2 N gene mRNA (GR5' and Rev for the 1st PCR round; GRN5' and RevN—for the nested PCR and enrichment PCR).

| Name | Sequence 5' - 3' | SEQ ID NO: |
|------|------------------|------------|
| GR 5' | CGACTGGAGCACGAGGACACTGA | 295 |
| GRN 5' | GGACACTGACATGGACTGAAGGAGTA | 297 |
| Rev. | CCA CTC CAT TTG CTT TTA CAT GAT ATC C | 296 |
| RevN | GCT TTT ACA TGA TAT CCC GCA TCT CTG AG | 298 |

Amplified products were resolved by agarose gel electrophoresis (2.3% agarose) and visualized by ethidium bromide staining. The identity of specific cleavage products was confirmed by cloning of the PCR product and sequencing of individual clones.

Figure 37A:
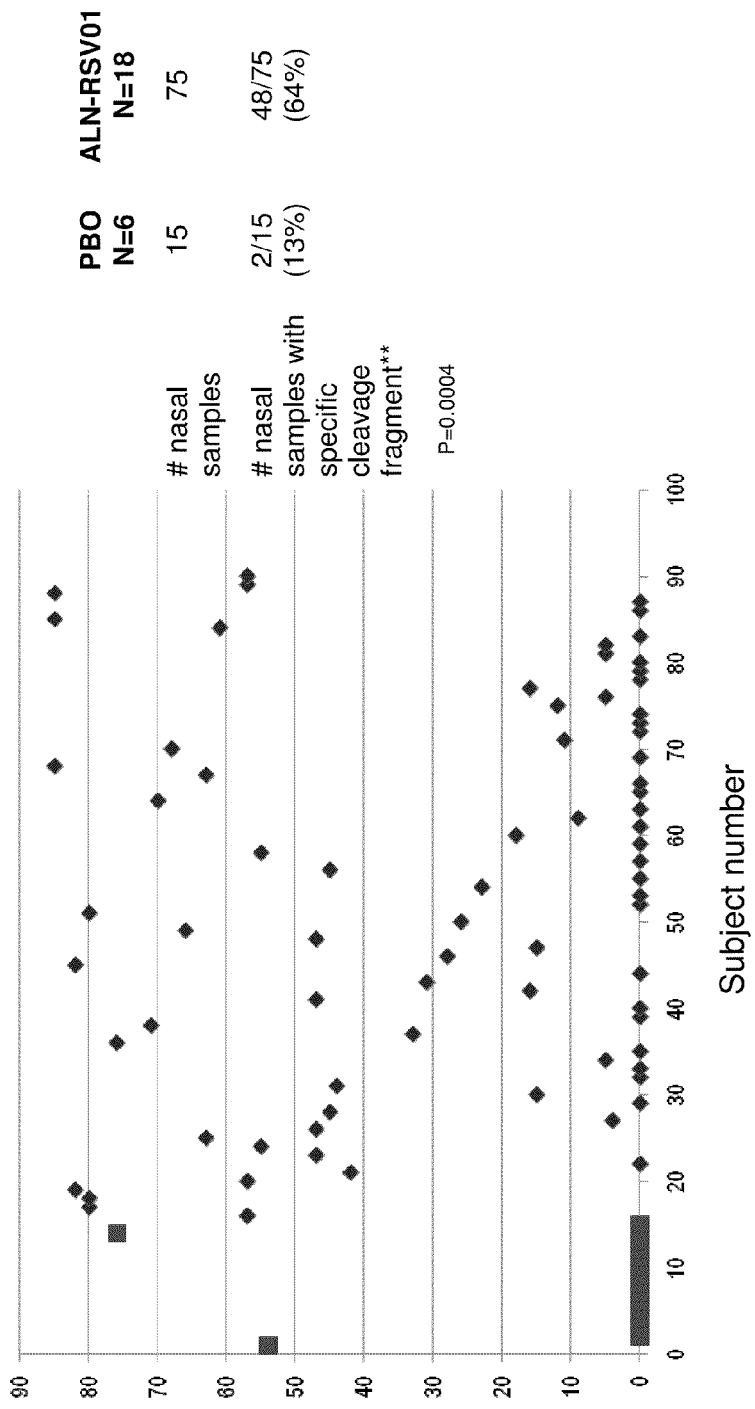
Figure 37B:
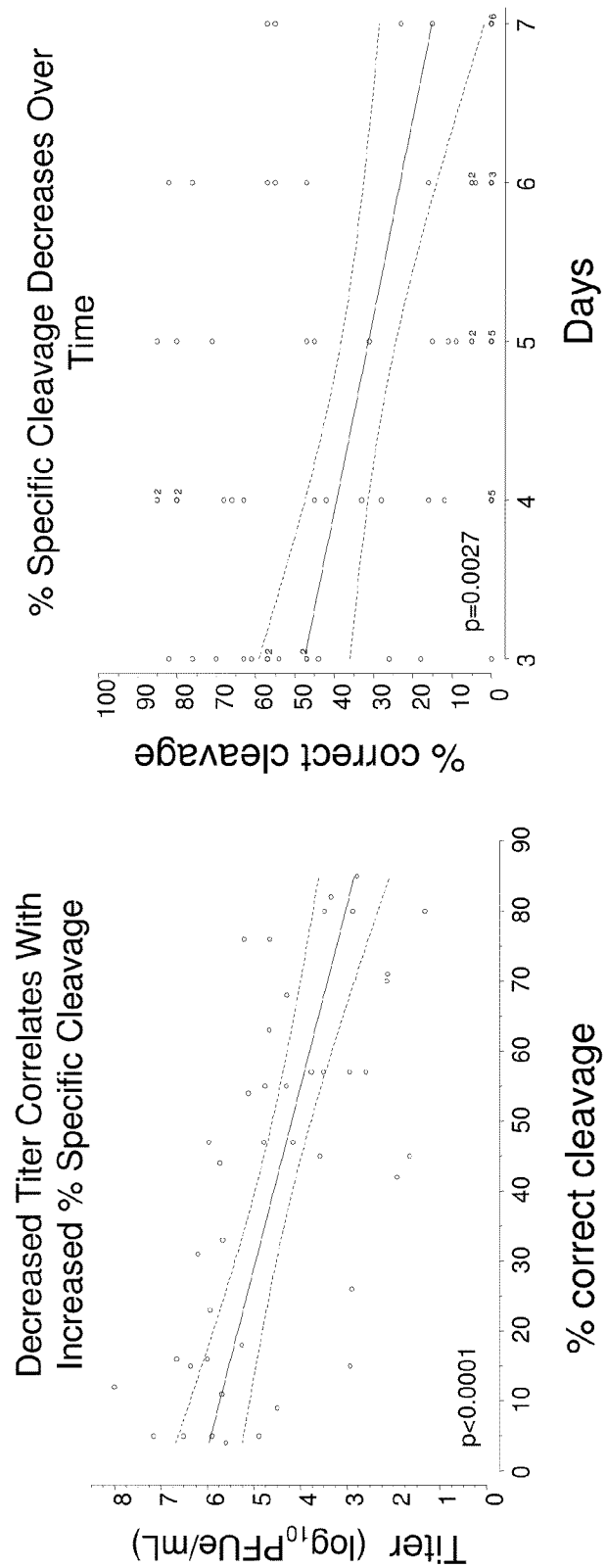

The results are depicted in FIG. 37. FIG. 37A shows that treated patients have a significantly increased frequency of the fragment predicted by specific ALN-RSV01 iRNA-mediated cleavage. Moreover, an increase in specific cleavage correlates strongly with a decrease in observed viral titer, providing a further indication that the antiviral effect is mediated by RNAi (FIG. 37B). FIG. 37B also shows that the % of specific cleavage observed decreases over time post-dosage. Thus, patient analysis at times proximal to drug dosing may be advantageous when measuring this particular marker of drug efficacy.

Example 19

A Multi-Center, Randomized, Double-Blind, Placebo-Controlled Study of the Safety and Antiviral Activity of Aerosolized ALN-RSV01 Plus Standard of Care in Lung Transplant Recipients Infected With RSV This prophetic example describes embodiments of the invention relating to the treatment of patients who have received lung transplants. The skilled artisan will recognize that many aspects of the methods described below are equally applicable to treating a patient who has not received a lung transplant but is infected with RSV or at risk of RSV infection.

A study is conducted to assess the safety, tolerability, and antiviral activity of aerosolized ALN-RSV01 versus placebo, administered in a multiple-dose schedule (once daily for 3 days) to lung transplant recipients infected with respiratory syncytial virus (RSV). Other objectives include evaluating the effects of ALN-RSV01 versus placebo on the clinical endpoints of RSV infection in lung transplant patients; determining RSV infection characteristics by quantitative RT-PCR (qRT-PCR) analysis of nasal swab and sputum samples, including peak viral load, time to peak viral load, duration of viral shedding, and viral area under the concentration time curve (AUC); and characterizing plasma pharmacokinetics of aerosolized ALN-RSV01.

Study design: randomized, placebo-controlled, double-blind study is undertaken to assess the safety and efficacy of intranasal ALN-RSV01 administered to lung transplant recipients infected with RSV. A total of 3 doses of ALN-RSV01 are administered to each subject. Up to 21 lung transplant patients with signs (e.g., decrease in FEV1 and/or fever) and symptoms of respiratory infection (e.g., new onset rhinorrhea, sore throat, nasal congestion, cough, wheezing, headache, myalgia, chills, and/or shortness of breath) will be instructed to present to a determined site for screening as soon as possible (e.g., within 0 to 5 days) after identification of the first symptoms.

Patients will have RSV infection confirmed, be randomized to a treatment, and have administration of study medication initiated as soon as possible, e.g., not more than a total of 7 days after onset of signs and symptoms of RSV infection.

Consented eligible patients with positive RSV results will be randomized (2:1) to receive either ALN-RSV01 or placebo (sterile normal saline 0.9% for respiratory administration (saline)) by inhalation once daily for 3 days (Study Days 0, 1, and 2). In addition, all patients will receive the standard of care (SOC) for RSV infection per institutional guidelines or study investigator practices which may include inpatient hospitalization or out-patient care.

Patients with confirmed RSV infection who are randomized to treatment will have nasal swab and sputum samples for RSV determination by quantitative (q)RT-PCR collected daily for 7 days (Day 0 up to Day 6), followed by every other day up to Day 14 days (Day 8, 10, 12, and 14).

Daily outpatient safety assessment visits and respiratory sample collection (nasal swab and sputum) may take place at the institution or at the subject's home under the care of a visiting nurse trained in the study procedures. Assessment of safety may occur up to and include the Day 30 visit (±3 days).

During the Day 90 (±7 days) visit, the following events will be assessed: survival, acute lung rejection, Bronchiolitis obliterans (BOS), intubation, incidence of other viral, bacterial, or fungal respiratory infections FEV1. Total time on study will be 93 days±7 days Dosage, route of administration and duration of treatment of investigational drug and control: Patients randomized to ALN-RSV01 will receive aerosolized ALN-RSV01 (0.6 mg/kg) via a nebulizer, such as a PARI eFlow™ 30 L nebulizer, and administered by inhalation once daily for 3 days (Days 0, 1, and 2). All doses of ALN-RSV01 will be administered at the study center by trained study personnel, and the first dose will be administered with an Investigator on site. The interval between doses of study medication should ideally be ~24 hours, but should not be less than 12 hours and not more than 36 hours.

For patients receiving bronchodilator therapy, an attempt should be made to administer study medication within 1 hour after administration of bronchodilator therapy.

For patients receiving SOC including ribavirin (either by inhalation three times per day (TID), inhalation overnight for 12-16 hours, or by intravenous (IV) administration), study medication should be given 1 to 2 hours prior to the first administration of ribavirin. Subsequent doses of study medication should be given at the same time of day as the first, 1-2 hours prior to the administration of ribavirin with an approximate 24 hour (12-36 hours) dosing interval between doses of study medication.

For placebo, randomized patients will receive aerosolized sterile normal saline via PARI eFlow® 30 L nebulizer and administered by inhalation once daily for 3 consecutive days. Schedule and timing of placebo with regard to ribavirin and bronchodilators should be the same as above.

Study Assessments and Endpoints: Demographic Data and Medical History: Demographic data, lung transplant related information, and a complete medical history will be obtained at Screen (Day −2 to Day 0).

Physical Examinations: A complete physical examination (PE) will be performed at Screen (Day −2 to Day 0), on Day 14, and during the follow-up visit on Day 30. A Directed Physical Examination (DPE) will be conducted at Screen (Day −2 to Day 0) and prior to administration of study medication on Days 0, Day 1, and Day 2; daily on Days 3 to 6, on Day 14, and during the follow-up visits on Day 30. DPE will be performed daily for the duration of the inpatient period for patients hospitalized beyond Day 6. The DPE will focus on the evaluation of respiratory-related and infection-related symptoms, using the DPE worksheet will include review of the following body systems: Head, Eyes, Ears, Nose and Throat, Respiratory System, Cardiovascular System, and Vital Signs.

Vital signs (blood pressure, pulse rate, oral body temperature, and respiratory rate) will be measured at Screen (Day −2 to Day 0); Days 0, 1 and 2 predose and 1 hour post dose; Days 3 to 6, Days 8-14, and during the follow-up visit on Day 30. Vital signs will be assessed daily for the duration of the inpatient period for patients hospitalized beyond Day 6. Blood pressure (systolic and diastolic), pulse rate, and respiratory rate will be obtained. Preferably, each patient's blood pressure will be taken using the same arm throughout the study. Pulse rate will be counted for 20 seconds to one minute and recorded in beats per minute (bpm). Respirations will be recorded in breaths per minute. Body temperature will also be measured.

Height and Weight: Weight (kilograms) will be obtained during the complete physical examination at Screen (Day −2 to Day 0) and Day 14, and during the follow up visit on Day 30. Height (centimeters) will be obtained only at Screen (Day −2 to Day 0).

Treatment-Emergent Adverse Events: Treatment-emergent adverse events will be evaluated daily from Day 0 (postdose) through Day 30. After the Day 30 visit, newly reported changes in FEV1 (Volume of air expired during the first second of the FVC (Volume expired when going from complete inhalation to complete exhalation as hard and fast as possible) maneuver) or changes in Bronchiolitis obliterans (BOS) classification will be documented in the patient Case Report Form (CRF) but will not be considered adverse events.

Concomitant Medications: Use of concomitant immunosuppressant, respiratory, and antimicrobial medications will be recorded in the source documents and on the patient's CRF. Any changes in prior or concomitant medications during the study will also be recorded on the CRF.

Electrocardiogram: A standard 12 lead Electrocardiogram (ECG) will be obtained at Screen (Day −2 to Day 0) and at Day 14. The PI or designee is responsible for reviewing the ECG to assess whether the ECG is within normal limits and to determine the clinical significance of the results. These assessments will be recorded on the CRF. For any clinically significant abnormal results, the PI or Sub investigator must contact the Medical Monitor to discuss continued participation of the patient in the study.

Chest X-ray: Chest X-ray: A standard chest x-ray will be obtained at Screen (Day −2 to Day 0).

Spirometry: Spirometry will be performed at Screen (Day −2 to Day 0), Day 0, 1, and 2 (predose and 1 hour post dose), on Days 3 to 6 and on Days 14, 30 and 90. All spirometry assessments should be performed after vital signs are measured. Spirometry performed at Screening, Day 30, and Day 90 must be performed on the same machine having the same calibration for internal consistency, and should include absolute values as well as % predicted. For patients hospitalized beyond Day 6, spirometry will be performed daily for the duration of the inpatient period up to Day 14 or until discharge, whichever comes first. Spirometry provides an objective method for assessing the mechanical and functional properties of the lungs and chest wall. Spirometry measures include: Lung capacities e.g., FVC (volume expired when going from complete inhalation to complete exhalation as hard and fast as possible), which provide a measurement of the size of the various compartments within the lung; Volume parameters and flow-rates which measure maximal flow within the airways: FVC is the volume expired when going from complete inhalation to complete exhalation as hard and fast as possible, The FEV1 is the amount expired during the first second of the FVC maneuver; FVC and FEV1 will be measured according to the American Thoracic Society/European Respiratory Society guidelines. If a patient's handheld spirometer does not record each of the above protocol specified parameters they may still be enrolled. At a minimum, the FEV1 will be recorded in the source documentation and Case Report Form (CRF).

Pulse Oximetry: A pulse oximetry reading to assess percent of hemoglobin saturated with oxygen is to be collected at Screen (Day −2 to Day 0), Day 0 to 6, on Day 14, and during the follow-up visit on Day 30. Pulse oximetry will be assessed daily for the duration of the inpatient period for patients hospitalized beyond Day 6 or until discharge from the hospital, whichever comes first.

Clinical Laboratory Tests: Blood and urine samples will be obtained for clinical laboratory testing at Screen (Day 2 to Day 0), on Day 0, 1, and 2 (predose), once daily on Day 3 and Day 6, and Days 14 and Day 30 and will be analyzed by Quintiles Central Laboratory, Morrisville, N.C. Instructions for processing samples for clinical laboratory assessment are provided in the Quintiles Laboratory Manual. Hematology, Clinical Chemistry, and Urinalysis assessments will include the following: Hematology: Red blood cell (RBC) count, white blood cell (WBC) count with differential (lymphocytes, monocytes, eosinophils, basophils, neutrophils), mean corpuscular volume (MCV), mean corpuscular hemoglobin (MCH), mean corpuscular hemoglobin concentration (MCHC), hemoglobin (Hgb), hematocrit (Hct) and platelet count; Clinical chemistry: Total bilirubin, alkaline phosphatase, gamma glutamyltransferase, aspartate transaminase (AST [SGOT]), alanine transaminase (ALT [SGPT]), lactate dehydrogenase (LDH), creatinine, blood urea nitrogen (BUN), total protein, glucose, sodium (Na), potassium (K), calcium (Ca), chloride (Cl); Urinalysis: Visual inspection for appearance and color; dipstick for pH, specific gravity, ketones, protein, glucose, bilirubin, nitrite, urobilinogen, occult blood. In the event of an unexplained clinically significant abnormal laboratory test occurring after study medication administration, the test may be repeated and followed up at the discretion of the principal investigator (PI) or Sub-investigator until it has returned to the normal range and/or a diagnosis is made to adequately explain the abnormality. Samples for Clinical Laboratory Assessments should be packaged and shipped to the central laboratory for analysis according to instructions provided in the Quintiles laboratory manual.

Pregnancy Test: Urine and/or serum pregnancy tests will be performed at Screen (Day −2 to Day 0). See the Quintiles laboratory manual for details.

Other Laboratory Assessments: Blood samples for cytokines/C-reactive protein (CRP) will be obtained during Screen (Day −2 to Day 0), and at intervals during the treatment period. Blood sample collection times for cytokines and CRP are as follows: For hospitalized patients, samples are to be obtained on Day 0: predose, 2, 4, 6, and 8 hours after administration of Study Drug; Day 1: predose; Day 2: predose, 2, 4, 6, and 8 hours after study medication administration; and Day 3: 24 hours after the last dose. For outpatients, samples should be obtained on Day 0: predose, 2, 4, and 6 hours after administration of Study Drug; Day 1: predose; Day 2: predose, 2, 4, and 6 hours after study medication administration; and Day 3: 24 hours after the last dose. Cytokine analyses will include the following: CRP (C-reactive protein), interferon (IFN), interleukin (IL) 1ra, IL-6, tumor necrosis factor (TNF)-, and granulocyte colony stimulating factor (G-CSF). Samples for the cytokine/CRP panel should be packaged and shipped to the central laboratory for analysis, according to instructions provided in the Quintiles laboratory manual.

Patient Symptom Card: Acute respiratory symptoms will be self-reported by patients using a Patient Symptom Card. Patient Symptom cards must be filled out twice daily (morning and evening) from Day −2 to Day 14. A sample Patient Symptom Card is presented in Error! Reference source not found. The Patient Symptom Card was adopted for use in the current study because it was developed for scoring acute, nonspecific respiratory symptoms, in contrast to well-known asthma and chronic obstructive pulmonary disease (COPD) questionnaires which focus on specific respiratory symptoms over prolonged periods of time. Symptoms to be assessed include runny nose, stuffy nose, sneezing, sore throat, earache, malaise, cough, shortness of breath at rest, headache muscle and or joint aches, chills, wheezing, chest pain during breathing, and blood in sputum; symptoms will be scored on a scale of 0-3, as follows: (O) Symptom not present; (1) Mild symptom; (2) Moderate symptom; and (3) Severe symptom. Symptoms with scores of 1, 2 or 3 will be reported as adverse events (AEs) by the PI.

Acute Rejection/Bronchiolitis Obliterans: Patients will be evaluated for evidence of acute rejection of the transplant and for the presence or changes in staging of Bronchiolitis Obliterans Syndrome (BOS) through Day 90.

Occurrence of Other Bacterial, Viral or Fungal Respiratory Infections: Patients will be evaluated for occurrence of diagnosed and documented bacterial, viral or fungal respiratory infections (other than RSV) through Day 90. Colonization should not be included.

RSV Infection Characteristics: Nasal swabs and sputum samples for analysis of RSV titer by qRT-PCR (central RSV laboratory) will be obtained at Screen (Day −2 to Day 0), predose on Days 0, 1 and 2, once daily on Days 3 to 6, then once daily on Days 8, 10, 12, and 14. Samples of BAL fluid will be reserved when available and tested for viral titer by qRT-PCR. Characteristics of RSV kinetics to be evaluated from nasal swab samples will include: Duration of viral shedding (Days) from Day −1 to Day 14 of study; Peak viral load (Plaque forming unit equivalent (PFUe)/mL); Time to peak viral load (Days); Mean daily viral load (PFUe/mL); and Overall viral load (based on area under the concentration-time curve [AUC] in PFUe/mL/day). Nasal swabs, sputum samples, and samples of Bronchioalveolar lavage (BAL) fluid must be processed for shipment to the central RSV laboratory; instructions for processing and shipping of these samples are provided in Quintiles laboratory manual.

Pharmacokinetics of ALN-RSV01: Pharmacokinetic assessments will include determination of ALN-RSV01 concentrations in plasma and calculation of derived Pharmacokinetic (PK) parameters from hour 0 on Day 0 to 24 hours after the last dose of ALN-RSV01. Sampling times will be as follows: predose, 2, 5, 10, 15, and 30 minutes on Day 0; predose on Day 1; predose, 2, 5, 10, 15, and 30 minutes on Day 2; and 24 hours after the last dose of study medication on Day 3. PK Parameters that will be calculated (data permitting) include: trough plasma concentration [Cpre]; maximum plasma concentration [$C_{max}$]; time to attain maximum plasma concentration [tmax]; apparent terminal elimination half-life [t1/2]; apparent total body clearance [CL/F]; apparent volume of distribution [Vd/F]; and area under the concentration-time curve [AUC0-last].

Safety Analysis: During the study period and Day 30 Follow-up: Vital signs, pulse oximetry, spirometry, adverse events, concomitant medications, clinical laboratory testing, blood sampling for cytokines/CRP, complete and directed physical examination will be performed. Interim blinded safety reviews will also be performed after 6 and 12 patients complete their Day 6 assessments to review safety aspects of the study.

Efficacy Analysis: Efficacy assessments will include changes in RSV viral kinetics based on centralized quantitative RT-PCR (qRT-PCR) analysis of nasal swabs and sputum, (as well as, where available BAL samples), and patient symptom scores.

For the Day 90 Follow-up: Survival and FEV1 will be recorded. Any occurrences of the following events during the study up to the Day 90 visit will be recorded: acute lung rejection, BOS, requirement for intubation, other viral, bacterial, or fungal respiratory infections.

Pharmacokinetic assessments will include determination of ALN-RSV01 concentrations in plasma and derived PK parameters from hour 0 to 24 hours after the last dose of ALN-RSV01: trough plasma concentration [Cpre], maximum plasma concentration [$C_{max}$], time to attain maximum plasma concentration [tmax], apparent terminal elimination half-life [t1/2], apparent total body clearance [CL/F], apparent volume of distribution [Vd/F], and area under the concentration-time curve [AUC0-last].

Results: ALN-RSV01 is shown to be a safe and effective treatment for the prevention or treatment of RSV infection in human lung transplant recipients.

This application incorporates all cited references, patents, and patent applications by references in their entirety for all purposes.

What is claimed is:

1. A method of reducing the risk of Respiratory Syncytial Virus (RSV) associated bronchiolitis obliterans syndrome (BOS) in a subject, comprising administering to said subject a composition comprising a therapeutically effective amount of a dsRNA that targets a P, N, or L gene of RSV wherein the dsRNA comprises a sense strand and an antisense strand and each strand is 15-30 nucleotides in length, wherein the antisense strand of the dsRNA targeting the N gene is complementary to at least 15 contiguous nucleotides of SEQ ID NOS: 277-284.

2. The method of claim 1, wherein the sense strand is selected from SEQ ID NOs: 3-116, 231-249, and 269-276, and the antisense strand is selected from SEQ ID NOs: 117-230, 250-268, and 277-284.

3. The method of claim 1, wherein said subject is a human lung transplant recipient.

4. The method of claim 1, wherein said subject is receiving bronchodilator therapy.

5. The method of claim 1, wherein ribavarin is administered to said subject.

6. The method of claim 1, wherein said administration is intranasal or intrapulmonary.

7. The method of claim 6, wherein said intrapulmonary administration is by inhalation of said composition.

8. The method of claim 1, wherein said composition is administered as an aerosol.

9. The method of claim 8, wherein said aerosol is a nasal spray.

10. The method of claim 8, wherein said aerosol is produced by a nebulizer.

11. The method of claim 10, wherein said nebulizer is a PARI eFlow® 30L nebulizer.

12. The method of claim 1, comprising administering a plurality of doses of said composition.

13. The method of claim 12, wherein one of said plurality of doses is administered daily.

14. The method of claim 12, wherein said plurality of doses is two or three doses.

15. The method of claim 12, wherein said subject is presently infected with RSV when the first of said plurality of doses is administered.

16. The method of claim 12, wherein said administering of said plurality of doses is by inhalation and delivers a total dose of between 0.1 and 0.6 mg/kg of anhydrous oligonucleotide to said subject.

17. The method of claim 1, further comprising determining a characteristic of RSV infection, wherein said characteristic is selected from RSV mRNA, RSV peak viral load, time to peak RSV viral load, duration of RSV viral shedding, RSV viral AUC, or RSV titer.

18. The method of claim 1, wherein said administering reduces RSV protein, RSV mRNA, RSV peak viral load, time to peak RSV viral load, duration of RSV viral shedding, RSV viral AUC, or RSV titer in a cell of the respiratory tract of said subject.

19. The method of claim 1, wherein said administration of said composition to said subject is started within seven days of onset of symptoms of RSV infection, wherein said symptoms comprise a decrease in FEV1, fever, new onset rhinorrhea, sore throat, nasal congestion, cough, wheezing, headache, myalgia, chills, or shortness of breath.

20. The method of claim 1, wherein said administration of said composition improves FEV1 or causes a reduction in one or more symptoms of RSV infection in said subject relative to a placebo, wherein said symptoms are selected from the group consisting of fever, new onset rhinorrhea, sore throat, nasal congestion, cough, wheezing, headache, myalgia, chills, or shortness of breath or prevents a reduction in lung function for at least 90 days as determined by measurement of a FEV1 in said subject.

21. The method of claim 17, wherein said characteristic of RSV infection is determined by quantitative RT-PCR (qRT-PCR) analysis of a nasal swab sample and/or a sputum sample from said subject.

22. The method of claim 4, wherein said human lung transplant recipient is administered said composition within one hour of receiving bronchodilator therapy.

23. The method of claim 5, wherein said subject is administered said composition one to two hours before administration of ribavirin.

24. The method of claim 1, wherein the method prevents a reduction in lung function for at least 90 days as determined by measurement of a FEV1 in the lung transplant recipient.

25. The method of claim 1, wherein the dsRNA comprises one of the following sense strand and antisense strand pairs:

| SEQ ID NO. | Sense | SEQ ID NO. | Antisense |
|---|---|---|---|
| 3 | GGAUCCCAUUAUUAAUGGAdTdT | 117 | UCCAUUAAUAAUGGGAUCCdTdT |
| 4 | GAUCCCAUUAUUAAUGGAAdTdT | 118 | UUCCAUUAAUAAUGGGAUCdTdT |
| 5 | AGUUAUUUAAAAGGUGUUAdTdT | 119 | UAACACCUUUUAAAUAACUdTdT |
| 6 | GUUAUUUAAAAGGUGUUAUdTdT | 120 | AUAACACCUUUUAAAUAACdTdT |
| 7 | AUUUAAAAGGUGUUAUCUCdTdT | 121 | GAGAUAACACCUUUUAAAUdTdT |
| 8 | UUAAAAGGUGUUAUCUCUUdTdT | 122 | AAGAGAUAACACCUUUUAAdTdT |
| 9 | AAGUCCACUACUAGAGCAUdTdT | 123 | AUGCUCUAGUAGUGGACUUdTdT |
| 10 | AGUCCACUACUAGAGCAUAdTdT | 124 | UAUGCUCUAGUAGUGGACUdTdT |

-continued

| SEQ ID NO. | Sense | SEQ ID NO. | Antisense |
|---|---|---|---|
| 11 | GUCCACUACUAGAGCAUAUdTdT | 125 | AUAUGCUCUAGUAGUGGACdTdT |
| 12 | UCCACUACUAGAGCAUAUGdTdT | 126 | CAUAUGCUCUAGUAGUGGAdTdT |
| 13 | GAAGAGCUAUAGAAAUAAGdTdT | 127 | CUUAUUUCUAUAGCUCUUCdTdT |
| 14 | GAGCUAUAGAAAUAAGUGAdTdT | 128 | UCACUUAUUUCUAUAGCUCdTdT |
| 15 | CUAUAGAAAUAAGUGAUGUdTdT | 129 | ACAUCACUUAUUUCUAUAGdTdT |
| 16 | UCAAAACAACACUCUUGAAdTdT | 130 | UUCAAGAGUGUUGUUUUGAdTdT |
| 17 | UAGAGGGAUUUAUUAUGUCdTdT | 131 | GACAUAAUAAAUCCCUCUAdTdT |
| 18 | AUAAAGGGUUUGUAAAUAdTdT | 132 | UAUUUACAAACCCUUUUAUdTdT |
| 19 | CUCAGUGUAGGUAGAAUGUdTdT | 133 | ACAUUCUACCUACACUGAGdTdT |
| 20 | UCAGUGUAGGUAGAAUGUUdTdT | 134 | AACAUUCUACCUACACUGAdTdT |
| 21 | CAGUGUAGGUAGAAUGUUUdTdT | 135 | AAACAUUCUACCUACACUGdTdT |
| 22 | AGUGUAGGUAGAAUGUUUGdTdT | 136 | CAAACAUUCUACCUACACUdTdT |
| 23 | GUGUAGGUAGAAUGUUUGCdTdT | 137 | GCAAACAUUCUACCUACACdTdT |
| 24 | ACAAGAUAUGGUGAUCUAGdTdT | 138 | CUAGAUCACCAUAUCUUGUdTdT |
| 25 | AGCAAAUUCAAUCAAGCAUdTdT | 139 | AUGCUUGAUUGAAUUUGCUdTdT |
| 26 | GCAAAUUCAAUCAAGCAUUdTdT | 140 | AAUGCUUGAUUGAAUUUGCdTdT |
| 27 | GAUGAACAAAGUGGAUUAUdTdT | 141 | AUAAUCCACUUUGUUCAUCdTdT |
| 28 | UAAUAUCUCUCAAAGGGAAdTdT | 142 | UUCCCUUUGAGAGAUAUUAdTdT |
| 29 | AUAUCUCUCAAAGGGAAAUdTdT | 143 | AUUUCCCUUUGAGAGAUAUdTdT |
| 30 | UAUCUCUCAAAGGGAAAUUdTdT | 144 | AAUUUCCCUUUGAGAGAUAdTdT |
| 31 | CAUGCUCAAGCAGAUUAUUdTdT | 145 | AAUAAUCUGCUUGAGCAUGdTdT |
| 32 | UGCUCAAGCAGAUUAUUUGdTdT | 146 | CAAAUAAUCUGCUUGAGCAdTdT |
| 33 | UAGCAUUAAAUAGCCUUAAdTdT | 147 | UUAAGGCUAUUUAAUGCUAdTdT |
| 34 | AGCAUUAAAUAGCCUUAAAdTdT | 148 | UUUAAGGCUAUUUAAUGCUdTdT |
| 35 | GCAUUAAAUAGCCUUAAAUdTdT | 149 | AUUUAAGGCUAUUUAAUGCdTdT |
| 36 | CAUUAAAUAGCCUUAAAUUdTdT | 150 | AAUUUAAGGCUAUUUAAUGdTdT |
| 37 | UAUUAUGCAGUUUAAUAUUdTdT | 151 | AAUAUUAAACUGCAUAAUAdTdT |
| 38 | UUAUGCAGUUUAAUAUUUAdTdT | 152 | UAAAUAUUAAACUGCAUAAdTdT |
| 39 | AAAAGUGCACAACAUUAUAdTdT | 153 | UAUAAUGUUGUGCACUUUUdTdT |
| 40 | AAAGUGCACAACAUUAUACdTdT | 154 | GUAUAAUGUUGUGCACUUUdTdT |
| 41 | AUAUAGAACCUACAUAUCCdTdT | 155 | GGAUAUGUAGGUUCUAUAUdTdT |
| 42 | UAUAGAACCUACAUAUCCUdTdT | 156 | AGGAUAUGUAGGUUCUAUAdTdT |
| 43 | UAAGAGUUGUUUAUGAAAGdTdT | 157 | CUUUCAUAAACAACUCUUAdTdT |
| 44 | ACAGUCAGUAGUAGACCAUdTdT | 158 | AUGGUCUACUACUGACUGUdTdT |
| 45 | CAGUCAGUAGUAGACCAUGdTdT | 159 | CAUGGUCUACUACUGACUGdTdT |
| 46 | AGUCAGUAGUAGACCAUGUdTdT | 160 | ACAUGGUCUACUACUGACUdTdT |
| 47 | GUCAGUAGUAGACCAUGUGdTdT | 161 | CACAUGGUCUACUACUGACdTdT |
| 48 | UCAGUAGUAGACCAUGUGAdTdT | 162 | UCACAUGGUCUACUACUGAdTdT |

-continued

| SEQ ID NO. | Sense | SEQ ID NO. | Antisense |
|---|---|---|---|
| 49 | CAUGUGAAUUCCCUGCAUCdTdT | 163 | GAUGCAGGGAAUUCACAUGdTdT |
| 50 | AUGUGAAUUCCCUGCAUCAdTdT | 164 | UGAUGCAGGGAAUUCACAUdTdT |
| 51 | UGUGAAUUCCCUGCAUCAAdTdT | 165 | UUGAUGCAGGGAAUUCACdTdT |
| 52 | GUGAAUUCCCUGCAUCAAUdTdT | 166 | AUUGAUGCAGGGAAUUCACdTdT |
| 53 | AAUUCCCUGCAUCAAUACCdTdT | 167 | GGUAUUGAUGCAGGGAAUUdTdT |
| 54 | GCAUCAAUACCAGCUUAUAdTdT | 168 | UAUAAGCUGGUAUUGAUGCdTdT |
| 55 | CAUCAAUACCAGCUUAUAGdTdT | 169 | CUAUAAGCUGGUAUUGAUGdTdT |
| 56 | AUACCAGCUUAUAGAACAAdTdT | 170 | UUGUUCUAUAAGCUGGUAUdTdT |
| 57 | UACCAGCUUAUAGAACAACdTdT | 171 | GUUGUUCUAUAAGCUGGUAdTdT |
| 58 | ACCAGCUUAUAGAACAACAdTdT | 172 | UGUUGUUCUAUAAGCUGGUdTdT |
| 59 | CCAGCUUAUAGAACAACAAdTdT | 173 | UUGUUGUUCUAUAAGCUGGdTdT |
| 60 | CAGCUUAUAGAACAACAAAdTdT | 174 | UUUGUUGUUCUAUAAGCUGdTdT |
| 61 | AUAGAACAACAAAUUAUCAdTdT | 175 | UGAUAAUUUGUUGUUCUAUdTdT |
| 62 | UAUUAACAGAAAAGUAUGGdTdT | 176 | CCAUACUUUUCUGUUAAUAdTdT |
| 63 | UGAGAUACAUUUGAUGAAAdTdT | 177 | UUUCAUCAAAUGUAUCUCAdTdT |
| 64 | GAGAUACAUUUGAUGAAACdTdT | 178 | GUUUCAUCAAAUGUAUCUCdTdT |
| 65 | GAUACAUUUGAUGAAACCUdTdT | 179 | AGGUUUCAUCAAAUGUAUCdTdT |
| 66 | AUACAUUUGAUGAAACCUCdTdT | 180 | GAGGUUUCAUCAAAUGUAUdTdT |
| 67 | UACAUUUGAUGAAACCUCCdTdT | 181 | GGAGGUUUCAUCAAAUGUAdTdT |
| 68 | AAGUGAUACAAAAACAGCAdTdT | 182 | UGCUGUUUUUGUAUCACUUdTdT |
| 69 | AGUGAUACAAAAACAGCAUdTdT | 183 | AUGCUGUUUUUGUAUCACUdTdT |
| 70 | UGAUACAAAAACAGCAUAUdTdT | 184 | AUAUGCUGUUUUUGUAUCAdTdT |
| 71 | UUUAAGUACUAAUUUAGCUdTdT | 185 | AGCUAAAUUAGUACUUAAAdTdT |
| 72 | UUAAGUACUAAUUUAGCUGdTdT | 186 | CAGCUAAAUUAGUACUUAAdTdT |
| 73 | UAAGUACUAAUUUAGCUGGdTdT | 187 | CCAGCUAAAUUAGUACUUAdTdT |
| 74 | AAGUACUAAUUUAGCUGGAdTdT | 188 | UCCAGCUAAAUUAGUACUUdTdT |
| 75 | AGUACUAAUUUAGCUGGACdTdT | 189 | GUCCAGCUAAAUUAGUACUdTdT |
| 76 | GUACUAAUUUAGCUGGACAdTdT | 190 | UGUCCAGCUAAAUUAGUACdTdT |
| 77 | ACUAAUUUAGCUGGACAUUdTdT | 191 | AAUGUCCAGCUAAAUUAGUdTdT |
| 78 | AAUUUAGCUGGACAUUGGAdTdT | 192 | UCCAAUGUCCAGCUAAAUUdTdT |
| 79 | AUUUAGCUGGACAUUGGAUdTdT | 193 | AUCCAAUGUCCAGCUAAAUdTdT |
| 80 | UUAGCUGGACAUUGGAUUCdTdT | 194 | GAAUCCAAUGUCCAGCUAAdTdT |
| 81 | UUUUGAAAAGAUUGGGGAdTdT | 195 | UCCCCAAUCUUUUCAAAAdTdT |
| 82 | UUUGAAAAGAUUGGGGAGdTdT | 196 | CUCCCCAAUCUUUUCAAAdTdT |
| 83 | UGAAAAGAUUGGGGAGAGdTdT | 197 | CUCUCCCCAAUCUUUUCAdTdT |
| 84 | GAAAAGAUUGGGGAGAGGdTdT | 198 | CCUCUCCCCAAUCUUUUCdTdT |
| 85 | UAUGAACACUUCAGAUCUUdTdT | 199 | AAGAUCUGAAGUGUUCAUAdTdT |
| 86 | AUGAACACUUCAGAUCUUCdTdT | 200 | GAAGAUCUGAAGUGUUCAUdTdT |

| SEQ ID NO. | Sense | SEQ ID NO. | Antisense |
|---|---|---|---|
| 87 | UGCCCUUGGGUUGUUAACAdTdT | 201 | UGUUAACAACCCAAGGGCAdTdT |
| 88 | GCCCUUGGGUUGUUAACAUdTdT | 202 | AUGUUAACAACCCAAGGGCdTdT |
| 89 | UAUAGCAUUCAUAGGUGAAdTdT | 203 | UUCACCUAUGAAUGCUAUAdTdT |
| 90 | AUAGCAUUCAUAGGUGAAGdTdT | 204 | CUUCACCUAUGAAUGCUAUdTdT |
| 91 | UAGCAUUCAUAGGUGAAGGdTdT | 205 | CCUUCACCUAUGAAUGCUAdTdT |
| 92 | AUUCAUAGGUGAAGGAGCAdTdT | 206 | UGCUCCUUCACCUAUGAAUdTdT |
| 93 | UUGCAAUGAUCAUAGUUUAdTdT | 207 | UAAACUAUGAUCAUUGCAAdTdT |
| 94 | UGCAAUGAUCAUAGUUUACdTdT | 208 | GUAAACUAUGAUCAUUGCAdTdT |
| 95 | GCAAUGAUCAUAGUUUACCdTdT | 209 | GGUAAACUAUGAUCAUUGCdTdT |
| 96 | CAAUGAUCAUAGUUUACCUdTdT | 210 | AGGUAAACUAUGAUCAUUGdTdT |
| 97 | AAUGAUCAUAGUUUACCUAdTdT | 211 | UAGGUAAACUAUGAUCAUUdTdT |
| 98 | AUGAUCAUAGUUUACCUAUdTdT | 212 | AUAGGUAAACUAUGAUCAUdTdT |
| 99 | GAUCAUAGUUUACCUAUUGdTdT | 213 | CAAUAGGUAAACUAUGAUCdTdT |
| 100 | AUCAUAGUUUACCUAUUGAdTdT | 214 | UCAAUAGGUAAACUAUGAUdTdT |
| 101 | UCAUAGUUUACCUAUUGAGdTdT | 215 | CUCAAUAGGUAAACUAUGAdTdT |
| 102 | CAUAGUUUACCUAUUGAGUdTdT | 216 | ACUCAAUAGGUAAACUAUGdTdT |
| 103 | AUAGUUUACCUAUUGAGUUdTdT | 217 | AACUCAAUAGGUAAACUAUdTdT |
| 104 | CAUUGGUCUUAUUUACAUUdTdT | 218 | UAUGUAAAUAAGACCAAUGdTdT |
| 105 | UUGGUCUUAUUUACAUAUdTdT | 219 | UAUAUGUAAAUAAGACCAAdTdT |
| 106 | UGGUCUUAUUUACAUAUAAdTdT | 220 | UUAUAUGUAAAUAAGACCAdTdT |
| 107 | GGUCUUAUUUACAUAUAAAdTdT | 221 | UUUAUAUGUAAAUAAGACCdTdT |
| 108 | AUAUCAUGCUCAAGAUGAUdTdT | 222 | AUCAUCUUGAGCAUGAUAUdTdT |
| 109 | UAUCAUGCUCAAGAUGAUAdTdT | 223 | UAUCAUCUUGAGCAUGAUAdTdT |
| 110 | UGAUAUUGAUUUCAAAUUAdTdT | 224 | UAAUUUGAAAUCAAUAUCAdTdT |
| 111 | UACUUAGUCCUUACAAUAGdTdT | 225 | CUAUUGUAAGGACUAAGUAdTdT |
| 112 | UUAGUCCUUACAAUAGGUCdTdT | 226 | GACCUAUUGUAAGGACUAAdTdT |
| 113 | UAGUCCUUACAAUAGGUCCdTdT | 227 | GGACCUAUUGUAAGGACUAdTdT |
| 114 | AUAUUCUAUAGCUGGACGUdTdT | 228 | ACGUCCAGCUAUAGAAUAUdTdT |
| 115 | UAUUCUAUAGCUGGACGUAdTdT | 229 | UACGUCCAGCUAUAGAAUAdTdT |
| 116 | AUUCUAUAGCUGGACGUAAdTdT | 230 | UUACGUCCAGCUAUAGAAUdTdT |
| 231 | AAAUUCCUAGAAUCAAUAAdTdT | 250 | UUAUUGAUUCUAGGAAUUUdTdT |
| 232 | AAUUCCUAGAAUCAAUAAAdTdT | 251 | UUUAUUGAUUCUAGGAAUUdTdT |
| 233 | UUCCUAGAAUCAAUAAAGGdTdT | 252 | CCUUUAUUGAUUCUAGGAAdTdT |
| 234 | UCCUAGAAUCAAUAAAGGGdTdT | 253 | CCCUUUAUUGAUUCUAGGAdTdT |
| 235 | CUAGAAUCAAUAAAGGGCAdTdT | 254 | UGCCCUUUAUUGAUUCUAGdTdT |
| 236 | ACAUUUGAUAACAAUGAAGdTdT | 255 | CUUCAUUGUUAUCAAAUGUdTdT |
| 237 | CAUUUGAUAACAAUGAAGAdTdT | 256 | UCUUCAUUGUUAUCAAAUGdTdT |
| 238 | AUUUGAUAACAAUGAAGAAdTdT | 257 | UUCUUCAUUGUUAUCAAAUdTdT |

-continued

| SEQ ID NO. | Sense | SEQ ID NO. | Antisense |
|---|---|---|---|
| 239 | UUUGAUAACAAUGAAGAAGdTdT | 258 | CUUCUUCAUUGUUAUCAAAdTdT |
| 240 | AAGUGAAAUACUAGGAAUGdTdT | 259 | CAUUCCUAGUAUUUCACUUdTdT |
| 241 | AGUGAAAUACUAGGAAUGCdTdT | 260 | GCAUUCCUAGUAUUUCACUdTdT |
| 242 | GUGAAAUACUAGGAAUGCUdTdT | 261 | AGCAUUCCUAGUAUUUCACdTdT |
| 243 | UGAAAUACUAGGAAUGCUUdTdT | 262 | AAGCAUUCCUAGUAUUUCAdTdT |
| 244 | GAAAUACUAGGAAUGCUUCdTdT | 263 | GAAGCAUUCCUAGUAUUUCdTdT |
| 245 | AAAUACUAGGAAUGCUUCAdTdT | 264 | UGAAGCAUUCCUAGUAUUUdTdT |
| 246 | GAAGCAUUAAUGACCAAUGdTdT | 265 | CAUUGGUCAUUAAUGCUUCdTdT |
| 247 | AAGCAUUAAUGACCAAUGAdTdT | 266 | UCAUUGGUCAUUAAUGCUUdTdT |
| 248 | CGAUAAUAUAACAGCAAGAdTsdT | 267 | UCUUGCUGUUAUAUUAUCGdTsdT |
| 249 | CGAUUAUAUUACAGGAUGAdTsdT | 268 | UCAUCCUGUAAUAUAAUCGdTsdT |
| 1 | GGCUCUUAGCAAAGUCAAGdTdT | 2 | CUUGACUUUGCUAAGAGCCdTdT |
| 269 | CUCUUAGCAAAGUCAAGUUdTdT | 277 | AACUUGACUUUGCUAAGAGdTdT |
| 270 | CUGUCAUCCAGCAAAUACAdTdT | 278 | UGUAUUUGCUGGAUGACAGdTdT |
| 271 | UGUCAUCCAGCAAAUACACdTdT | 279 | GUGUAUUUGCUGGAUGACAdTdT |
| 272 | UAAUAGGUAUGUUAUAUGCdTdT | 280 | GCAUAUAACAUACCUAUUAdTdT |
| 273 | AUUGAGAUAGAAUCUAGAAdTdT | 281 | UUCUAGAUUCUAUCUCAAUdTdT |
| 274 | AUUCUACCAUAUAUUGAACdTdT | 282 | GUUCAAUAUAUGGUAGAAUdTdT |
| 275 | UUCUACCAUAUAUUGAACAdTdT | 283 | UGUUCAAUAUAUGGUAGAAdTdT |
| 276 | UCUACCAUAUAUUGAACAAdTdT | 284 | UUGUUCAAUAUAUGGUAGAdTdT. |

26. A method of reducing the risk of Respiratory Syncytial Virus (RSV) associated bronchiolitis obliterans syndrome (BOS) in a human lung transplant recipient, comprising administering to said subject a composition comprising a therapeutically effective amount of a dsRNA that targets a P, N, or L gene of RSV wherein the dsRNA comprises a sense strand and an antisense strand and each strand is 15-30 nucleotides in length, wherein the antisense strand of the dsRNA targeting the N gene is complementary to at least 15 contiguous nucleotides of SEQ ID NOS: 277-284, wherein ribavirin is administered to said human lung transplant recipient, and wherein the composition is administered daily as an aerosol produced by a PARI eFlow® 30L nebulizer.

27. A method of reducing the risk of Respiratory Syncytial Virus (RSV) associated bronchiolitis obliterans syndrome (BOS) in a human lung transplant recipient, comprising administering to said subject a composition comprising a therapeutically effective amount of a dsRNA that targets a P, N, or L gene of RSV wherein the dsRNA comprises a sense strand and an antisense strand and each strand is 15-30 nucleotides in length, wherein ribavirin is administered to said human lung transplant recipient, wherein the composition is administered daily as an aerosol produced by a PARI eFlow® 30L nebulizer, and wherein the dsRNA comprises one of the following sense strand and antisense strand pairs:

| SEQ ID NO. | Sense | SEQ ID NO. | Antisense |
|---|---|---|---|
| 3 | GGAUCCCAUUAUUAAUGGAdTdT | 117 | UCCAUUAAUAAUGGGAUCCdTdT |
| 4 | GAUCCCAUUAUUAAUGGAAdTdT | 118 | UUCCAUUAAUAAUGGGAUCdTdT |
| 5 | AGUUAUUUAAAAGGUGUUAdTdT | 119 | UAACACCUUUUAAAUAACUdTdT |
| 6 | GUUAUUUAAAAGGUGUUAUdTdT | 120 | AUAACACCUUUUAAAUAACdTdT |
| 7 | AUUUAAAAGGUGUUAUCUCdTdT | 121 | GAGAUAACACCUUUUAAAUdTdT |
| 8 | UUAAAAGGUGUUAUCUCUUdTdT | 122 | AAGAGAUAACACCUUUUAAdTdT |
| 9 | AAGUCCACUACUAGAGCAUdTdT | 123 | AUGCUCUAGUAGUGGACUUdTdT |

-continued

| SEQ ID NO. | Sense | SEQ ID NO. | Antisense |
|---|---|---|---|
| 10 | AGUCCACUACUAGAGCAUAdTdT | 124 | UAUGCUCUAGUAGUGGACUdTdT |
| 11 | GUCCACUACUAGAGCAUAUdTdT | 125 | AUAUGCUCUAGUAGUGGACdTdT |
| 12 | UCCACUACUAGAGCAUAUGdTdT | 126 | CAUAUGCUCUAGUAGUGGAdTdT |
| 13 | GAAGAGCUAUAGAAAUAAGdTdT | 127 | CUUAUUUCUAUAGCUCUUCdTdT |
| 14 | GAGCUAUAGAAAUAAGUGAdTdT | 128 | UCACUUAUUUCUAUAGCUCdTdT |
| 15 | CUAUAGAAAUAAGUGAUGUdTdT | 129 | ACAUCACUUAUUUCUAUAGdTdT |
| 16 | UCAAACAACACUCUUGAAdTdT | 130 | UUCAAGAGUGUUGUUUUGAdTdT |
| 17 | UAGAGGGAUUUAUUAUGUCdTdT | 131 | GACAUAAUAAAUCCCUCUAdTdT |
| 18 | AUAAAGGGUUUGUAAAUAdTdT | 132 | UAUUUACAAACCCUUUUAUdTdT |
| 19 | CUCAGUGUAGGUAGAAUGUdTdT | 133 | ACAUUCUACCUACACUGAGdTdT |
| 20 | UCAGUGUAGGUAGAAUGUUdTdT | 134 | AACAUUCUACCUACACUGAdTdT |
| 21 | CAGUGUAGGUAGAAUGUUUdTdT | 135 | AAACAUUCUACCUACACUdTdT |
| 22 | AGUGUAGGUAGAAUGUUUGdTdT | 136 | CAAACAUUCUACCUACACUdTdT |
| 23 | GUGUAGGUAGAAUGUUUGCdTdT | 137 | GCAAACAUUCUACCUACACdTdT |
| 24 | ACAAGAUAUGGUGAUCUAGdTdT | 138 | CUAGAUCACCAUAUCUUGUdTdT |
| 25 | AGCAAAUUCAAUCAAGCAUdTdT | 139 | AUGCUUGAUUGAAUUUGCUdTdT |
| 26 | GCAAAUUCAAUCAAGCAUUdTdT | 140 | AAUGCUUGAUUGAAUUUGCdTdT |
| 27 | GAUGAACAAAGUGGAUUAUdTdT | 141 | AUAAUCCACUUUGUUCAUCdTdT |
| 28 | UAAUAUCUCUCAAAGGGAAdTdT | 142 | UUCCCUUUGAGAGAUAUUAdTdT |
| 29 | AUAUCUCUCAAAGGGAAAUdTdT | 143 | AUUUCCCUUUGAGAGAUAUdTdT |
| 30 | UAUCUCUCAAAGGGAAAUUdTdT | 144 | AAUUUCCCUUUGAGAGAUAdTdT |
| 31 | CAUGCUCAAGCAGAUUAUUdTdT | 145 | AAUAAUCUGCUUGAGCAUGdTdT |
| 32 | UGCUCAAGCAGAUUAUUGdTdT | 146 | CAAAUAAUCUGCUUGAGCAdTdT |
| 33 | UAGCAUUAAAUAGCCUUAAdTdT | 147 | UUAAGGCUAUUUAAUGCUAdTdT |
| 34 | AGCAUUAAAUAGCCUUAAAdTdT | 148 | UUUAAGGCUAUUUAAUGCUdTdT |
| 35 | GCAUUAAAUAGCCUUAAAUdTdT | 149 | AUUUAAGGCUAUUUAAUGCdTdT |
| 36 | CAUUAAAUAGCCUUAAAUUdTdT | 150 | AAUUUAAGGCUAUUUAAUGdTdT |
| 37 | UAUUAUGCAGUUUAAUAUUdTdT | 151 | AAUAUUAAACUGCAUAAUAdTdT |
| 38 | UUAUGCAGUUUAAUAUUAdTdT | 152 | UAAAUAUUAAACUGCAUAAdTdT |
| 39 | AAAAGUGCACAACAUUAUAdTdT | 153 | UAUAAUGUUGUGCACUUUUdTdT |
| 40 | AAAGUGCACAACAUUAUACdTdT | 154 | GUAUAAUGUUGUGCACUUUdTdT |
| 41 | AUAUAGAACCUACAUAUCCdTdT | 155 | GGAUAUGUAGGUUCUAUAUdTdT |
| 42 | UAUAGAACCUACAUAUCCUdTdT | 156 | AGGAUAUGUAGGUUCUAUAdTdT |
| 43 | UAAGAGUUGUUUAUGAAAGdTdT | 157 | CUUUCAUAAACAACUCUUAdTdT |
| 44 | ACAGUCAGUAGUAGACCAUdTdT | 158 | AUGGUCUACUACUGACUGUdTdT |
| 45 | CAGUCAGUAGUAGACCAUGdTdT | 159 | CAUGGUCUACUACUGACUGdTdT |
| 46 | AGUCAGUAGUAGACCAUGUdTdT | 160 | ACAUGGUCUACUACUGACUdTdT |
| 47 | GUCAGUAGUAGACCAUGUGdTdT | 161 | CACAUGGUCUACUACUGACdTdT |

-continued

| SEQ ID NO. | Sense | SEQ ID NO. | Antisense |
|---|---|---|---|
| 48 | UCAGUAGUAGACCAUGUGAdTdT | 162 | UCACAUGGUCUACUACUGAdTdT |
| 49 | CAUGUGAAUUCCCUGCAUCdTdT | 163 | GAUGCAGGGAAUUCACAUGdTdT |
| 50 | AUGUGAAUUCCCUGCAUCAdTdT | 164 | UGAUGCAGGGAAUUCACAUdTdT |
| 51 | UGUGAAUUCCCUGCAUCAAdTdT | 165 | UUGAUGCAGGGAAUUCACAdTdT |
| 52 | GUGAAUUCCCUGCAUCAAUdTdT | 166 | AUUGAUGCAGGGAAUUCACdTdT |
| 53 | AAUUCCCUGCAUCAAUACCdTdT | 167 | GGUAUUGAUGCAGGGAAUUdTdT |
| 54 | GCAUCAAUACCAGCUUAUAdTdT | 168 | UAUAAGCUGGUAUUGAUGCdTdT |
| 55 | CAUCAAUACCAGCUUAUAGdTdT | 169 | CUAUAAGCUGGUAUUGAUGdTdT |
| 56 | AUACCAGCUUAUAGAACAAdTdT | 170 | UUGUUCUAUAAGCUGGUAUdTdT |
| 57 | UACCAGCUUAUAGAACAACdTdT | 171 | GUUGUUCUAUAAGCUGGUAdTdT |
| 58 | ACCAGCUUAUAGAACAACAdTdT | 172 | UGUUGUUCUAUAAGCUGGUdTdT |
| 59 | CCAGCUUAUAGAACAACAAdTdT | 173 | UUGUUGUUCUAUAAGCUGGdTdT |
| 60 | CAGCUUAUAGAACAACAAAdTdT | 174 | UUUGUUGUUCUAUAAGCUGdTdT |
| 61 | AUAGAACAACAAAUUAUCdTdT | 175 | UGAUAAUUUGUUGUUCUAUdTdT |
| 62 | UAUUAACAGAAAAGUAUGGdTdT | 176 | CCAUACUUUUCUGUUAAUAdTdT |
| 63 | UGAGAUACAUUUGAUGAAAdTdT | 177 | UUUCAUCAAAUGUAUCUCAdTdT |
| 64 | GAGAUACAUUUGAUGAAACdTdT | 178 | GUUUCAUCAAAUGUAUCUCdTdT |
| 65 | GAUACAUUUGAUGAAACCUdTdT | 179 | AGGUUUCAUCAAAUGUAUCdTdT |
| 66 | AUACAUUUGAUGAAACCUCdTdT | 180 | GAGGUUUCAUCAAAUGUAUdTdT |
| 67 | UACAUUUGAUGAAACCUCCdTdT | 181 | GGAGGUUUCAUCAAAUGUAdTdT |
| 68 | AAGUGAUACAAAAACAGCAdTdT | 182 | UGCUGUUUUUGUAUCACUUdTdT |
| 69 | AGUGAUACAAAAACAGCAUdTdT | 183 | AUGCUGUUUUUGUAUCACUdTdT |
| 70 | UGAUACAAAAACAGCAUAUdTdT | 184 | AUAUGCUGUUUUUGUAUCAdTdT |
| 71 | UUUAAGUACUAAUUUAGCUdTdT | 185 | AGCUAAAUUAGUACUUAAAdTdT |
| 72 | UUAAGUACUAAUUUAGCUGdTdT | 186 | CAGCUAAAUUAGUACUUAAdTdT |
| 73 | UAAGUACUAAUUUAGCUGGdTdT | 187 | CCAGCUAAAUUAGUACUUAdTdT |
| 74 | AAGUACUAAUUUAGCUGGAdTdT | 188 | UCCAGCUAAAUUAGUACUUdTdT |
| 75 | AGUACUAAUUUAGCUGGACdTdT | 189 | GUCCAGCUAAAUUAGUACUdTdT |
| 76 | GUACUAAUUUAGCUGGACAdTdT | 190 | UGUCCAGCUAAAUUAGUACdTdT |
| 77 | ACUAAUUUAGCUGGACAUUdTdT | 191 | AAUGUCCAGCUAAAUUAGUdTdT |
| 78 | AAUUUAGCUGGACAUUGGAdTdT | 192 | UCCAAUGUCCAGCUAAAUUdTdT |
| 79 | AUUUAGCUGGACAUUGGAUdTdT | 193 | AUCCAAUGUCCAGCUAAAUdTdT |
| 80 | UUAGCUGGACAUUGGAUUCdTdT | 194 | GAAUCCAAUGUCCAGCUAAdTdT |
| 81 | UUUUGAAAAGAUUGGGGAdTdT | 195 | UCCCCAAUCUUUUCAAAAdTdT |
| 82 | UUUGAAAAGAUUGGGGAGdTdT | 196 | CUCCCCAAUCUUUUCAAAdTdT |
| 83 | UGAAAAGAUUGGGGAGAGdTdT | 197 | CUCUCCCCAAUCUUUUCAdTdT |
| 84 | GAAAAGAUUGGGGAGAGGdTdT | 198 | CCUCUCCCCAAUCUUUUCdTdT |
| 85 | UAUGAACACUUCAGAUCUUdTdT | 199 | AAGAUCUGAAGUGUUCAUAdTdT |

-continued

| SEQ ID NO. | Sense | SEQ ID NO. | Antisense |
|---|---|---|---|
| 86 | AUGAACACUUCAGAUCUUCdTdT | 200 | GAAGAUCUGAAGUGUUCAUdTdT |
| 87 | UGCCCUUGGGUUGUUAACAdTdT | 201 | UGUUAACAACCCAAGGGCAdTdT |
| 88 | GCCCUUGGGUUGUUAACAUdTdT | 202 | AUGUUAACAACCCAAGGGCdTdT |
| 89 | UAUAGCAUUCAUAGGUGAAdTdT | 203 | UUCACCUAUGAAUGCUAUAdTdT |
| 90 | AUAGCAUUCAUAGGUGAAGdTdT | 204 | CUUCACCUAUGAAUGCUAUdTdT |
| 91 | UAGCAUUCAUAGGUGAAGGdTdT | 205 | CCUUCACCUAUGAAUGCUAdTdT |
| 92 | AUUCAUAGGUGAAGGAGCAdTdT | 206 | UGCUCCUUCACCUAUGAAUdTdT |
| 93 | UUGCAAUGAUCAUAGUUUAdTdT | 207 | UAAACUAUGAUCAUUGCAAdTdT |
| 94 | UGCAAUGAUCAUAGUUUACdTdT | 208 | GUAAACUAUGAUCAUUGCAdTdT |
| 95 | GCAAUGAUCAUAGUUUACCdTdT | 209 | GGUAAACUAUGAUCAUUGCdTdT |
| 96 | CAAUGAUCAUAGUUUACCUdTdT | 210 | AGGUAAACUAUGAUCAUUGdTdT |
| 97 | AAUGAUCAUAGUUUACCUAdTdT | 211 | UAGGUAAACUAUGAUCAUUdTdT |
| 98 | AUGAUCAUAGUUUACCUAUdTdT | 212 | AUAGGUAAACUAUGAUCAUdTdT |
| 99 | GAUCAUAGUUUACCUAUUGdTdT | 213 | CAAUAGGUAAACUAUGAUCdTdT |
| 100 | AUCAUAGUUUACCUAUUGAdTdT | 214 | UCAAUAGGUAAACUAUGAUdTdT |
| 101 | UCAUAGUUUACCUAUUGAGdTdT | 215 | CUCAAUAGGUAAACUAUGAdTdT |
| 102 | CAUAGUUUACCUAUUGAGUdTdT | 216 | ACUCAAUAGGUAAACUAUGdTdT |
| 103 | AUAGUUUACCUAUUGAGUUdTdT | 217 | AACUCAAUAGGUAAACUAUdTdT |
| 104 | CAUUGGUCUUAUUUACAUdTdT | 218 | UAUGUAAAUAAGACCAAUGdTdT |
| 105 | UUGGUCUUAUUUACAUAUdTdT | 219 | UAUAUGUAAAUAAGACCAAdTdT |
| 106 | UGGUCUUAUUUACAUAUAAdTdT | 220 | UUAUAUGUAAAUAAGACCAdTdT |
| 107 | GGUCUUAUUUACAUAUAAAdTdT | 221 | UUUAUAUGUAAAUAAGACCdTdT |
| 108 | AUAUCAUGCUCAAGAUGAUdTdT | 222 | AUCAUCUUGAGCAUGAUAUdTdT |
| 109 | UAUCAUGCUCAAGAUGAUAdTdT | 223 | UAUCAUCUUGAGCAUGAUAdTdT |
| 110 | UGAUAUUGAUUUCAAAUUAdTdT | 224 | UAAUUUGAAAUCAAUAUCAdTdT |
| 111 | UACUUAGUCCUUACAAUAGdTdT | 225 | CUAUUGUAAGGACUAAGUAdTdT |
| 112 | UUAGUCCUUACAAUAGGUCdTdT | 226 | GACCUAUUGUAAGGACUAAdTdT |
| 113 | UAGUCCUUACAAUAGGUCCdTdT | 227 | GGACCUAUUGUAAGGACUAdTdT |
| 114 | AUAUUCUAUAGCUGGACGUdTdT | 228 | ACGUCCAGCUAUAGAAUAUdTdT |
| 115 | UAUUCUAUAGCUGGACGUAdTdT | 229 | UACGUCCAGCUAUAGAAUAdTdT |
| 116 | AUUCUAUAGCUGGACGUAAdTdT | 230 | UUACGUCCAGCUAUAGAAUdTdT |
| 231 | AAAUUCCUAGAAUCAAUAAdTdT | 250 | UUAUUGAUUCUAGGAAUUUdTdT |
| 232 | AAUUCCUAGAAUCAAUAAAdTdT | 251 | UUUAUUGAUUCUAGGAAUUdTdT |
| 233 | UUCCUAGAAUCAAUAAAGGdTdT | 252 | CCUUUAUUGAUUCUAGGAAdTdT |
| 234 | UCCUAGAAUCAAUAAAGGGdTdT | 253 | CCCUUUAUUGAUUCUAGGAdTdT |
| 235 | CUAGAAUCAAUAAAGGGCAdTdT | 254 | UGCCCUUUAUUGAUUCUAGdTdT |
| 236 | ACAUUUGAUAACAAUGAAGdTdT | 255 | CUUCAUUGUUAUCAAAUGUdTdT |
| 237 | CAUUUGAUAACAAUGAAGAdTdT | 256 | UCUUCAUUGUUAUCAAAUGdTdT |

-continued

| SEQ ID NO. | Sense | SEQ ID NO. | Antisense |
|---|---|---|---|
| 238 | AUUUGAUAACAAUGAAGAAdTdT | 257 | UUCUUCAUUGUUAUCAAAUdTdT |
| 239 | UUUGAUAACAAUGAAGAAGdTdT | 258 | CUUCUUCAUUGUUAUCAAAdTdT |
| 240 | AAGUGAAAUACUAGGAAUGdTdT | 259 | CAUUCCUAGUAUUUCACUUdTdT |
| 241 | AGUGAAAUACUAGGAAUGCdTdT | 260 | GCAUUCCUAGUAUUUCACUdTdT |
| 242 | GUGAAAUACUAGGAAUGCUdTdT | 261 | AGCAUUCCUAGUAUUUCACdTdT |
| 243 | UGAAAUACUAGGAAUGCUUdTdT | 262 | AAGCAUUCCUAGUAUUUCAdTdT |
| 244 | GAAAUACUAGGAAUGCUUCdTdT | 263 | GAAGCAUUCCUAGUAUUUCdTdT |
| 245 | AAAUACUAGGAAUGCUUCAdTdT | 264 | UGAAGCAUUCCUAGUAUUUdTdT |
| 246 | GAAGCAUUAAUGACCAAUGdTdT | 265 | CAUUGGUCAUUAAUGCUUCdTdT |
| 247 | AAGCAUUAAUGACCAAUGAdTdT | 266 | UCAUUGGUCAUUAAUGCUUdTdT |
| 248 | CGAUAAUAUAACAGCAAGAdTsdT | 267 | UCUUGCUGUUAUAUUAUCGdTsdT |
| 249 | CGAUUAUAUUACAGGAUGAdTsdT | 268 | UCAUCCUGUAAUAUAAUCGdTsdT |
| 1 | GGCUCUUAGCAAAGUCAAGdTdT | 2 | CUUGACUUUGCUAAGAGCCdTdT |
| 269 | CUCUUAGCAAAGUCAAGUUdTdT | 277 | AACUUGACUUUGCUAAGAGdTdT |
| 270 | CUGUCAUCCAGCAAAUACAdTdT | 278 | UGUAUUUGCUGGAUGACAGdTdT |
| 271 | UGUCAUCCAGCAAAUACACdTdT | 279 | GUGUAUUUGCUGGAUGACAdTdT |
| 272 | UAAUAGGUAUGUUAUAUGCdTdT | 280 | GCAUAUAACAUACCUAUUAdTdT |
| 273 | AUUGAGAUAGAAUCUAGAAdTdT | 281 | UUCUAGAUUCUAUCUCAAUdTdT |
| 274 | AUUCUACCAUAUAUUGAACdTdT | 282 | GUUCAAUAUAUGGUAGAAUdTdT |
| 275 | UUCUACCAUAUAUUGAACAdTdT | 283 | UGUUCAAUAUAUGGUAGAAdTdT |
| 276 | UCUACCAUAUAUUGAACAAdTdT | 284 | UUGUUCAAUAUAUGGUAGAdTdT. |

\* \* \* \* \*